United States Patent
Bekker

(10) Patent No.: US 11,779,576 B2
(45) Date of Patent: *Oct. 10, 2023

(54) METHOD OF TREATING C3 GLOMERULOPATHY

(71) Applicant: CHEMOCENTRYX, INC., San Carlos, CA (US)

(72) Inventor: Petrus Bekker, Los Altos, CA (US)

(73) Assignee: CHEMOCENTRYX, INC., Thousand Oaks, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/670,604

(22) Filed: Feb. 14, 2022

(65) Prior Publication Data

US 2022/0354837 A1 Nov. 10, 2022

Related U.S. Application Data

(63) Continuation of application No. 16/184,535, filed on Nov. 8, 2018, now Pat. No. 11,285,138, which is a continuation of application No. 15/404,610, filed on Jan. 12, 2017, now abandoned.

(60) Provisional application No. 62/397,527, filed on Sep. 21, 2016, provisional application No. 62/347,450, filed on Jun. 8, 2016, provisional application No. 62/280,346, filed on Jan. 19, 2016, provisional application No. 62/278,788, filed on Jan. 14, 2016.

(51) Int. Cl.
*A61K 31/451* (2006.01)
*A61K 45/06* (2006.01)
*A61P 13/12* (2006.01)
*A61K 31/454* (2006.01)

(52) U.S. Cl.
CPC .......... *A61K 31/451* (2013.01); *A61K 31/454* (2013.01); *A61K 45/06* (2013.01); *A61P 13/12* (2018.01)

(58) Field of Classification Search
CPC .............................. A61K 31/451; A61P 13/12
See application file for complete search history.

(56) References Cited

U.S. PATENT DOCUMENTS

| | | |
|---|---|---|
| 4,686,100 A | 8/1987 | Raffin et al. |
| 6,713,502 B2 | 3/2004 | Dhanak et al. |
| 7,105,567 B2 | 9/2006 | Ishibuchi et al. |
| 7,169,775 B2 | 1/2007 | Thurkauf et al. |
| 7,427,615 B2 | 9/2008 | Uehara et al. |
| 7,455,837 B2 | 11/2008 | Guo et al. |
| 7,635,698 B2 | 12/2009 | Rosse et al. |
| 7,834,035 B2 | 11/2010 | Bessis et al. |
| 8,007,767 B2 | 8/2011 | Thurkauf et al. |
| 8,026,367 B2 | 9/2011 | Allegretti et al. |
| 8,198,454 B2 | 6/2012 | Nakamura et al. |
| 8,206,716 B2 | 6/2012 | Fung et al. |
| 8,372,404 B2 | 2/2013 | Fung et al. |
| 8,445,515 B2 | 5/2013 | Fan et al. |
| 8,906,938 B2 | 12/2014 | Fan et al. |
| 9,126,939 B2 | 9/2015 | Fan et al. |
| 9,573,897 B2 | 2/2017 | Fan et al. |
| 9,745,268 B2 | 8/2017 | Fan et al. |
| 10,035,768 B2 | 7/2018 | Fan et al. |
| 10,266,492 B2 | 4/2019 | Fan et al. |
| 10,532,982 B2 | 1/2020 | Fan et al. |
| 10,660,897 B2 | 5/2020 | Fan et al. |
| 11,285,138 B2 | 3/2022 | Bekker |
| 2003/0195192 A1 | 10/2003 | Haviv et al. |
| 2003/0195195 A1 | 10/2003 | Haviv et al. |
| 2004/0014744 A1 | 1/2004 | Haviv et al. |
| 2004/0014782 A1 | 1/2004 | Krause |
| 2006/0004049 A1 | 1/2006 | Yao et al. |
| 2006/0019995 A1 | 1/2006 | Rault et al. |
| 2006/0030557 A1 | 2/2006 | Haviv et al. |
| 2006/0154917 A1 | 7/2006 | Zhang et al. |
| 2007/0117802 A1 | 5/2007 | Borzilleri et al. |
| 2010/0074863 A1 | 3/2010 | Or et al. |
| 2010/0104558 A1 | 4/2010 | Tharaux et al. |
| 2010/0179150 A1 | 7/2010 | Basarab et al. |
| 2010/0190824 A1 | 7/2010 | Kumar et al. |
| 2010/0311753 A1 | 12/2010 | Fan et al. |
| 2011/0275639 A1 | 11/2011 | Fan et al. |
| 2012/0225056 A1 | 9/2012 | Rother et al. |
| 2013/0317028 A1 | 11/2013 | Fan et al. |
| 2015/0126492 A1 | 5/2015 | Dechanstsreiter et al. |
| 2015/0141425 A1 | 5/2015 | Fan et al. |
| 2017/0065604 A1 | 3/2017 | Fan et al. |
| 2017/0114017 A1 | 4/2017 | Fan et al. |
| 2017/0202821 A1 | 7/2017 | Bekker |
| 2019/0062275 A1 | 2/2019 | Fan et al. |
| 2020/0017598 A1 | 1/2020 | Andersson et al. |
| 2020/0354320 A1 | 11/2020 | Fan et al. |

(Continued)

FOREIGN PATENT DOCUMENTS

| | | |
|---|---|---|
| JP | 2005-536533 A | 12/2005 |
| JP | 2009-530299 A | 8/2009 |

(Continued)

OTHER PUBLICATIONS

Extended European Search Report corresponding to EP 09835688.4 (PCT/US2009/068941) dated Aug. 2, 2012, 5 pages.
Extended European Search Report corresponding to EP 11799027.5 (PCT/US2011/041910) dated Dec. 18, 2013, 4 pages.
Extended European Search Report corresponding to EP 16167779.4 dated Jun. 30, 2016; 6 pages.
Extended European Search Report corresponding to EP 15845610.3 dated May 16, 2018; 18 pages.
Extended European Search Report corresponding to EP 19154555.7 dated Apr. 17, 2019; 6 pages.
Extended European Search Report corresponding to EP 17738902.0 dated Jul. 26, 2019; 12 pages.

(Continued)

*Primary Examiner* — James D. Anderson
(74) *Attorney, Agent, or Firm* — Mintz Levin Cohn Ferris Glovsky and Popeo PC

(57) ABSTRACT

Methods of treating a human suffering from or susceptible to C3 glomerulopathy comprising administering to the human an effective amount of a C5aR antagonist are provided.

13 Claims, 1 Drawing Sheet

(56) References Cited

U.S. PATENT DOCUMENTS

| | | | |
|---|---|---|---|
| 2021/0269398 | A1 | 9/2021 | Fan et al. |
| 2022/0257580 | A1 | 8/2022 | Schall et al. |
| 2023/0102258 | A1 | 3/2023 | Fan et al. |

FOREIGN PATENT DOCUMENTS

| | | |
|---|---|---|
| JP | 5819730 B2 | 6/2012 |
| RU | 2197288 C2 | 1/2003 |
| WO | 00/12074 | 3/2000 |
| WO | 02/049993 | 6/2002 |
| WO | 03/029187 A1 | 4/2003 |
| WO | 03/082826 A1 | 10/2003 |
| WO | 03/082828 A1 | 10/2003 |
| WO | 03/084524 A1 | 10/2003 |
| WO | 2004/014905 A1 | 2/2004 |
| WO | 2004/018460 A1 | 3/2004 |
| WO | 2004/043925 | 5/2004 |
| WO | 2004/100975 A1 | 11/2004 |
| WO | 2004/110996 A1 | 12/2004 |
| WO | 2005/007087 | 1/2005 |
| WO | 2006/012226 | 2/2006 |
| WO | 2007/051062 A2 | 5/2007 |
| WO | 2007/106585 A1 | 9/2007 |
| WO | 2008/022060 | 2/2008 |
| WO | 2010/019210 A2 | 2/2010 |
| WO | 2010/019210 A3 | 2/2010 |
| WO | 2010/025510 A1 | 3/2010 |
| WO | 2010/054403 A1 | 5/2010 |
| WO | 2010/075257 A1 | 7/2010 |
| WO | 2011/035143 A2 | 3/2011 |
| WO | 2011/163640 A1 | 12/2011 |
| WO | 2017/176620 A2 | 10/2017 |
| WO | 2017/176620 A3 | 10/2017 |

OTHER PUBLICATIONS

Extended European Search Report corresponding to EP 20160995.5 dated May 5, 2020; 8 pages.

International Search Report corresponding to PCT/US2009/068941 dated Mar. 5, 2010; 1 page.

International Preliminary Report on Patentability corresponding to PCT/US2009/068941 dated Jun. 29, 2011, 8 pages.

International Search Report corresponding to PCT/US2011/041910 dated Nov. 15, 2011, 1 page.

International Preliminary Report on Patentability corresponding to PCT/US2011/041910 dated Dec. 28, 2012, 8 pages.

International Search Report and Written Opinion corresponding to PCT Application No. PCT/US2015/052697 dated Jan. 7, 2016, 8 pages.

International Preliminary Report on Patentability corresponding to PCT/US2015/052697 dated Apr. 13, 2017, 6 pages.

International Search Report and Written Opinion corresponding to PCT Application No. PCT/US2021/064350 dated Mar. 16, 2022, 10 pages.

International Search Report and Written Opinion corresponding to PCT/US2017/013132 dated Apr. 7, 2017; 10 pages.

Abdellatif, A. A. et al, "True vasculitis in lupus nephritis," *Clinical Nephrology* (Aug. 2010; accepted in revised form Jan. 22, 2010); 74(2):106-112.

Aboab et al., "Emerging drugs for the treatment of sepsis," *Exp. Opin. Emerg. Drugs.* (10.1517/14728214.11.1.7 © 2006 Ashley Publications SSN 1472-8214); 11(1):7-22.

Alexander, Jessy John et al., "Contrasting roles for CR3 and C5aR in experimental immune complex-mediated glomerulonephritis," *Molecular Immunology* Abstract Only (Oct. 2014); 61(2):246 Abstract No. 083.

Alfaadhel, Talal et al., "Management of Membranous Nephropathy in Western Countries," *Kidney Dis* (Sep. 9, 2015) 1:126-137.

Allegretti, Marcello et al., "Allosteric Modulation of Chemoattractant Receptors," *Frontiers in Immunology* (May 2, 2016); vol. 7, Article 170; 9 pages.

Anonymous: "ChemoCentryx Rare Disease Drug as Effective as Standard of Care in Mid-Stage Study," Jan. 6, 2016, XP055606113, Retrieved from the Internet: URL:http://www.spjnews.com/2016/01/06/chemocentryx-rare-disease-drug-as-effective-as-standard-of-care-in-mid-stage-study/ [retrieved on Jul. 16, 2019]; 5 pages.

Anonymous: ChemoCentryx Reports Improvement in Renal Physiology and Stabilization of Kidney Function Following Treatment with Orally Administered Complement Inhibitor CCX168 (Avacopan) in Patient with Refractory C3 Glomerulopathy, Oct. 27, 2016, XP055606102, Retrieved from the Internet: URL:https://ir.chemocentryx.com/news-releases/news-release-details/ chemocentryx-reports-improvement-renal-physiology-and [retrieved on Jul. 16, 2019]; 5 pages.

Anonymous: "The human C5a receptor (hC5aR) antagonist CCX168 effectively ameliorates a model of ANCA glomerulonephritis (GN) in hc5aR Knock-in Mice;" Jan. 1, 2010, pp. 1-1, XP055603945, Retrieved from the Internet: URL:https://integrity.clarivate.com/integrity/xm1xs1/pk_ ref_list.xm1_show_ficha_ref?p_ref_id= 1562433 [retrieved on Jul. 9, 2019].

Anonymous: "Committee for Orphan Medicine Products (COMP) meeting report on the review of applications for orphan designation," *European Medicines Agency Committee for Orphan Medicine Products* (COMP) 162$^{nd}$ plenary meeting Dec. 9-11, 2014 (Dec. 12, 2014); 9 pages.

Anonymous: "Public summary of opinion on orphan designation (2R,3S)-2-(4-cyclopentylaminophenyl)-1-(2-fluoro-6-methylbenzoyl)piperidine-3-carboxylic acid(4-methyl-3-trifluoromethylphenyl)amide for the treatment of granulomatosis with polyangiitis," *European Medicines Agency Committee for Orphan Medicine Products* (COMP) (Jan. 12, 2015); ChemoCentryx Limited, London (sponsor); 5 pages.

Anonymous: "C3 Glomerulopathy: Dense Deposit Disease and C3 Glomerulonephritis," *National Organization of Rare Diseases (NORD)* [NORD gratefully acknowledges Richard JH Smith, MD, Director of the Iowa Institute of Human Genetics and the Molecular Otolaryngology and Renal Research Laboratories at the University of Iowa, for assistance in the preparation of this report.] Years published: 2005, 2010, 2013, 2015, 2018; rarediseases.org/rare-diseases/c3-glomerulopathy-dense-deposit-disease-and-c3-glomerulonephritis/; 9 pages.

Appel, Gerald B. et al., "Membranoproliferative Glomerulonephritis Type II (Dense Deposit Disease): An Update," *J Am Soc Nephrol* (2005) 16:1392-1404.

Ayala et al., "Differential induction of apoptosis in lymphoid tissues during sepsis: variation in onset, frequency and the nature of the mediators," *Blood* (May 15, 1996); 87:4261-4275.

Bao et al., "C5a promotes development of experimental lupus nephritis which can be blocked with a specific receptor antagonist," *Eur. J. Immunol.* (Accepted Jun. 20, 2005); 35:2496-2506.

Barbour, Thomas D., MD et al., "Dense Deposit Disease and C3 Glomerulopathy," Semin Nephrol (Nov. 2013) 33(6):493-507; document is 26 pages.

Barbour, Thomas D. et al., "Update on C3 glomerulopathy," *Nephrol Dial Transplant* (2016; Advance Access publication Oct. 17, 2014) 31:717-725.

Bekker, Pirow et al., "Characterization of Pharmacologic and Pharmacokinetic Properties of CCX168, a Potent and Selective Orally Administered Complement 5a Receptor Inhibitor, Based on Preclinical Evaluation and Randomized Phase 1 Clinical Study," *PLOS One* [DOI:10.1371/journal.pone.0164646 (Oct. 21, 2016); 19 pages.

Blagg et al., "Small, non-peptide C5a receptor antagonists: Part 1," *Bioorganic & Medicinal Chemistry Letters* (Aug. 31, 2008); 18:5601-5604.

Bomback, Andrew S. et al., "Eculizumab for Dense Deposit Disease and C3 Glomerulonephrt" *Clin J Am Soc Nephrol* (May 2012) 7:748-756.

Bomback, Andrew S. et al., "Pathogenesis of the C3 glomerulopathies and reclassification of MPGN," *Nature Reviews* (Nov. 2012) 8:634-642.

Braga et al., "Making crystals from crystals: a green route to crystal engineering and polymorphism," *The Journal of The Royal Society of Chemistry, Chem. Commun.* (Jun. 15, 2005), pp. 3635-3645.

(56) References Cited

OTHER PUBLICATIONS

Brodbeck; Robbin M et al., "Identification and Characterization of NDT 9513727 [N,N-bis(1,3-Benzodioxol-5-ylmethyl)-1-butyl-2,4-diphenyl-1 H-imidazole-5-methanamine], a Novel, Orally Bioavailable C5a Receptor Inverse Agonist," *The Journal of Pharmacology and Experimental Therapeutics* (2008; accepted Aug. 26, 2008); 327(3):898-909.
CAS Registry 1346623-17-3, also known as CCX168, copy of STN entry for registry number, accessed Mar. 31, 2018, 1 page (Year: 2018).
Chemcats (AN) 0078873838 (Jul. 29, 2011); one page.
ChemiCool "rotamer," (Sep. 9, 2012) one page.
Chronic-Obstructive-Pulmonary disease (COPD), Treatment Overview, www.webmd.com/lung/copd/tc/chronic-obstructive-pulmonary-disease-copd-treatme . . . p. 1-2, retrieved Apr. 22, 2014.
Covic, Adrian et al., "Epidemiology of renal disease in Romania: a 10 year review of two regional renal biopsy databases," *Nephrol Dial Transplant* (2006; Advance Access publication Oct. 25, 2005) 21:419-424.
Cravedi et al., "Immune Cell-Derived C3a and C5a Costimulate Human T Cell Alloimmunity" *Am. J. Transplant* (Jun. 27, 2013); 13(10):2530-2539.
Dairaghi D.J. et al., "Chemokine Receptor CCR3 Function Is Highly Dependent on Local pH and Ionic Strength," *The Journal of Biological Chemistry* (Nov. 7, 1997); 272(45):28206-28209.
Dairaghi D.J. et al., "HHV8-encoded vMIP-I selectively Engages Chemokine Receptor CCR8 Agonist and Antagonist Profiles of Viral Chemokines," *The Journal of Biological Chemistry*, (Jul. 30, 1999); 274(31):21569-21574.
Davis, T. Keefe, C3 Glomerulonephritis versus 'C3 Glomerulopathies?' *Kidneycentric* Paper 15. http://digitalcommons.wustl.edu/kidneycentricall/15. Reproduced with permission of the American Academy of Pediatrics, copyright 2016. 7 pages.
Dorwald, F. Zaragoza *Side Reactions in Organic Synthesis*, 2005, Wiley: VCH, Weinheim; p. IX of Preface pp. 1-15; 37 total pages.
Drugnews, "CCX168 ChemoCentryx Identifies C5a receptor antagonist GlaxoSmithKline milestone payment ChemoCentryx milestone payment," R & D Focus Drug News, May 2009, pp. 1-2, http://business.hgihbeam.com/436989/article-1G1-199837927/ccx-168-chemocentryx-identi . . . , retrieved Sep. 5, 2015.
Fakhouri, Fadi et al., "C3 glomerulopathy: a new classification," *Nat. Rev. Nephrol.* (Jul. 6, 2010) 6:494-499.
Foreman, K. E. et al., "C5a-induced expression of )selectin in endothelial cells," *J Clin Invest.* (1994; received for Public Feb. 14, 1994 and in revised form May 6, 1994) 94(3):1147-1155.
Figueres, Marie-Lucile et al., "Heterogeneous histologic and clinical evolution in 3 cases of dense deposit disease with long-term follow-up," *Human Pathology* (2014; accepted Jul. 23, 2014) 45:2326-2333.
Gerber B. O. et al., "An Activation Switch in the Ligand Binding Pocket of the C5a Receptor," *The Journal of Biological Chemistry* (Feb. 2, 2001); 276(5):3394-3400.
Guan, Li Ping et al., "Synthesis and Anticonvulsant Activity of 5-Phenyl-[1,2,4]-triazolo[4,3-a]quinolones," *Arch. Pharm. Chem. Life Sci.* (2008; accepted Jul. 30, 2008); 341:774-779.
Gurkan, Md, Sevgi et al. "Eculizumab and Recurrent C3 Glomerulonephritis," *Pediatr Nephrol.* (Oct. 31, 2013) 28(10):1975-1981.
Horiuchi, Takahiko et al., "Complement-targeted therapy: development of C5- and C5a-targed inhibition," *Inflammation and Regeneration* (published online Jun. 3, 2016); 36(11): 1-6.
Hou, Jean et al., "Toward a working definition of C3 glomerulopathy by immunofluorescence," *Kidney International* (2014; published online Sep. 25, 2013) 85:450-456.
Hu et al., "Small molecules in treatment of sepsis," *Current Drug Targets*, (Feb. 2011; DOI:10.2174/138945011794182737); 12:256-262.
Huber-Lang et al., "Protection of innate immunity by C5aR antagonist in septic mice," *The FASEB Journal* (Oct. 2002; accepted Jun. 26, 2002) 16:1567-1574.

Huber-Lang et al., "Role of Complement in Multi-Organ Dysfunction Syndrome," *The Complement System, Abstract*, (@ 2004; Print/DOI: 10.1007/1-4020-8056-5_22); pp. 465-480.
Høgåsen, K et al., "Hereditary porcine membranoproliferative glomerulonephritis type II is caused by factor H deficiency." *J Clin Invest.* (1995; received for publication Jun. 8, 1994 and in revised form Nov. 7, 1994) 95(3):1054-1061.
"Improper Markush," (Feb. 9, 2011); Fed. Registry 76(27):7162-7175, slide 1, 64-67.
Inflammation, Wikipedia, https://en.wikipedia.org/wiki/inflammation (retrieved Sep. 7, 2015); 30 pages.
"Ischemia-reperfusion injury in vascular disease," Sebastian de la Fuente, Apr. 2009, 54 pages.
Jayne et al., "Oral C5A Receptor Antagonist CCX168 Phase 2 Clinical Trial in ANCA-Associated Renal Vasculitis", *Ann Rheum Dis* (2014; DOI 10.1136/annrheumdis-2014-eular.3728); 73(2):148.
Kumar et al., "Cell-derived anaphylatoxins as key mediators of antibody-dependent type II autoimmunity in mice," *J. Clin. Invest.*, (Feb. 2006; accepted in revised form Nov. 15, 2005); 116(2):512-520.
Kusner et al., "Effect of complement and its regulation on myasthenia gravis pathogenesis," *Expert Rev. Clin. Immunol.* (Jan. 2008; doi:10.1586/1744666X.4.1.43); 4(1):43-52.
Lachmann, P. J. et al., "Taking Complement to the Clinic—has the Time Finally Come?," *Scandinavian Journal of Immunology* (pub online Apr. 1, 2009); 69:471-478.
Lally, Lindsay et al., "Current Therapies for ANCA-Associated Vasculitis," *Annu. Rev. Med.* (2015; first published online Oct. 17, 2014); 66:227-240.
Lee, Hyun et al., "Receptors for complement C5a. The importance of C5aR and the enigmatic role of C5L2," *Immunol. Cell Biol.* (published online Jan. 29, 2008); 86(2):153-160.
Le Quintrec, Moglie, M.D., Ph.D., "Eculluzumab for Treatment of Rapidly Progressive C3 Glomerulopathy," *Am J Kidney Dis.* (2015; originally published on-line Dec. 16, 2014); 65(3):484-489.
Lupus Nephritis Definition Wikipedia https://en.wikipedia.org/wiki/Lupus_nephritis (May 26, 2017); 3 pages.
March, Darren R. et al., "Potent Cyclic Antagonists of the Complement C5a Receptor on Human Polymorphonuclear Leukocytes. Relationships between Structures and Activity," *Molecular Pharmacology* (2004; accepted Jan. 7, 2004); 65(4):868-879.
McGrogan, Anita et al., "The incidence of primary glomerulonephritis worldwide: a systematic review of the literature," *Nephrol Dial Transplant* (2011; Advance Access publication Nov. 10, 2010) 26:414-430.
Medjeral-Thomas, Nicholas R. et al., "C3 Glomerulopathy: Clinicopathologic Features and Predictors of Outcome," *Clin J Am Soc Nephrol* (Jan. 2014; accepted Sep. 3, 2013) 9:46-53.
MedlinePlus "Sepsis," (Apr. 5, 2012); 3 pages.
Mizuno et al., "Novel C5a regulators in inflammatory disease," *Exp. Opin. Investig. Drugs* (Jul. 15, 2005);14(7):807-821.
Monk, P.N. et al., "Function, structure and therapeutic potential of complement C5a receptors," *British Journal of Pharmacology* (Jul. 2, 2007); 152:429-448.
Nichols, Eva-Maria et al., "An extended mini-complement factor H molecule ameliorates experimental C3 glomerulopathy," *Kidney International* (Jul. 29, 2015) 88:1314-1322.
Nikforovich et al., "Modeling Molecular Mechanisms of Binding of the Anaphylatoxin C5 to the C5a Receptor," *Biochemistry* (Jan. 11, 2008); 47:3117-3130.
Noël, Romain, et al., "Synthesis of New Chiral 6-Carbonyl 2,3,8,8a-Tetrahydro-7H-oxazolo[3,2- α]pyridines," *J. Org. Chem.* (Oct. 1, 2005); 70(22):9044-9047.
Noël, Romain, et al., "Diastereoselective Reduction of Bicyclic B-Enamino Carbonyl Piperidines—Application to the Total Syntehsis of (-)-Deoocassine," *Eur. J. Org. Chem.* (2007; published online Nov. 17, 2006 DOI: 10.1002/ejoc.200600777); 476-486.
Noël, Romain, et al., "Convenient One-Pot Synthesis of Chiral Tetrahydropyridines via a Multicomponent Reaction," *Synthesis* (2008; advanced online publication May 16, 2008); 12:1948-1954.
Noris, Marina et al., "Glomerular Diseases Dependent on Complement Activation, Including Atypical Hemolytic Uremic Syndrome,

(56) References Cited

OTHER PUBLICATIONS

Membranoproliferative Glomerulonephritis, and C3 Glomerulopathy: Core Curriculum 2015," *Am J Kidney Dis.* (Aug. 1, 2015) 66(2):359-375.
Osoda, Tsutomu et al., "2D-Qsar for 450 types of amino acid induction peptides with a novel substructure pair descriptor having wider scope," *Journal of Cheminformatics* (Nov. 2, 2011);3:50; 9 pages.
Paczkowski et al., "Pharmacological characterization of antagonists of the C5a receptor," *British J. of Pharmacology* (Sep. 13, 1999); 128:1461-1466.
Penfold M.E.T. et al., "Cytomegalovirus encodes a potent a chemokine," *Proc. Natl. Acad. Sci. USA* (Aug. 1999; rec'd for review Apr. 20, 1999); 96:9839-9844.
Pickering, M. C. et al., "Prevention of C5 activation ameliorates spontaneous and experimental glomerulonephritis in factor H-deficient mice," *PNAS* (Jun. 20, 2006) 103(25):9649-9654.
Pickering, Matthew C. et al., "Uncontrolled C3 activation causes membranoproliferative glomerulonephritis in mice deficient in complement factor H," *Nature Genetics* (Aug. 2002; published online Jul. 1, 2002) 31:424-428.
Pickering, Mathew C. et al., "CE glomerulopathy: consensus report," *Kidney International* (Oct. 30, 2013) 84:1079-1089.
Powers, Larry J. et al., "Effect of Structural Change on Acute Toxicity and Antiinflammatory Activity in a Series of Imidazothiazoles and Thiazolobenzimidazoles," *Journal of Medicine Chemistry* (Jan. 1, 1981) 24(5):604-609.
Press Release: ChemoCentryx Announces Presentation of Positive Results from Phase II ANCA-Associated Vasculitis CLEAR Trial of Orally Administered Complement 5a Receptor Inhibitor CCX168 at the 53$^{rd}$ ERA-EDTA Congress (May 23, 2016); 5 pages.
Press Release: ChemoCentryx Announces Presentation of Positive Data from Ongoing Pilot Phase II Trial of CCX168 (Avacopan) in Atypical Hemolytic Uremic Syndrome (AHUS) at ASN Kidney Week 2016 (Oct. 17, 2016); 3 pages.
Press Release: ChemoCentryx Granted EU Orphan Drug Designation for CCX168, an Orally Administered Complement C5a Receptor Inhibitor, for the Treatment of Microscopic Polyangiitis and Granulomatosis with Polyangiitis, Two Forms of ANCA-Associated Vasculitis (Dec. 4, 2014); 4 pages.
Proctor, Lavinia M. et al., "Recent development in C5/C5a inhibitors," *Expert Opinion on Therapeutic Patents* (Mar. 24, 2006); 16(4):445-458.
PubChem-CID-58506549; Create date Aug. 19, 2012, p. 3 Fig.
PubChem-CID-58506538; Create date Aug. 19, 2012, p. 3, Fig.
PubChem-CID-68717675; Create date Nov. 30, 2012, p. 3, Fig.
PubChem-CID-68607180; Create date Nov. 30, 2012, p. 3, Fig.
Qu et al., "Recent developments in low molecular weight complement inhibitors," *Molecular Immun.* (Aug. 28, 2009); 47:185-195.
Rheumatoid Arthritis Definition *Johns Hopkins Arthritis Center* https://www.hopkinsarthritis.org/arthritis-info/rheumatoid-arthritis/ra-treatment/ (May 26, 2017); 3 pages.
Ricklin, Daniel et al., "Complement-targeted therapeutics," *Nature Biotechnology* (pub online Nov. 7, 2007); 25(11):1265-1275.
Ricklin, Daniel et al., "Complement in immune and inflammatory disorders: therapeutic interventions," *J. Immunol.* (Apr. 15, 2013); 190(8):3839-3847).
Riedemann et al., "The enigma of sepsis," *The Journal of Clinical Investigation* (Aug. 15, 2003); 112(4):460-467.
Rittirsch et al., "Harmful molecular mechanisms in sepsis," *Nat. Rev. Immunol.* (Oct. 2008; DOI: 10.1038/nri2402); 8(10):776-787. RN 1348614-10-7 Database:GVK BIO (2011).
Salvadori, Maurizio et al., "Reclassification of membranoproliferative glomerulonephritis: Identification of a new GN: C3GN," *World J Nephrol* (Jul. 6, 2016) 5(4):308-320.
Sarma et al., "New developments in C5a receptor signaling," *Cell Health Cytoskelet.* (Jul. 31, 2012); 4:73-82.

Schraufstatter, Ingrid U. et al., "Complement C3a and C5a Induce Different Signal Transduction Cascades in Endothelial Cells," *J Immunol* (2002; accepted for pblication Jun. 19, 2002) 169:2102-2110.
Schreiber, Adrian et al., "C5a Receptor Mediates Neutrophil Activation and NCA-Induced Glomerulonephritis," *J Am Soc Nephrol* (2009; accepted Sep. 5, 2008) 20:289-298.
Seddon, "Pseudopolymorph: A Polemic," *Crystal Growth & Design* (Jul. 26, 2004); 4(6):1087.
Servais, Aude et al., "Primary glomerulonephritis with isolated C3 deposits: a new entity which shares common genetic risk factors with haemolytic uraemic syndrome," *J Med Genet* (2007; published online Oct. 3, 2006) 44:193-199.
Seth, Sanjeev, MD, PhD et al., "Membranoproliferative Glomerulonephritis: Pathogenetic Heterogeneity and Proposal for a New Classification," *Semin Nephrol* (Jul. 2011) 31(4):341-348; document is 14 pages.
Short et al., "Effects of a new C5a receptor antagonist on C5a- and endotoxin-induced neutropenia in the rat," *British J. Pharma.* (1999; accepted Nov. 5, 1998); 125:551-554.
Short, Anna J. et al., "Response-selective C5a agonists: differential effects on neutropenia and hypotension in the rat," *British J. Pharma* (1999; accepted Jul. 21, 1999); 128:511-514.
Siciliano, Salvatore J. et al., "Two-site binding of C5a by its receptor: An alternative binding paradigm for G protein-coupled receptors," *Proc. Natl. Acad. Sci. USA* (Feb. 1994; communicated by E. Scolnick Oct. 20, 1993); 91:1214-1218.
Smith, Richard J. H. et al., "New Approaches to the Treatment of Dense Deposit Disease," *J Am Soc Nephrol* (2007) 18:2447-2456.
Smith, Richard J. H. et al., "Review; Dense deposit disease;" *Molecular Immunology* (Aug. 2011); 48(14):1604-1610; document is 19 pages.
Sridharan, Vellaisamy et al., "A Very Efficient Cerium(IV) Ammonium Nitrate Catalyzed, Four-Component Synthesis of Tetrahydropyridines and Its Application in the Concise Generation of Functionalized Homoquinolizine Frameworks," *Chem Eur. J.* (published online Mar. 13, 2009; DOI:10.1002/CHEM.200900044); 15;4565-4572.
Strachan Anna J. et al., "A New Small Molecule C5a Receptor Antagonist Inhibits the Reverse-Passive Arthus Reaction and Endotoxic Shock in Rats," *The Journal of Immunology*, (Apr. 6, 2000); 164:6560-6565.
Sumichika Hiroshi et al., "Identification of a Potent and Orally Active Non-peptide C5a Receptor Antagonist," *The Journal of Biological Chemistry*, Dec. 20, 2002, vol. 277, No. 51, pp. 49403-49407.
Swaminathan, Sundararaman et al., "Changing Incidence of Glomerular Disease in Olmsted County, Minnesota: A 30-Year Renal Biopsy Study," *Clin J Am Soc Nephrol* (2006; accepted Mar. 1, 2006) 1:483-487.
Taylor, Stephen M. et al., "Development of response-selective agonists of human C5a anaphylatoxin: conformational, biological, and therapeutic considerations," *Current Med. Chem.*, (@ 2001 Bentham Science Publishers Ltd); 8:675-684.
Thomas, S. et al., "Current concepts in C3 glomerulopathy," *Indian J. Nephrol.* (Nov.-Dec. 2014) 24(6):339-348.
Tiebosch, Anton T.M.G. et al., "Epidemiology of idiopathic glomerular disease: A prospective study," *Kidney International* (Jan. 29, 1987) 32:112-116.
"Chapter 6: Treatment of Acute Rejection," *American Journal of Transplantation* (Sep. 24, 2009); 9(3):S21-S22.
Unsinger, Jacqueline et al., "Sepsis-induced human lymphocyte apoptosis and cytokine production in "humanized" mice," *Journal of Leukocyte Biology* (Aug. 2009; accepted Mar. 16, 2009); 86: 219-227.
Vendemia, F. et al., "Epidemiology of primary glomerulonephritis in the elderly. Report from the Italian Registry of Renal Biopsy," *J Nephrol.* (Sep.-Oct. 2001) 14(5):340-52. Abstract only.
Vivarelli M. et al. "Treatment of C3 Glomerulopathy with Complement Blockers," *Seminars in Thrombosis & Hemostasis* (May 5, 2014) 40(4):472-477.

(56) References Cited

OTHER PUBLICATIONS

Ward, "Role of the complement in experimental sepsis," *Journal of Leukocyte Biology*, (Mar. 2008; published online Sep. 17, 2007); 83:467-470.
Ward, "The Harmful Role of C5a on Innate Immunity in Sepsis," *J. Innate Immun.* (Jun. 26, 2010); 2:439-445.
Ward et al., "The dark side of C5a in sepsis," *Nature Reviews* (Feb. 2004); 4:133-142.
Warren, "Mouse models to study sepsis syndrome in humans" *J. Leukocyte Biol.* (Apr. 15, 2009); 86:199-200.
Welte, Thomas et al., "Treating C3 glomerulopathy with eculizumab." *BMC Nephrology* (Dec. 1, 2018) 197:7; pp. 1-10.
Wetmore, James B. et al., "The incidence, prevalence, and outcomes of glomerulonephritis derived from a large retrospective analysis," *Kidney International* (published online Jul. 15, 2016) 90:853-860.
Woltering, Thomas J. et al., "Synthesis and characterization of 1,3-dihydro-benzo[b][1,4]diazepin-2-one derivatives: Part 4. In vivo active potent and selective non-competitive metabotropic glutamate receptor 2/3 antagonists," *Bioorganic & Medicine Chemistry Letters* (Dec. 1, 2010) 20:6969-6974.
Woodruff et al., "Species dependence for binding of small molecule agonist and antagonists to the C5a receptor on polymorphonuclear leukocytes," *Inflammation* (2001; DOI:10.1023/A:1011036414353); 25(3):171-177.
Woodruff T.M. et al., "A Potent Human C5a Receptor Antagonist Protects against Disease Pathology in a Rat Model of Inflammatory Bowel Disease," *The Journal of Immunology* (Nov. 15, 2003); 171:5514-5520.
Wygnaarden et al., Textbook of medicine, 16th Edition, @1983, p. 247.
Xiao et al.,"C5a Receptor (CD88) Blockade Protects against MPO-ANCA GN," *J. Am. Soc. Nephrol.* (2014; accepted for publication Aug. 5, 2013); 25(2):225-231.
Xiao, Xu et al., "C3 Glomerulopathy: The Genetic and Clinical Findings in Dense Deposit Disease and C3 Glomerulonephritis," *Semin Throm Hemost* (May 5, 2014) 40:465-471.
Yan et al., "New insights for C5a and C5a receptors in sepsis," *Frontiers in Immunology* (Dec. 10, 2012); 3(368):1-15.
Yatime, Laure et al., "Structural basis for the targeting of complement anaphylatoxin C5a using a mixed L-RNA/L-DNA aptamer," *Nature Communications* (Apr. 22, 2015); 13 pages.
Extended European Search Report corresponding to EP 21206901.7 dated May 6, 2022; 7 pages.
Horig, Heidi et al., "From bench to clinic and back: Perspective on the 1st IQPC Translational Research conference," *Journal of Translational Medicine*, (Dec. 20, 2004) 2:44; 8 pages.
Mahmoud, Aysam et al., "C3 Glomerulopathy and Therapeutic Potential of C5 Complement Inhibitors," *Open Journal of Nephrology* (Mar. 28, 2016) 6:10-16.
National Kidney Foundation: Treatment for C3G—https://www.kidney.org/atoz/content/treatment-c3g#:~:text=There%20are%20no%20medicines%20that,the%20body's%20defense%20against%20infections) Accessed and downloaded Jun. 26, 2023; 1 page.
Schafer, Stefan et al., "Failure is an option: learning from unsuccessful proof-of-concept trials," *Drug Discovery Today* (Nov. 2008) 13(21/22): 913-916.

Figure 1 represents the patient's Estimated glomerular filtration rate (eGFR) before and after treatment with compound 1.
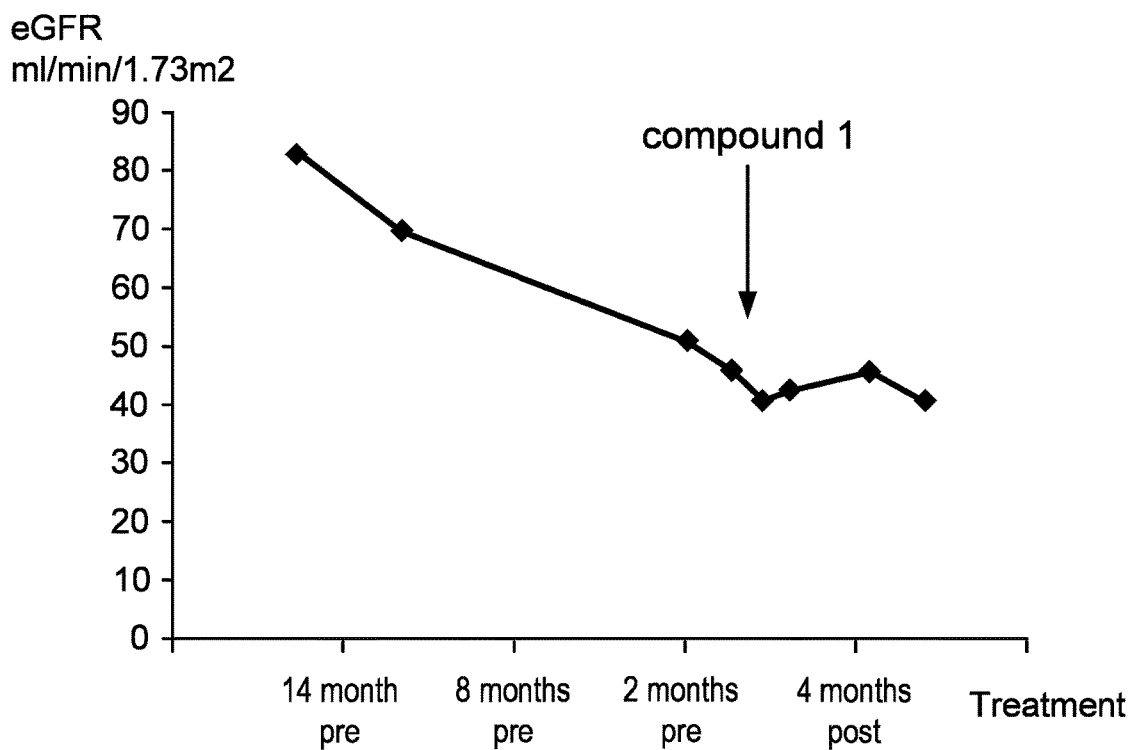
Figure 2 represents the histopathological improvement following treatment with compound 1.
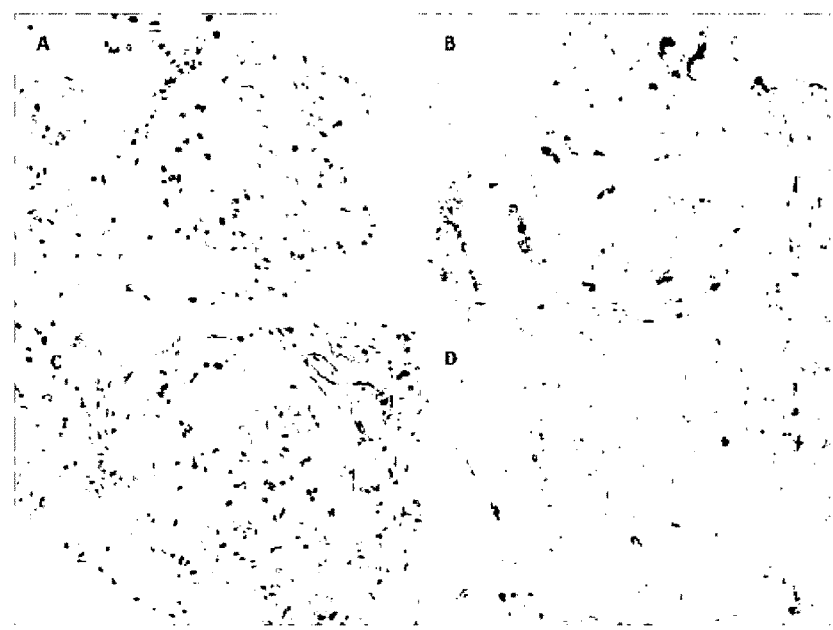

METHOD OF TREATING C3 GLOMERULOPATHY

CROSS-REFERENCES TO RELATED APPLICATIONS

This application is a continuation of U.S. patent application Ser. No. 16/184,535 filed Nov. 8, 2018, which application is a continuation of U.S. patent application Ser. No. 15/404,610 filed Jan. 12, 2017 (abandoned), which application claims priority benefit under 35 U.S.C. § 119(e) of U.S. Provisional Application No. 62/278,788 filed Jan. 14, 2016; U.S. Provisional Application No. 62/280,346 filed Jan. 19, 2016; U.S. Provisional Application No. 62/347,450 filed Jun. 8, 2016; and U.S. Provisional Application No. 62/397,527 filed Sep. 21, 2016, each of which is herein incorporated by reference in its entirety for all purposes.

STATEMENT AS TO RIGHTS TO INVENTIONS MADE UNDER FEDERALLY SPONSORED RESEARCH AND DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

C3 glomerulopathy (C3G) is a rare disease of the kidney (the prevalence of C3G is estimated at 2-3 per 1,000,000 people). C3G is characterized by deposition of the protein known as C3 (a component of the body's complement system) in the filtration units (the glomeruli) of the kidney, indicating complement involvement in causing kidney damage. C3 glomerulopathy is characterized by evidence of alternative complement activation based on C3 deposition in the glomeruli. There are two forms of the disease: dense deposit disease (DDD, formerly called membranoproliferative glomerulonephritis [MPGN] Type II) and C3 glomerulonephritis (C3GN, formerly called idiopathic MPGN). Genetic lesions leading to defective complement regulation, including mutations in complement factor H (CFH) have been described in these patients. Patients with C3 glomerulopathy often have high proteinuria and progressive deterioration in renal function. There is no approved treatment for patients with C3 glomerulopathy, including C3GN. Without treatment, C3G invariably leads to kidney failure, and kidney transplant is frequently the only option. Even after transplantation, the new kidney will frequently fail due to recurrence of the disease.

BRIEF SUMMARY OF THE INVENTION

The present disclosure is directed to a method of treating a human suffering from or susceptible to C3 glomerulopathy comprising administering to the human an effective amount of a C5aR antagonist.

In one embodiment, the C5aR antagonist is a compound having the formula (I), or a pharmaceutically acceptable salt thereof,

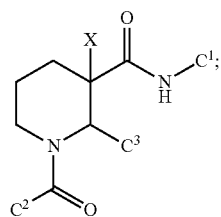

(I)

wherein
  $C^1$ is phenyl optionally substituted with from 1 to 3 $R^1$ substituents;
  $C^2$ is phenyl optionally substituted with from 1 to 3 $R^2$ substituents;
  $C^3$ is selected from the group consisting of $C_{3-8}$ cycloalkyl and phenyl, and each $C^3$ is optionally substituted with from 1-3 $R^3$ substituents;
  each $R^1$ is independently selected from the group consisting of
    halogen, —CN, —CO$_2$R$^a$, —CONR$^a$R$^b$, —C(O)R$^a$, —OC(O)NR$^a$R$^b$, —NR$^b$C(O)R$^a$, —NR$^b$C(O)$_2$R$^c$, —NR$^a$C(O)NR$^a$R$^b$, —NR$^a$R$^b$, —OR$^a$, and —S(O)$_2$NR$^a$R$^b$; wherein each R$^a$ and R$^b$ is independently selected from hydrogen, $C_{1-8}$ alkyl, and $C_{1-8}$ haloalkyl, or when attached to the same nitrogen atom can be combined with the nitrogen atom to form a five or six-membered ring having from 0 to 2 additional heteroatoms as ring members selected from N, O or S; each R$^c$ is independently selected from the group consisting of $C_{1-8}$ alkyl, $C_{1-8}$ haloalkyl, $C_{3-6}$ cycloalkyl, heterocycloalkyl, aryl and heteroaryl, and wherein the aliphatic and cyclic portions of R$^a$, R$^b$ and R$^c$ are optionally further substituted with from one to three halogen, hydroxy, methyl, amino, alkylamino and dialkylamino groups; and optionally when two $R^1$ substituents are on adjacent atoms, are combined to form a fused five or six-membered carbocyclic ring;
  each $R^2$ is independently selected from the group consisting of
    halogen, —CN, —R$^f$, —CO$_2$R$^d$, —CONR$^d$R$^e$, —C(O)R$^d$, —OC(O)NR$^d$R$^e$, —NR$^e$C(O)R$^d$, —NR$^e$C(O)$_2$R$^f$, —NR$^d$C(O)NR$^d$R$^e$, —NR$^d$C(O)NR$^d$R$^e$, —NR$^d$R$^e$, —OR$^d$, and —S(O)$_2$NR$^d$R$^e$; wherein each R$^d$ and R$^e$ is independently selected from hydrogen, $C_{1-8}$ alkyl, and $C_{1-8}$ haloalkyl, or when attached to the same nitrogen atom can be combined with the nitrogen atom to form a five or six-membered ring having from 0 to 2 additional heteroatoms as ring members selected from N, O or S; each R$^f$ is independently selected from the group consisting of $C_{1-8}$ alkyl, $C_{1-8}$ haloalkyl, $C_{3-6}$ cycloalkyl, heterocycloalkyl, aryl and heteroaryl, and wherein the aliphatic and cyclic portions of R$^d$, R$^e$ and R$^f$ are optionally further substituted with from one to three halogen, hydroxy, methyl, amino, alkylamino and dialkylamino groups;
  each $R^3$ is independently selected from the group consisting of
    halogen, —CN, —CO$_2$R$^g$, —CONR$^g$R$^h$, —C(O)R$^g$, —OC(O)NR$^g$R$^h$, —NR$^h$C(O)R$^g$, —NR$^h$C(O)$_2$R$^i$, —NR$^g$C(O)NR$^g$R$^h$, —NR$^g$R$^h$, —OR$^g$, —S(O)$_2$NR$^g$R$^h$, —X$^4$—R$^j$, —X$^4$—NR$^g$R$^h$, —X$^4$—CONR$^g$R$^h$, —X$^4$—NR$^h$C(O)R$^g$, —NHR$^j$ and —NHCH$_2$R$^j$, wherein X$^4$ is a C$_{1-4}$ alkylene; each R$^g$ and R$^h$ is independently selected from hydrogen, C$_{1-8}$ alkyl, C$_{3-6}$ cycloalkyl and C$_{1-8}$haloalkyl, or when attached to the same nitrogen atom can be combined with the nitrogen atom to form a five or six-membered ring having from 0 to 2 additional heteroatoms as ring members selected from N, O or S and is optionally substituted with one or two oxo; each R$^i$ is independently selected from the group consisting of C$_{1-8}$ alkyl, C$_{1-8}$ haloalkyl, C$_{3-6}$ cycloalkyl, heterocycloalkyl, aryl and heteroaryl; and each is selected from the group consisting of C$_{3-6}$ cycloalkyl, pyrrolinyl, piperidinyl, morpholinyl, tetrahydrofuranyl, and tetrahydropyranyl, and wherein the aliphatic and cyclic portions of R$^g$, R$^h$, R$^i$ and R$^j$ are optionally further substituted with from one to three halogen, methyl, CF$_3$, hydroxy, amino, alkylamino and dialkylamino groups; and X is hydrogen or CH$_3$.

In some embodiments, the C5aR antagonist is a compound having the formula:

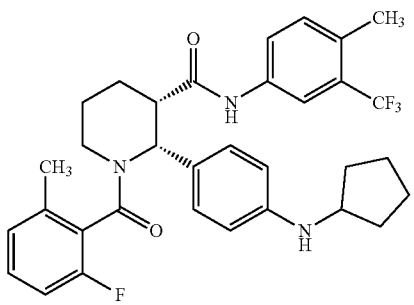

BRIEF DESCRIPTION OF THE DRAWINGS

FIG. 1 represents the patient's Estimated glomerular filtration rate (eGFR) before and after treatment with compound 1.

FIG. 2 represents the histopathological improvement following treatment with compound 1.

DETAILED DESCRIPTION OF THE INVENTION

Abbreviation and Definitions

The term "alkyl", by itself or as part of another substituent, means, unless otherwise stated, a straight or branched chain hydrocarbon radical, having the number of carbon atoms designated (i.e. C$_{1-8}$ means one to eight carbons). Examples of alkyl groups include methyl, ethyl, n-propyl, isopropyl, n-butyl, t-butyl, isobutyl, sec-butyl, n-pentyl, n-hexyl, n-heptyl, n-octyl, and the like. The term "alkenyl" refers to an unsaturated alkyl group having one or more double bonds. Similarly, the term "alkynyl" refers to an unsaturated alkyl group having one or more triple bonds. Examples of such unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "cycloalkyl" refers to hydrocarbon rings having the indicated number of ring atoms (e.g., C$_{3-6}$cycloalkyl) and being fully saturated or having no more than one double bond between ring vertices. "Cycloalkyl" is also meant to refer to bicyclic and polycyclic hydrocarbon rings such as, for example, bicyclo[2.2.1]heptane, bicyclo[2.2.2]octane, etc. The term "heterocycloalkyl" refers to a cycloalkyl group that contain from one to five heteroatoms selected from N, O, and S, wherein the nitrogen and sulfur atoms are optionally oxidized, and the nitrogen atom(s) are optionally quaternized. The heterocycloalkyl may be a monocyclic, a bicyclic or a polycyclic ring system. Non limiting examples of heterocycloalkyl groups include pyrrolidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-oxide, piperazine, pyran, pyridone, 3-pyrroline, thiopyran, pyrone, tetrahydrofuran, tetrahydrothiophene, quinuclidine, and the like. A heterocycloalkyl group can be attached to the remainder of the molecule through a ring carbon or a heteroatom.

The term "alkylene" by itself or as part of another substituent means a divalent radical derived from an alkane, as exemplified by —CH$_2$CH$_2$CH$_2$CH$_2$—. Typically, an alkyl (or alkylene) group will have from 1 to 24 carbon atoms, with those groups having 10 or fewer carbon atoms being preferred in the present disclosure. A "lower alkyl" or "lower alkylene" is a shorter chain alkyl or alkylene group, generally having four or fewer carbon atoms. Similarly, "alkenylene" and "alkynylene" refer to the unsaturated forms of "alkylene" having double or triple bonds, respectively.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, and —CH=CH—N(CH$_3$)—CH$_3$. Up to two heteroatoms may be consecutive, such as, for example, —CH$_2$—NH—OCH$_3$ and —CH$_2$—O—Si(CH$_3$)$_3$. Similarly, the terms "heteroalkenyl" and "heteroalkynyl" by itself or in combination with another term, means, unless otherwise stated, an alkenyl group or alkynyl group, respectively, that contains the stated number of carbons and having from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group.

The term "heteroalkylene" by itself or as part of another substituent means a divalent radical, saturated or unsaturated or polyunsaturated, derived from heteroalkyl, as exemplified by —CH$_2$—CH$_2$—S—CH$_2$CH$_2$— and —CH$_2$—S—CH$_2$—CH$_2$—NH—CH$_2$—, —O—CH$_2$—CH=CH—, —CH$_2$—CH=C(H)CH$_2$—O—CH$_2$— and —S—CH$_2$—C≡C—. For heteroalkylene groups, heteroatoms can also occupy either or both of the chain termini (e.g., alkyleneoxy, alkylenedioxy, alkyleneamino, alkylenediamino, and the like).

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. Additionally, for dialkylamino groups, the alkyl portions can be the same or different and can also be combined to form a 3-7 membered ring with the nitrogen atom to which each is attached. Accordingly, a group represented as —NR$^a$R$^b$ is meant to include piperidinyl, pyrrolidinyl, morpholinyl, azetidinyl and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "$C_{1-4}$ haloalkyl" is mean to include trifluoromethyl, 2,2,2-trifluoroethyl, 4-chlorobutyl, 3-bromopropyl, and the like.

The term "aryl" means, unless otherwise stated, a polyunsaturated, typically aromatic, hydrocarbon group which can be a single ring or multiple rings (up to three rings) which are fused together or linked covalently. The term "heteroaryl" refers to aryl groups (or rings) that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl groups include phenyl, naphthyl and biphenyl, while non-limiting examples of heteroaryl groups include pyridyl, pyridazinyl, pyrazinyl, pyrimindinyl, triazinyl, quinolinyl, quinoxalinyl, quinazolinyl, cinnolinyl, phthalaziniyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like).

The above terms (e.g., "alkyl," "aryl" and "heteroaryl"), in some embodiments, will include both substituted and unsubstituted forms of the indicated radical. Preferred substituents for each type of radical are provided below. For brevity, the terms aryl and heteroaryl will refer to substituted or unsubstituted versions as provided below, while the term "alkyl" and related aliphatic radicals is meant to refer to unsubstituted version, unless indicated to be substituted.

Substituents for the alkyl radicals (including those groups often referred to as alkylene, alkenyl, alkynyl and cycloalkyl) can be a variety of groups selected from: -halogen, —OR', —NR'R", —SR', —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R", —NR'S(O)$_2$R", —CN and —NO$_2$ in a number ranging from zero to (2 m'+1), where m' is the total number of carbon atoms in such radical. R', R" and R"' each independently refer to hydrogen, unsubstituted $C_{1-8}$ alkyl, unsubstituted heteroalkyl, unsubstituted aryl, aryl substituted with 1-3 halogens, unsubstituted $C_{1-8}$ alkyl, $C_{1-8}$ alkoxy or $C_{1-8}$ thioalkoxy groups, or unsubstituted aryl-$C_{1-4}$ alkyl groups. When R' and R" are attached to the same nitrogen atom, they can be combined with the nitrogen atom to form a 3-, 4-, 5-, 6-, or 7-membered ring. For example, —NR'R" is meant to include 1-pyrrolidinyl and 4-morpholinyl. The term "acyl" as used by itself or as part of another group refers to an alkyl radical wherein two substituents on the carbon that is closest to the point of attachment for the radical is replaced with the substituent =O (e.g., —C(O)CH$_3$, —C(O)CH$_2$CH$_2$OR' and the like).

Similarly, substituents for the aryl and heteroaryl groups are varied and are generally selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R"', —NH—C(NH$_2$)=NH, —NR'C(NH$_2$)=NH, —NH—C(NH$_2$)=NR', —S(O)R', —S(O)$_2$R', —S(O)$_2$NR'R", —NR'S(O)$_2$R", —N$_3$, perfluoro($C_1$-$C_4$)alkoxy, and perfluoro($C_1$-$C_4$)alkyl, in a number ranging from zero to the total number of open valences on the aromatic ring system; and where R', R" and R"' are independently selected from hydrogen, $C_{1-8}$ alkyl, $C_{3-6}$ cycloalkyl, $C_{2-8}$ alkenyl, $C_{2-8}$ alkynyl, unsubstituted aryl and heteroaryl, (unsubstituted aryl)-$C_{1-4}$ alkyl, and unsubstituted aryloxy-$C_{1-4}$ alkyl. Other suitable substituents include each of the above aryl substituents attached to a ring atom by an alkylene tether of from 1-4 carbon atoms.

Two of the substituents on adjacent atoms of the aryl or heteroaryl ring may optionally be replaced with a substituent of the formula —T—C(O)—(CH$_2$)$_q$—U—, wherein T and U are independently —NH—, —O—, —CH$_2$— or a single bond, and q is an integer of from 0 to 2.

Alternatively, two of the substituents on adjacent atoms of the aryl or heteroaryl ring may optionally be replaced with a substituent of the formula -A-(CH$_2$)$_r$—B—, wherein A and B are independently —CH$_2$—, —O—, —NH—, —S—, —S(O)—, —S(O)$_2$—, —S(O)$_2$NR' or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted $C_{1-6}$ alkyl.

As used herein, the term "heteroatom" is meant to include oxygen (O), nitrogen (N), sulfur (S) and silicon (Si).

The term "ionic liquid" refers to any liquid that contains mostly ions. Preferably, in the present disclosure, "ionic liquid" refers to the salts whose melting point is relatively low (e.g., below 250° C.). Examples of ionic liquids include but are not limited to 1-butyl-3-methylimidazolium tetrafluoroborate, 1-hexyl-3-methylimidazolium tetrafluoroborate, 1-octyl-3-methylimidazolium tetrafluoroborate, 1-nonyl-3-methylimidazolium tetrafluoroborate, 1-decyl-3-methylimidazolium tetrafluoroborate, 1-hexyl-3-methylimidazolium hexafluorophosphate and 1-hexyl-3-methylimidazolium bromide, and the like.

As used herein, the term "treating" or "treatment" encompasses both disease-modifying treatment and symptomatic treatment, either of which may be prophylactic (i.e., before the onset of symptoms, in order to prevent, delay or reduce the severity of symptoms) or therapeutic (i.e., after the onset of symptoms, in order to reduce the severity and/or duration of symptoms). Treatment methods provided herein include, in general, administration to a patient an effective amount of one or more compounds provided herein. Suitable patients include those patients suffering from or susceptible to {i.e., prophylactic treatment) a disorder or disease identified herein. Typical patients for treatment as described herein include mammals, particularly primates, especially humans. Other suitable patients include domesticated companion animals such as a dog, cat, horse, and the like, or a livestock animal such as cattle, pig, sheep and the like.

The term "pharmaceutically acceptable salts" is meant to include salts of the active compounds which are prepared with relatively nontoxic acids or bases, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science*, 1977, 66, 1-19). Certain specific compounds of the present disclosure contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present disclosure.

The compounds described in the Embodiments below can be obtained according to methods described in WO 2010/075257, WO 2011/163640 and WO 2016/053890.

EMBODIMENTS

The present disclosure is directed to a method of treating a human suffering from or susceptible to complement 3 glomerulopathy comprising administering to the human an effective amount of a compound having the formula (I), or a pharmaceutically acceptable salt thereof,

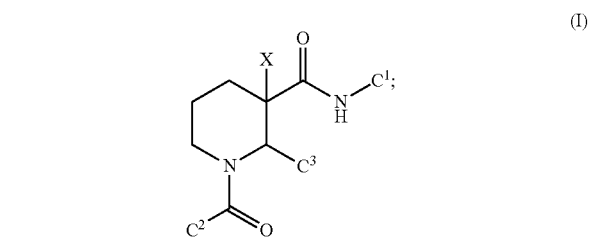

wherein
$C^1$ is phenyl optionally substituted with from 1 to 3 $R^1$ substituents;
$C^2$ is phenyl optionally substituted with from 1 to 3 $R^2$ substituents;
$C^3$ is selected from the group consisting of $C_{3-8}$ cycloalkyl and phenyl, and each $C^3$ is optionally substituted with from 1-3 $R^3$ substituents;
each $R^1$ is independently selected from the group consisting of
halogen, —CN, —$R^c$, —$CO_2R^a$, —$CONR^aR^b$, —C(O)$R^a$, —OC(O)$NR^aR^b$, —$NR^bC(O)R^a$, —$NR^bC(O)_2R^c$, —$NR^aC(O)NR^aR^b$, —$OR^a$, and —$S(O)_2NR^aR^b$; wherein each $R^a$ and $R^b$ is independently selected from hydrogen, $C_{1-8}$ alkyl, and $C_{1-8}$ haloalkyl, or when attached to the same nitrogen atom can be combined with the nitrogen atom to form a five or six-membered ring having from 0 to 2 additional heteroatoms as ring members selected from N, O or S; each $R^c$ is independently selected from the group consisting of $C_{1-8}$ alkyl, $C_{1-8}$ haloalkyl, $C_{3-6}$ cycloalkyl, heterocycloalkyl, aryl and heteroaryl, and wherein the aliphatic and cyclic portions of $R^a$, $R^b$ and $R^c$ are optionally further substituted with from one to three halogen, hydroxy, methyl, amino, alkylamino and dialkylamino groups; and optionally when two $R^1$ substituents are on adjacent atoms, are combined to form a fused five or six-membered carbocyclic ring;
each $R^2$ is independently selected from the group consisting of
halogen, —CN, —$R^f$, —$CO_2R^d$, —$CONR^dR^e$, —C(O)$R^d$, —OC(O)$NR^dR^e$, —$NR^eC(O)R^d$, —$NR^eC(O)_2R^f$, —$NR^dC(O)NR^dR^e$, —$NR^dC(O)NR^dR^e$, —$NR^dR^e$, —$OR^d$, and —$S(O)_2NR^dR^e$; wherein each $R^d$ and $R^e$ is independently selected from hydrogen, $C_{1-8}$ alkyl, and $C_{1-8}$ haloalkyl, or when attached to the same nitrogen atom can be combined with the nitrogen atom to form a five or six-membered ring having from 0 to 2 additional heteroatoms as ring members selected from N, O or S; each $R^f$ is independently selected from the group consisting of $C_{1-8}$ alkyl, $C_{1-8}$ haloalkyl, $C_{3-6}$ cycloalkyl, heterocycloalkyl, aryl and heteroaryl, and wherein the aliphatic and cyclic portions of $R^d$, $R^e$ and $R^f$ are optionally further substituted with from one to three halogen, hydroxy, methyl, amino, alkylamino and dialkylamino groups;

each $R^3$ is independently selected from the group consisting of halogen, —CN, —$R^i$, —$CO_2R^g$, —$CONR^gR^h$, —$C(O)R^g$, —$OC(O)NR^gR^h$, —$NR^hC(O)R^g$, —$NR^hC(O)_2R^i$, —$NR^gC(O)NR^gR^h$, —$NR^gR^h$, —$OR^g$, —$S(O)_2NR^gR^h$, —$X^4$—$R^j$, —$X^4$—$NR^gR^h$, —$X^4$—$CONR^gR^h$, —$X^4$—$NR^hC(O)R^g$, —$NHR^j$ and —$NHCH_2R^j$, wherein $X^4$ is a $C_{1-4}$ alkylene; each $R^g$ and $R^h$ is independently selected from hydrogen, $C_{1-8}$ alkyl, $C_{3-6}$ cycloalkyl and $C_{1-8}$ haloalkyl, or when attached to the same nitrogen atom can be combined with the nitrogen atom to form a five or six-membered ring having from 0 to 2 additional heteroatoms as ring members selected from N, O or S and is optionally substituted with one or two oxo; each $R^i$ is independently selected from the group consisting of $C_{1-8}$ alkyl, $C_{1-8}$ haloalkyl, $C_{3-6}$ cycloalkyl, heterocycloalkyl, aryl and heteroaryl; and each $R^j$ is selected from the group consisting of $C_{3-6}$ cycloalkyl, pyrrolinyl, piperidinyl, morpholinyl, tetrahydrofuranyl, and tetrahydropyranyl, and wherein the aliphatic and cyclic portions of $R^g$, $R^h$, $R^i$ and $R^j$ are optionally further substituted with from one to three halogen, methyl, $CF_3$, hydroxy, amino, alkylamino and dialkylamino groups; and X is hydrogen or $CH_3$.

In some embodiments, the compound has the formula (Ia):

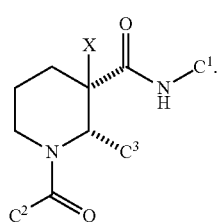

(Ia)

In some embodiments, the compound has the formula (Ib):

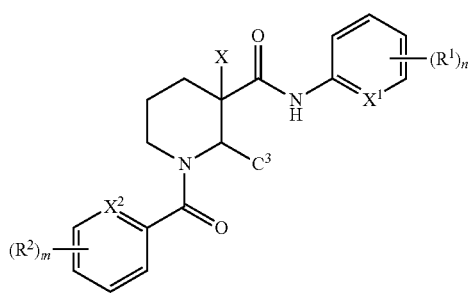

Ib wherein
$X^1$ is selected from the group consisting of CH and $CR^1$;
the subscript n is an integer of from 0 to 2;
$X^2$ is selected from the group consisting of CH and $CR^2$; and
the subscript m is an integer of from 0 to 2.

In some embodiments, the compound has the formula (Ic):

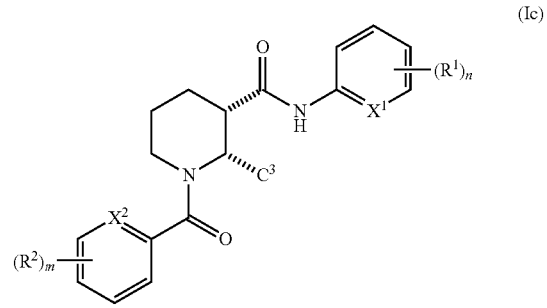

(Ic)

wherein
$X^1$ is selected from the group consisting of CH and $CR^1$;
the subscript n is an integer of from 0 to 2;
$X^2$ is selected from the group consisting of CH and $CR^2$; and
the subscript m is an integer of from 0 to 2.

In some embodiments, the compound has the formula (Id):

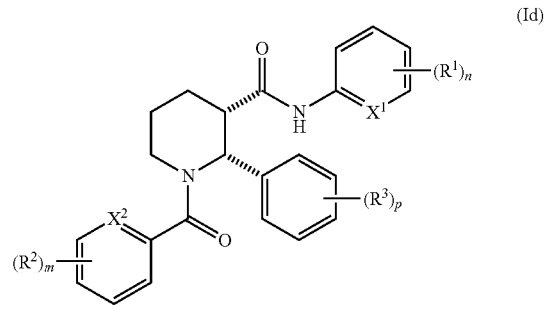

(Id)

wherein
the subscript p is an integer of from 0 to 3;
$X^1$ is selected from the group consisting of CH and $CR^1$;
the subscript n is an integer of from 0 to 2;
$X^2$ is selected from the group consisting of CH and $CR^2$; and
the subscript m is an integer of from 0 to 2.

In some embodiments, the compound has the formula (Ie):

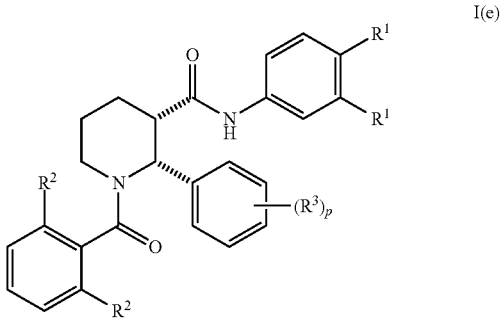

I(e)

wherein p is 0, 1 or 2.

In some embodiments, the compound is selected from the group consisting of
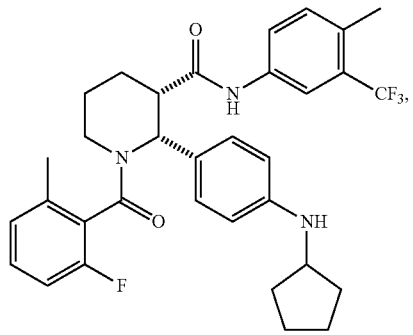
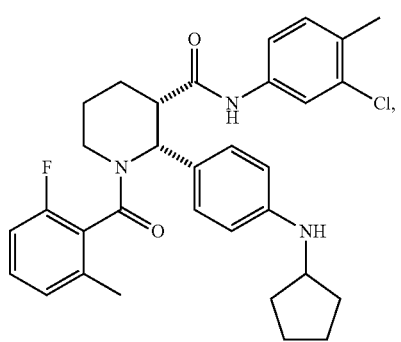
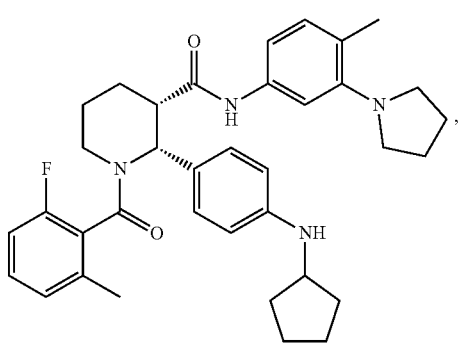
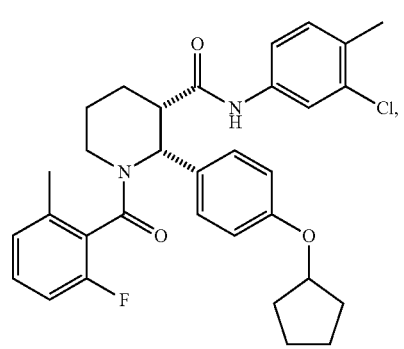
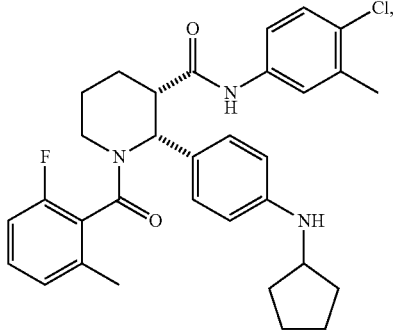
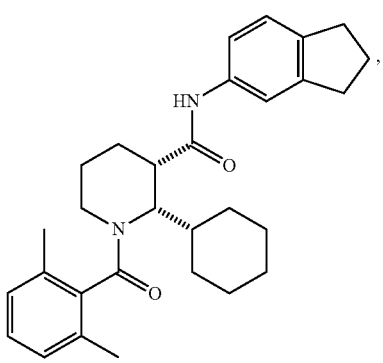
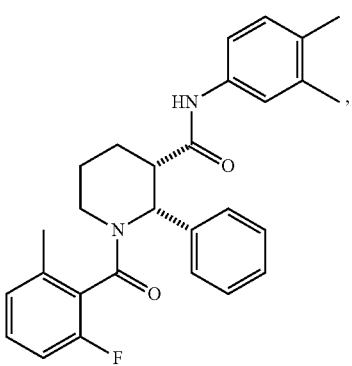
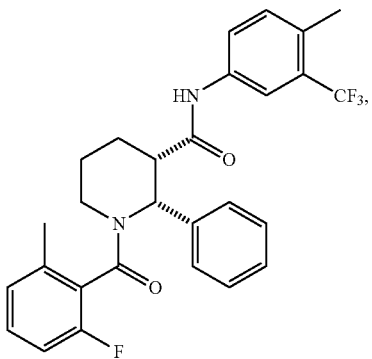

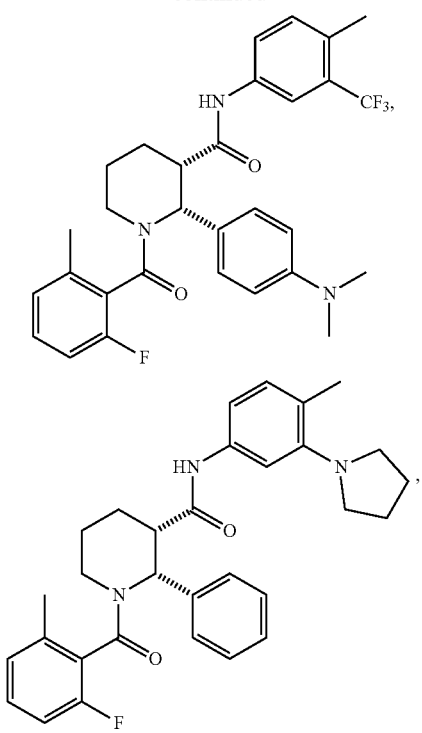
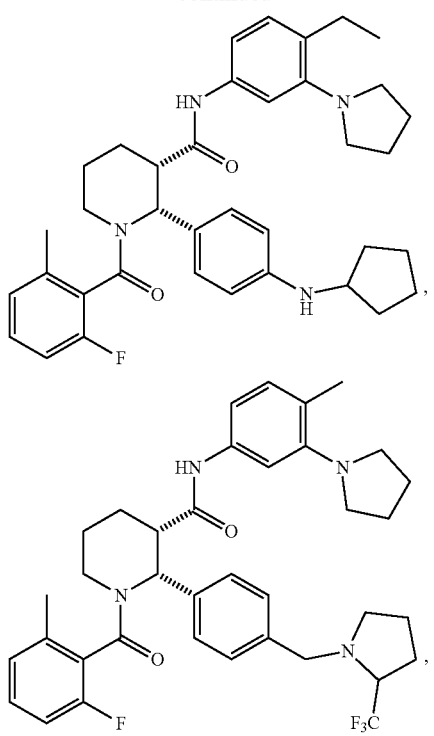
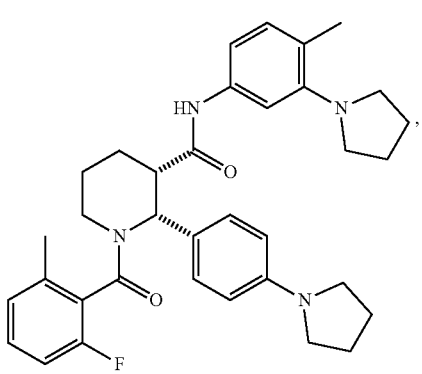
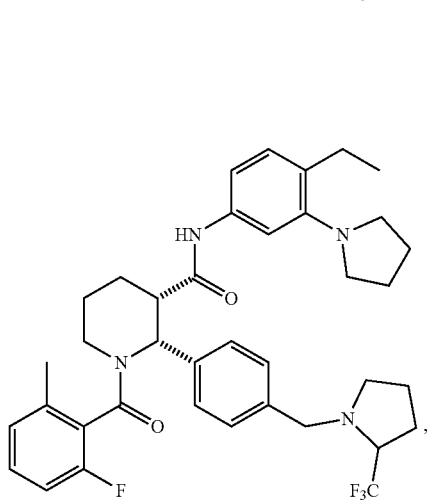
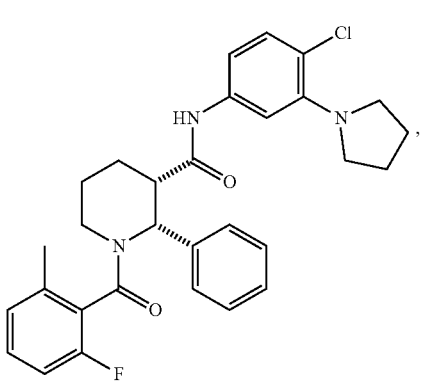
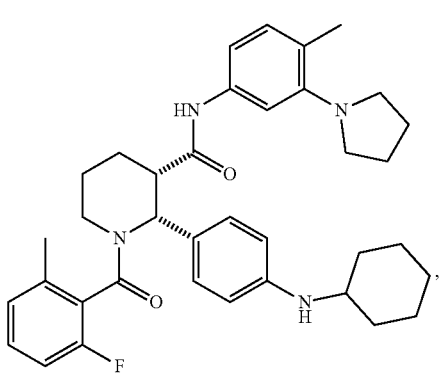

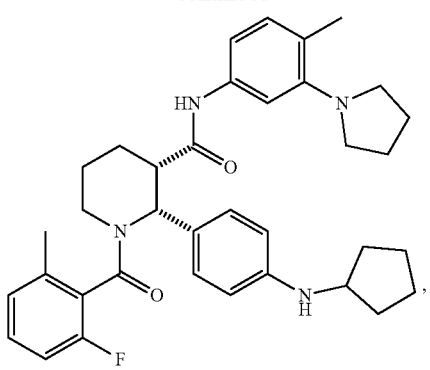
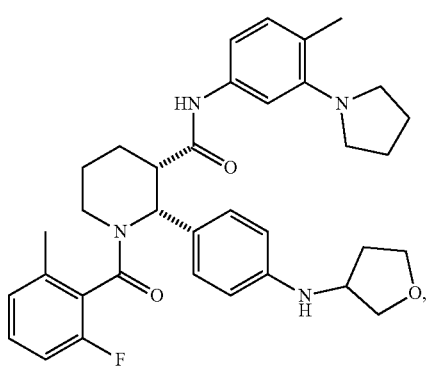
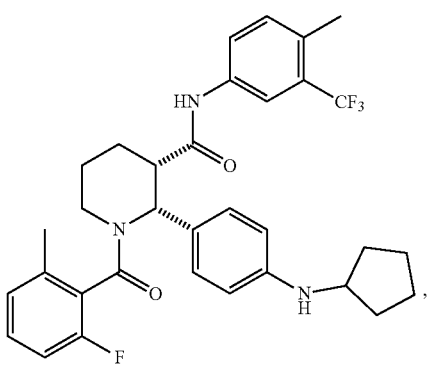
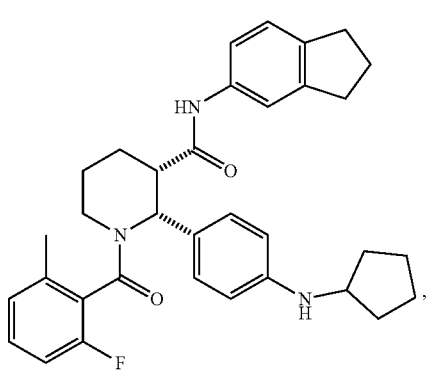
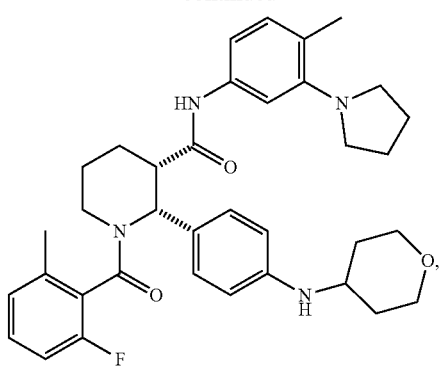
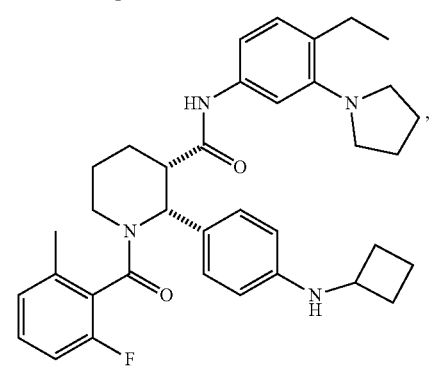
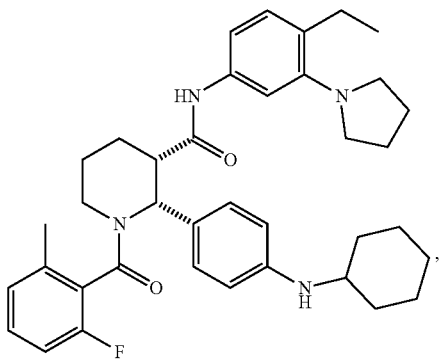
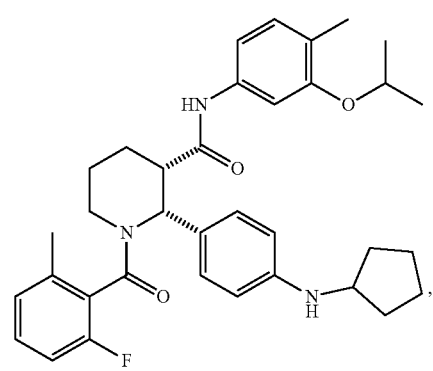

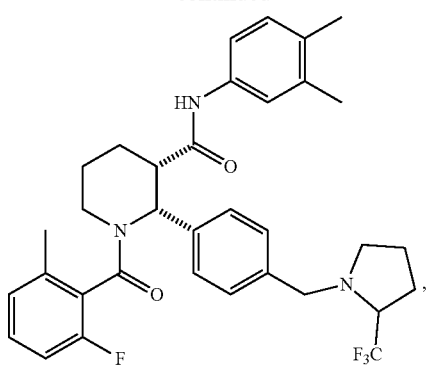
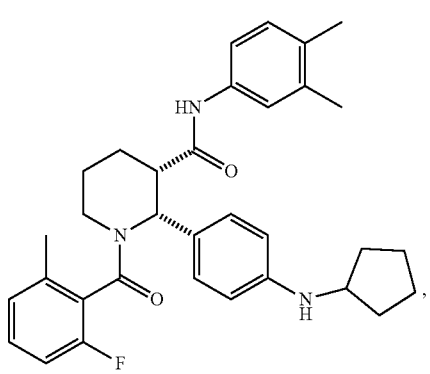
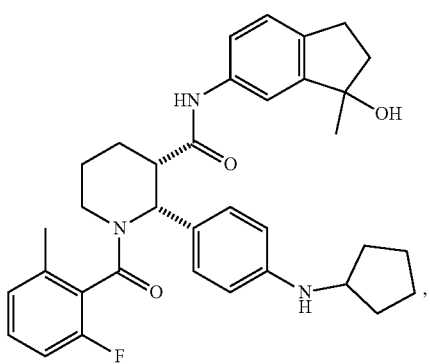
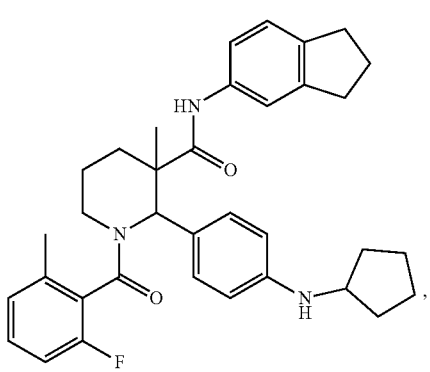
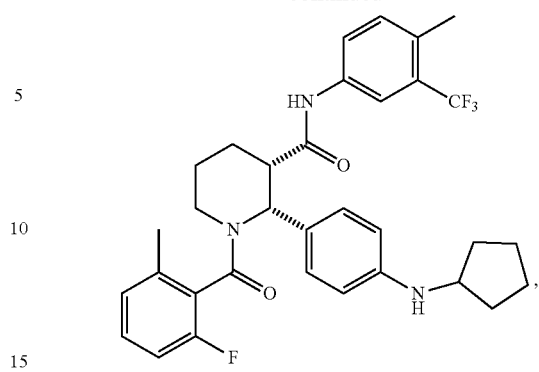
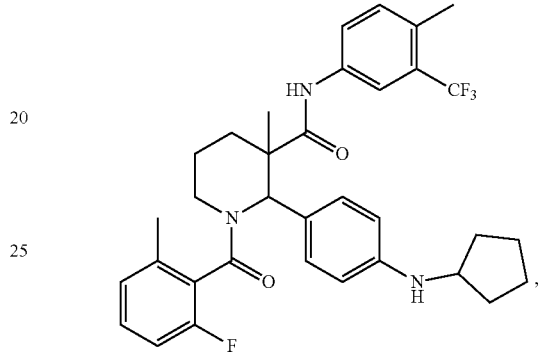
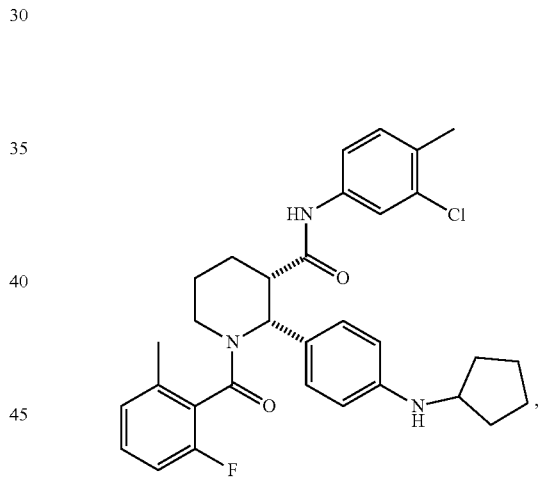
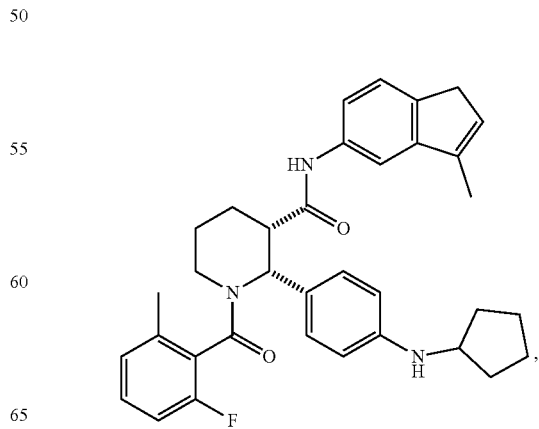

-continued

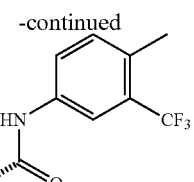

and

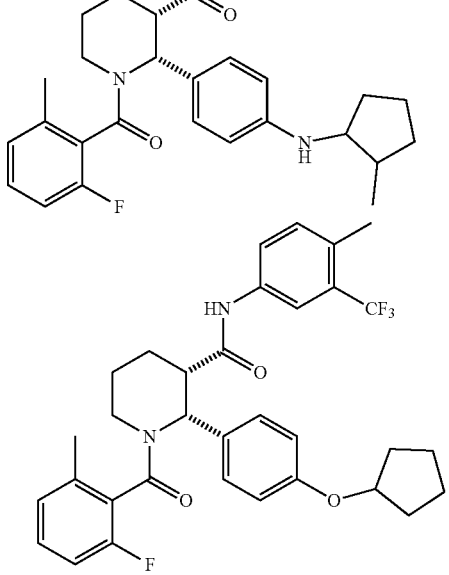

or a pharmaceutically acceptable salt thereof.

In some embodiments, the compound is

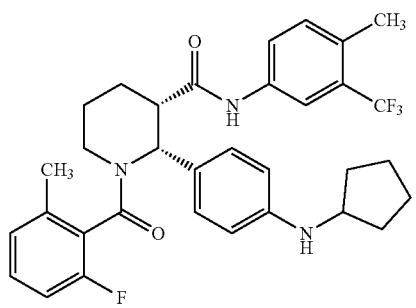 [SMILES: Cc1ccc(NC(=O)[C@H]2CCCN(C(=O)c3c(C)cccc3F)[C@H]2c2ccc(NC3CCCC3)cc2)cc1C(F)(F)F]

or a pharmaceutically acceptable salt thereof.

A method of slowing the rate of decline in Estimated Glomerular Filtration Rate (eGFR) in a human suffering from or susceptible to C3 glomerulopathy is provided comprising administering to the human an effective amount of a compound having the formula (I), or a pharmaceutically acceptable salt thereof,

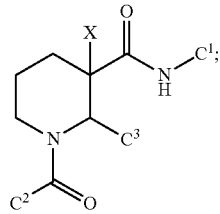

(I)

wherein
$C^1$ is phenyl optionally substituted with from 1 to 3 $R^1$ substituents;
$C^2$ is phenyl optionally substituted with from 1 to 3 $R^2$ substituents;
$C^3$ is selected from the group consisting of $C_{3-8}$ cycloalkyl and phenyl, and each $C^3$ is optionally substituted with from 1-3 $R^3$ substituents;
each $R^1$ is independently selected from the group consisting of
halogen, —CN, —$R^c$, —$CO_2R^a$, —$CONR^aR^b$, —C(O)$R^a$, —OC(O)$NR^aR^b$, —$NR^bC(O)R^a$, —$NR^bC(O)_2R^c$, —$NR^aC(O)NR^aR^b$, —$OR^1$, and —$S(O)_2NR^aR^b$; wherein each $R^a$ and $R^b$ is independently selected from hydrogen, $C_{1-8}$ alkyl, and $C_{1-8}$ haloalkyl, or when attached to the same nitrogen atom can be combined with the nitrogen atom to form a five or six-membered ring having from 0 to 2 additional heteroatoms as ring members selected from N, O or S; each $R^c$ is independently selected from the group consisting of $C_{1-8}$ alkyl, $C_{1-8}$ haloalkyl, $C_{3-6}$ cycloalkyl, heterocycloalkyl, aryl and heteroaryl, and wherein the aliphatic and cyclic portions of $R^a$, $R^b$ and $R^c$ are optionally further substituted with from one to three halogen, hydroxy, methyl, amino, alkylamino and dialkylamino groups; and optionally when two $R^1$ substituents are on adjacent atoms, are combined to form a fused five or six-membered carbocyclic ring;
each $R^2$ is independently selected from the group consisting of
halogen, —CN, —$R^f$, —$CO_2R^d$, —$CONR^dR^e$, —C(O)$R^d$, —OC(O)$NR^dR^e$, —$NR^eC(O)R^d$, —$NR^eC(O)_2R^f$, —$NR^dC(O)NR^dR^e$, —$NR^dC(O)NR^dR^e$, —$NR^dR^e$, —$OR^d$, and —$S(O)_2NR^dR^e$; wherein each $R^d$ and $R^e$ is independently selected from hydrogen, $C_{1-8}$ alkyl, and $C_{1-8}$ haloalkyl, or when attached to the same nitrogen atom can be combined with the nitrogen atom to form a five or six-membered ring having from 0 to 2 additional heteroatoms as ring members selected from N, O or S; each $R^f$ is independently selected from the group consisting of $C_{1-8}$ alkyl, $C_{1-8}$ haloalkyl, C3-6 cycloalkyl, heterocycloalkyl, aryl and heteroaryl, and wherein the aliphatic and cyclic portions of $R^d$, $R^e$ and $R^f$ are optionally further substituted with from one to three halogen, hydroxy, methyl, amino, alkylamino and dialkylamino groups;
each $R^3$ is independently selected from the group consisting of
halogen, —CN, —$R^i$, —$CO_2R^g$, —$CONR^gR^h$, —C(O)$R^g$, —OC(O)$NR^gR^h$, —$NR^hC(O)R^g$, —$NR^hC(O)_2R^i$, —$NR^gC(O)NR^gR^h$, —$NR^gR^h$, —$OR^g$, —$S(O)_2NR^gR^h$, —$X^4$—$R^j$, —$X^4$—$NR^gR^h$, —$X^4$—$CONR^gR^h$, —$X^4$—$NR^hC(O)R^g$, —$NHR^j$ and —$NHCH_2R^j$, wherein $X^4$ is a $C_{1-4}$ alkylene; each $R^g$ and $R^h$ is independently selected from hydrogen, $C_{1-8}$ alkyl, $C_{3-6}$ cycloalkyl and $C_{1-8}$haloalkyl, or when attached to the same nitrogen atom can be combined with the nitrogen atom to form a five or six-membered ring having from 0 to 2 additional heteroatoms as ring members selected from N, O or S and is optionally substituted with one or two oxo; each $R^i$ is independently selected from the group consisting of $C_{1-8}$ alkyl, $C_{1-8}$ haloalkyl, $C_{3-6}$ cycloalkyl, heterocycloalkyl, aryl and heteroaryl; and each $R^j$ is selected from the group consisting of $C_{3-6}$ cycloalkyl, pyrrolinyl, piperidinyl, morpholinyl, tetrahydrofuranyl, and tetrahydropyranyl, and wherein the aliphatic and cyclic portions of $R^g$, $R^h$, $R^i$ and $R^j$ are optionally further substituted with from one to three halogen, methyl, $CF_3$, hydroxy, amino, alkylamino and dialkylamino groups; and X is hydrogen or $CH_3$.

In some embodiments, the compound has the formula (Ie):

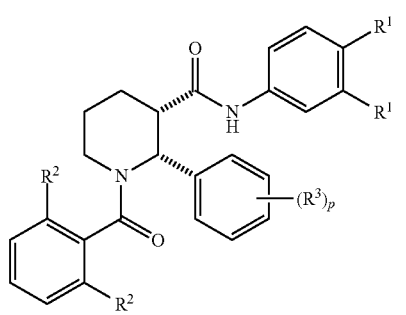

I(e)

wherein p is 0, 1 or 2.

In some embodiments, the compound is

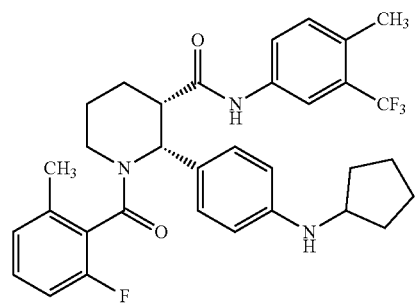 [SMILES: Cc1ccc(NC(=O)[C@H]2CCCN(C(=O)c3c(C)cccc3F)[C@H]2c2ccc(NC3CCCC3)cc2)cc1C(F)(F)F]

or a pharmaceutically acceptable salt thereof.

A method of reducing glomerular inflammation in a human suffering from or susceptible to C3 glomerulopathy is provided comprising administering to the human an effective amount of a compound having the formula (I), or a pharmaceutically acceptable salt thereof,

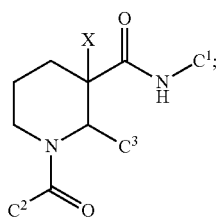

(I)

wherein
- $C^1$ is phenyl optionally substituted with from 1 to 3 $R^1$ substituents;
- $C^2$ is phenyl optionally substituted with from 1 to 3 $R^2$ substituents;
- $C^3$ is selected from the group consisting of $C_{3-8}$ cycloalkyl and phenyl, and each $C^3$ is optionally substituted with from 1-3 $R^3$ substituents;

each $R^1$ is independently selected from the group consisting of
halogen, —CN, —$R^c$, —$CO_2R^a$, —$CONR^aR^b$, —C(O)$R^a$, —OC(O)$NR^aR^b$, —$NR^bC(O)R^a$, —$NR^bC(O)_2R^c$, —$NR^aC(O)NR^aR^b$, —$OR^a$, and —$S(O)_2NR^aR^b$; wherein each $R^a$ and $R^b$ is independently selected from hydrogen, $C_{1-8}$ alkyl, and $C_{1-8}$ haloalkyl, or when attached to the same nitrogen atom can be combined with the nitrogen atom to form a five or six-membered ring having from 0 to 2 additional heteroatoms as ring members selected from N, O or S; each $R^c$ is independently selected from the group consisting of $C_{1-8}$ alkyl, $C_{1-8}$haloalkyl, $C_{3-6}$ cycloalkyl, heterocycloalkyl, aryl and heteroaryl, and wherein the aliphatic and cyclic portions of $R^a$, $R^b$ and $R^c$ are optionally further substituted with from one to three halogen, hydroxy, methyl, amino, alkylamino and dialkylamino groups; and optionally when two $R^1$ substituents are on adjacent atoms, are combined to form a fused five or six-membered carbocyclic ring;

each $R^2$ is independently selected from the group consisting of
halogen, —CN, —$R^f$, —$CO_2R^d$, —$CONR^dR^e$, —C(O)$R^d$, —OC(O)$NR^dR^e$, —$NR^eC(O)R^d$, —$NR^eC(O)_2R^f$, —$NR^dC(O)NR^dR^e$, —$NR^dC(O)NR^dR^e$, —$NR^dR^e$, —$OR^d$, and —$S(O)_2NR^dR^e$; wherein each $R^d$ and $R^e$ is independently selected from hydrogen, $C_{1-8}$ alkyl, and $C_{1-8}$ haloalkyl, or when attached to the same nitrogen atom can be combined with the nitrogen atom to form a five or six-membered ring having from 0 to 2 additional heteroatoms as ring members selected from N, O or S; each $R^f$ is independently selected from the group consisting of $C_{1-8}$ alkyl, $C_{1-8}$haloalkyl, $C_{3-6}$ cycloalkyl, heterocycloalkyl, aryl and heteroaryl, and wherein the aliphatic and cyclic portions of $R^d$, $R^e$ and $R^f$ are optionally further substituted with from one to three halogen, hydroxy, methyl, amino, alkylamino and dialkylamino groups;

each $R^3$ is independently selected from the group consisting of
halogen, —CN, —$R^i$, —$CO_2R^g$, —$CONR^gR^h$, —C(O)$R^g$, —OC(O)$NR^gR^h$, —$NR^hC(O)R^g$, —$NR^hC(O)_2R^i$, —$NR^gC(O)NR^gR^h$, —$NR^gR^h$, —$OR^g$, —$S(O)_2NR^gR^h$, —$X^4$—$R^j$, —$C^4$—$NR^gR^h$, —$X^4$—$CONR^gR^h$, —$X^4$—$NR^hC(O)R^g$, —$NHR^j$ and —$NHCH_2R^j$, wherein $X^4$ is a $C_{1-4}$ alkylene; each $R^g$ and $R^h$ is independently selected from hydrogen, $C_{1-8}$ alkyl, $C_{3-6}$ cycloalkyl and $C_{1-8}$ haloalkyl, or when attached to the same nitrogen atom can be combined with the nitrogen atom to form a five or six-membered ring having from 0 to 2 additional heteroatoms as ring members selected from N, O or S and is optionally substituted with one or two oxo; each $R^i$ is independently selected from the group consisting of $C_{1-8}$ alkyl, $C_{1-8}$ haloalkyl, $C_{3-6}$ cycloalkyl, heterocycloalkyl, aryl and heteroaryl; and each is selected from the group consisting of $C_{3-6}$ cycloalkyl, pyrrolinyl, piperidinyl, morpholinyl, tetrahydrofuranyl, and tetrahydropyranyl, and wherein the aliphatic and cyclic portions of $R^g$, $R^h$, $R^i$ and $R^j$ are optionally further substituted with from one to three halogen, methyl, $CF_3$, hydroxy, amino, alkylamino and dialkylamino groups; and X is hydrogen or $CH_3$.

In some embodiments, the compound has the formula (Ie):

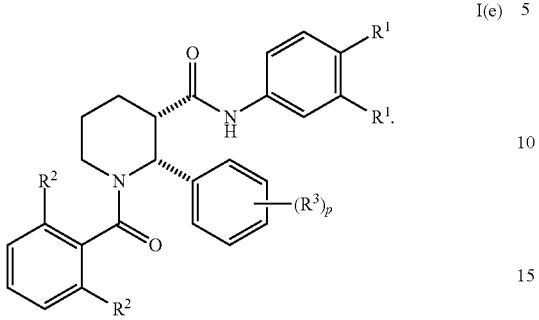

In some embodiments, the compound is

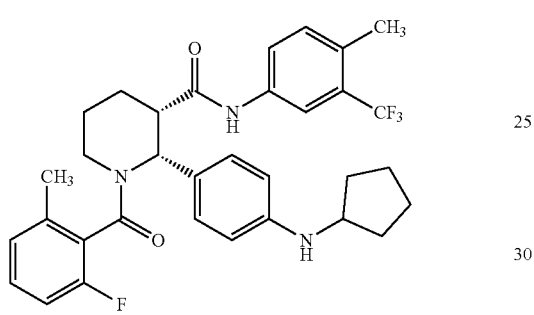

or a pharmaceutically acceptable salt thereof.

A method of reducing C3 deposits and/or C5b-9 deposits in a human suffering from or susceptible to C3 glomerulopathy is provided comprising administering to the human an effective amount of a compound having the formula (I), or a pharmaceutically acceptable salt thereof,

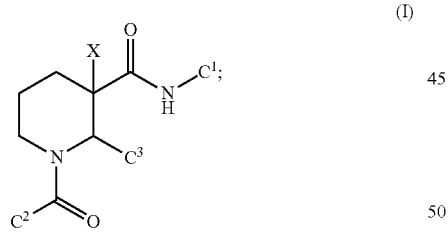

wherein
$C^1$ is phenyl optionally substituted with from 1 to 3 $R^1$ substituents;
$C^2$ is phenyl optionally substituted with from 1 to 3 $R^2$ substituents;
$C^3$ is selected from the group consisting of $C_{3-8}$ cycloalkyl and phenyl, and each $C^3$ is optionally substituted with from 1-3 $R^3$ substituents;
each $R^1$ is independently selected from the group consisting of
halogen, —CN, —$R^c$, —$CO_2R^a$, —$CONR^aR^b$, —C(O)$R^a$, —OC(O)$NR^aR^b$, —$NR^bC(O)R^a$, —$NR^bC(O)_2R^c$, —$NR^aC(O)NR^aR^b$, —$OR^a$, and —$S(O)_2NR^aR^b$; wherein each $R^a$ and $R^b$ is independently selected from hydrogen, $C_{1-8}$ alkyl, and $C_{1-8}$ haloalkyl, or when attached to the same nitrogen atom can be combined with the nitrogen atom to form a five or six-membered ring having from 0 to 2 additional heteroatoms as ring members selected from N, O or S; each $R^c$ is independently selected from the group consisting of $C_{1-8}$ alkyl, $C_{1-8}$ haloalkyl, $C_{3-6}$ cycloalkyl, heterocycloalkyl, aryl and heteroaryl, and wherein the aliphatic and cyclic portions of $R^a$, $R^b$ and $R^c$ are optionally further substituted with from one to three halogen, hydroxy, methyl, amino, alkylamino and dialkylamino groups; and optionally when two $R^1$ substituents are on adjacent atoms, are combined to form a fused five or six-membered carbocyclic ring;
each $R^2$ is independently selected from the group consisting of
halogen, —CN, —$R^f$, —$CO_2R^d$, —$CONR^dR^e$, —C(O)$R^d$, —OC(O)$NR^dR^e$, —$NR^eC(O)R^d$, —$NR^eC(O)_2R^f$, —$NR^dC(O)NR^dR^e$, —$NR^dC(O)NR^dR^e$, —$OR^d$, and —$S(O)_2NR^dR^e$; wherein each $R^d$ and $R^e$ is independently selected from hydrogen, $C_{1-8}$ alkyl, and $C_{1-8}$ haloalkyl, or when attached to the same nitrogen atom can be combined with the nitrogen atom to form a five or six-membered ring having from 0 to 2 additional heteroatoms as ring members selected from N, O or S; each $R^f$ is independently selected from the group consisting of $C_{1-8}$ alkyl, $C_{1-8}$ haloalkyl, $C_{3-6}$ cycloalkyl, heterocycloalkyl, aryl and heteroaryl, and wherein the aliphatic and cyclic portions of $R^d$, $R^e$ and $R^f$ are optionally further substituted with from one to three halogen, hydroxy, methyl, amino, alkylamino and dialkylamino groups;
each $R^3$ is independently selected from the group consisting of
halogen, —CN, —$R^i$, —$CO_2R^g$, —$CONR_gR^h$, —C(O)$R^g$, —OC(O)$NR^gR^h$, —$NR^hC(O)R^g$, —$NR^hC(O)_2R^i$, —$NR^gC(O)NR^gR^h$, —$NR^gR^h$, —$OR^g$, —$S(O)_2NR^gR^h$, —$X^4$—$R^j$, —$X^4$—$NR^gR^h$, —$X^4$—$CONR^gT^h$, —$X^4$—$NR^hC(O)R^g$, —$NHR^j$ and —$NHCH_2R^j$, wherein $X^4$ is a $C_{1-4}$ alkylene; each $R^g$ and $R^h$ is independently selected from hydrogen, $C_{1-8}$ alkyl, $C_{3-6}$ cycloalkyl and $C_{1-8}$ haloalkyl, or when attached to the same nitrogen atom can be combined with the nitrogen atom to form a five or six-membered ring having from 0 to 2 additional heteroatoms as ring members selected from N, O or S and is optionally substituted with one or two oxo; each $R^i$ is independently selected from the group consisting of $C_{1-8}$ alkyl, $C_{1-8}$ haloalkyl, $C_{3-6}$ cycloalkyl, heterocycloalkyl, aryl and heteroaryl; and each $R^j$ is selected from the group consisting of $C_{3-6}$ cycloalkyl, pyrrolinyl, piperidinyl, morpholinyl, tetrahydrofuranyl, and tetrahydropyranyl, and wherein the aliphatic and cyclic portions of $R^g$, $R^h$, $R^i$ and $R^j$ are optionally further substituted with from one to three halogen, methyl, $CF_3$, hydroxy, amino, alkylamino and dialkylamino groups; and
X is hydrogen or $CH_3$.

In some embodiments, the compound has the formula (Ie):

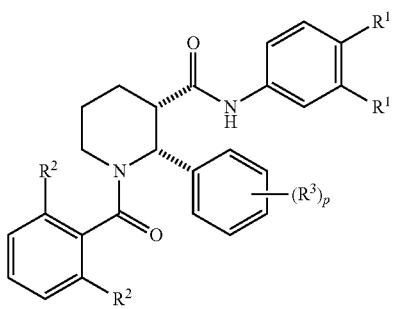

wherein p is 0, 1 or 2.

In some embodiments, the compound is

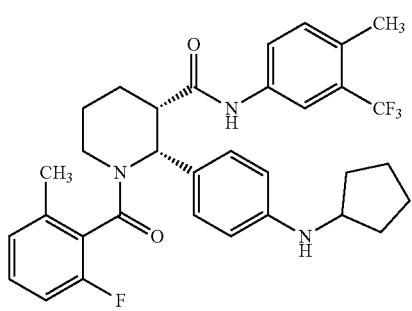 [SMILES: Cc1ccc(NC(=O)[C@H]2CCCN(C(=O)c3c(C)cccc3F)[C@H]2c2ccc(NC3CCCC3)cc2)cc1C(F)(F)F]

or a pharmaceutically acceptable salt thereof.

In some embodiments, the human suffers from complement 3 glomerulonephritis. In some embodiments, the human suffers from progressive complement 3 glomerulonephritis. In some embodiments, the human suffers from recurrent complement 3 glomerulonephritis after a renal transplant. In some embodiments, the human suffers from dense deposit disease.

A method of clearing glomerular endocapillary proliferation in a human suffering from or susceptible to C3 glomerulopathy is provided comprising administering to the human an effective amount of a compound having the formula (I), or a pharmaceutically acceptable salt thereof,

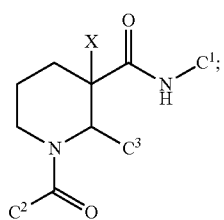

(I)

wherein
- $C^1$ is phenyl optionally substituted with from 1 to 3 $R^1$ substituents;
- $C^2$ is phenyl optionally substituted with from 1 to 3 $R^2$ substituents;
- $C^3$ is selected from the group consisting of $C_{3-8}$ cycloalkyl and phenyl, and each $C^3$ is optionally substituted with from 1-3 $R^3$ substituents;
- each $R^1$ is independently selected from the group consisting of
  halogen, —CN, —$R^c$, —$CO_2R^a$, —$CONR^aR^b$, —C(O)$R^a$, —OC(O)$NR^aR^b$, —$NR^bC(O)R^a$, —$NR^bC(O)_2R^c$, —$NR^aC(O)NR^aR^b$, —$OR^a$, and —$S(O)_2NR^aR^b$; wherein each $R^a$ and $R^b$ is independently selected from hydrogen, $C_{1-8}$ alkyl, and $C_{1-8}$ haloalkyl, or when attached to the same nitrogen atom can be combined with the nitrogen atom to form a five or six-membered ring having from 0 to 2 additional heteroatoms as ring members selected from N, O or S; each $R^c$ is independently selected from the group consisting of $C_{1-8}$ alkyl, $C_{1-8}$ haloalkyl, $C_{3-6}$ cycloalkyl, heterocycloalkyl, aryl and heteroaryl, and wherein the aliphatic and cyclic portions of $R^a$, $R^b$ and $R^c$ are optionally further substituted with from one to three halogen, hydroxy, methyl, amino, alkylamino and dialkylamino groups; and optionally when two $R^1$ substituents are on adjacent atoms, are combined to form a fused five or six-membered carbocyclic ring;
- each $R^2$ is independently selected from the group consisting of
  halogen, —CN, —$R^f$, —$CO_2R^d$, —$CONR^dR^e$, —C(O)$R^d$, —OC(O)$NR^dR^e$, —$NR^eC(O)R^d$, —$NR^eC(O)_2R^f$, —$NR^dC(O)NR^dR^e$, —$NR^dC(O)NR^dR^e$, —$NR^dR^e$, —$OR^d$, and —$S(O)_2NR^dR^e$; wherein each $R^d$ and $R^e$ is independently selected from hydrogen, $C_{1-8}$ alkyl, and $C_{1-8}$ haloalkyl, or when attached to the same nitrogen atom can be combined with the nitrogen atom to form a five or six-membered ring having from 0 to 2 additional heteroatoms as ring members selected from N, O or S; each $R^f$ is independently selected from the group consisting of $C_{1-8}$ alkyl, $C_{1-8}$ haloalkyl, $C_{3-6}$ cycloalkyl, heterocycloalkyl, aryl and heteroaryl, and wherein the aliphatic and cyclic portions of $R^d$, $R^e$ and $R^f$ are optionally further substituted with from one to three halogen, hydroxy, methyl, amino, alkylamino and dialkylamino groups;
- each $R^3$ is independently selected from the group consisting of
  halogen, —CN, —$R^i$, —$CO_2R^g$, —$CONR^gR^h$, —C(O)$R^g$, —OC(O)$NR^gR^h$, —$NR^hC(O)R^g$, —$NR^hC(O)_2R^i$, —$NR^gC(O)NR^gR^h$, —$NR^gR^h$, —$OR^g$, —$S(O)_2NR^gR^h$, —$X^4$—$R^j$, —$X^4$—$NR^gR^h$, —$X^4$—$CONR^gR^h$, —$X^4$—$NR^hC(O)R^g$, —$NHR^j$ and —$NHCH_2R^j$, wherein $X^4$ is a $C_{1-4}$ alkylene; each $R^g$ and $R^h$ is independently selected from hydrogen, $C_{1-8}$ alkyl, $C_{3-6}$ cycloalkyl and $C_{1-8}$ haloalkyl, or when attached to the same nitrogen atom can be combined with the nitrogen atom to form a five or six-membered ring having from 0 to 2 additional heteroatoms as ring members selected from N, O or S and is optionally substituted with one or two oxo; each $R^i$ is independently selected from the group consisting of $C_{1-8}$ alkyl, $C_{1-8}$ haloalkyl, $C_{3-6}$ cycloalkyl, heterocycloalkyl, aryl and heteroaryl; and each is selected from the group consisting of $C_{3-6}$ cycloalkyl, pyrrolinyl, piperidinyl, morpholinyl, tetrahydrofuranyl, and tetrahydropyranyl, and wherein the aliphatic and cyclic portions of $R^g$, $R^h$, $R^i$ and $R^j$ are optionally further substituted with from one to three halogen, methyl, $CF_3$, hydroxy, amino, alkylamino and dialkylamino groups; and
- X is hydrogen or $CH_3$.

In some embodiments, the compound has the formula (Ie):

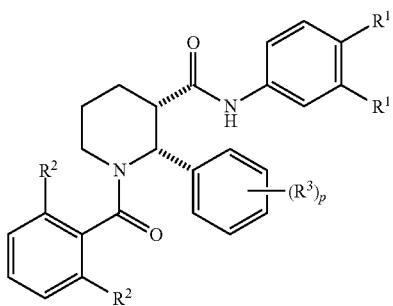

wherein p is 0, 1 or 2.

In some embodiments, the compound is

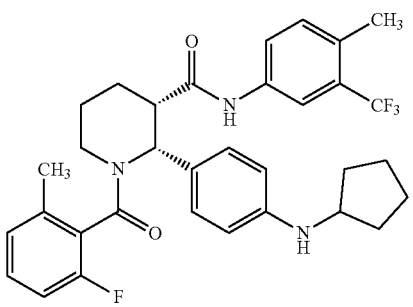 [SMILES: Cc1ccc(NC(=O)[C@H]2CCCN(C(=O)c3c(C)cccc3F)[C@H]2c2ccc(NC3CCCC3)cc2)cc1C(F)(F)F]

or a pharmaceutically acceptable salt thereof.

A method of reducing glomerular inflammatory macrophages in a human suffering from or susceptible to C3 glomerulopathy is provided comprising administering to the human an effective amount of a compound having the formula (I), or a pharmaceutically acceptable salt thereof,

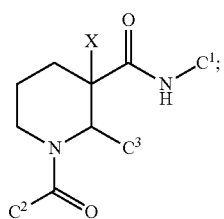

wherein
- $C^1$ is phenyl optionally substituted with from 1 to 3 $R^1$ substituents;
- $C^2$ is phenyl optionally substituted with from 1 to 3 $R^2$ substituents;
- $C^3$ is selected from the group consisting of $C_{3-8}$ cycloalkyl and phenyl, and each $C^3$ is optionally substituted with from 1-3 $R^3$ substituents;
- each $R^1$ is independently selected from the group consisting of
  halogen, —CN, —$R^c$, —$CO_2R^a$, —$CONR^aR^b$, —C(O)$R^a$, —OC(O)NR$^a$R$^b$, —NR$^b$C(O)R$^a$, —NR$^b$C(O)$_2$R$^c$, —NR$^a$C(O)NR$^a$R$^b$, —OR$^a$, and —S(O)$_2$NR$^a$R$^b$; wherein each $R^a$ and $R^b$ is independently selected from hydrogen, $C_{1-8}$ alkyl, and $C_{1-8}$ haloalkyl, or when attached to the same nitrogen atom can be combined with the nitrogen atom to form a five or six-membered ring having from 0 to 2 additional heteroatoms as ring members selected from N, O or S; each $R^c$ is independently selected from the group consisting of $C_{1-8}$ alkyl, $C_{1-8}$ haloalkyl, $C_{3-6}$ cycloalkyl, heterocycloalkyl, aryl and heteroaryl, and wherein the aliphatic and cyclic portions of $R^a$, $R^b$ and $R^c$ are optionally further substituted with from one to three halogen, hydroxy, methyl, amino, alkylamino and dialkylamino groups; and optionally when two $R^1$ substituents are on adjacent atoms, are combined to form a fused five or six-membered carbocyclic ring;
- each $R^2$ is independently selected from the group consisting of
  halogen, —CN, —$R^f$, —$CO_2R^d$, —$CONR^dR^e$, —C(O)$R^d$, —OC(O)NR$^d$R$^e$, —NR$^e$C(O)R$^d$, —NR$^e$C(O)$_2$R$^f$, —NR$^d$C(O)NR$^d$R$^e$, —NR$^d$C(O)NR$^d$R$^e$, —NR$^d$R$^e$, —OR$^d$, and —S(O)$_2$NR$^d$R$^e$; wherein each $R^d$ and $R^e$ is independently selected from hydrogen, $C_{1-8}$ alkyl, and $C_{1-8}$ haloalkyl, or when attached to the same nitrogen atom can be combined with the nitrogen atom to form a five or six-membered ring having from 0 to 2 additional heteroatoms as ring members selected from N, O or S; each $R^f$ is independently selected from the group consisting of $C_{1-8}$ alkyl, $C_{1-8}$ haloalkyl, $C_{3-6}$ cycloalkyl, heterocycloalkyl, aryl and heteroaryl, and wherein the aliphatic and cyclic portions of $R^d$, $R^e$ and $R^f$ are optionally further substituted with from one to three halogen, hydroxy, methyl, amino, alkylamino and dialkylamino groups;
- each $R^3$ is independently selected from the group consisting of
  halogen, —CN, —$R^i$, —$CO_2R^g$, —$CONR^gR^h$, —C(O)$R^g$, —OC(O)NR$^g$R$^h$, —NR$^h$C(O)R$^g$, —NR$^h$C(O)$_2$R$^i$, —NR$^g$C(O)NR$^g$R$^h$, —NR$^g$R$^h$, —OR$^g$, —S(O)$_2$NR$^g$R$^h$, —$X^4$—$R^j$, —$X^4$—NR$^g$R$^h$, —$X^4$—CONR$^g$R$^h$, —$X^4$—NR$^h$C(O)R$^g$, —NHR$^j$ and —NHCH$_2$R$^j$, wherein $X^4$ is a $C_{1-4}$ alkylene; each $R^g$ and $R^h$ is independently selected from hydrogen, $C_{1-8}$ alkyl, $C_{3-6}$ cycloalkyl and $C_{1-8}$ haloalkyl, or when attached to the same nitrogen atom can be combined with the nitrogen atom to form a five or six-membered ring having from 0 to 2 additional heteroatoms as ring members selected from N, O or S and is optionally substituted with one or two oxo; each $R^i$ is independently selected from the group consisting of $C_{1-8}$ alkyl, $C_{1-8}$ haloalkyl, $C_{3-6}$ cycloalkyl, heterocycloalkyl, aryl and heteroaryl; and each $R^j$ is selected from the group consisting of $C_{3-6}$ cycloalkyl, pyrrolinyl, piperidinyl, morpholinyl, tetrahydrofuranyl, and tetrahydropyranyl, and wherein the aliphatic and cyclic portions of $R^g$, $R^h$, $R^i$ and $R^j$ are optionally further substituted with from one to three halogen, methyl, $CF_3$, hydroxy, amino, alkylamino and dialkylamino groups; and
- X is hydrogen or $CH_3$.

In some embodiments, the compound has the formula (Ie):

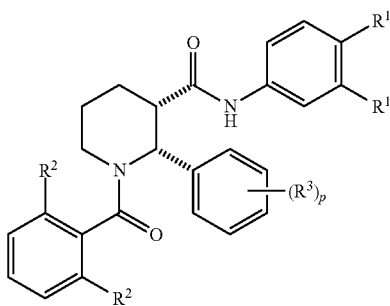

wherein p is 0, 1 or 2.

In some embodiments, the compound is

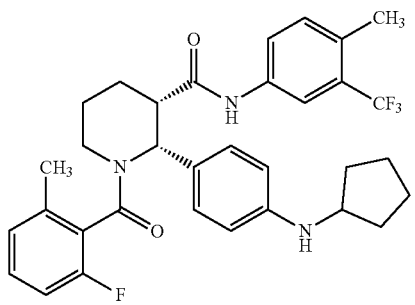 [SMILES: Cc1ccc(NC(=O)[C@H]2CCCN(C(=O)c3c(C)cccc3F)[C@H]2c2ccc(NC3CCCC3)cc2)cc1C(F)(F)F]

or a pharmaceutically acceptable salt thereof.

A method of reducing proteinuria in a human suffering from or susceptible to C3 glomerulopathy is provided comprising administering to the human an effective amount of a compound having the formula (I), or a pharmaceutically acceptable salt thereof,

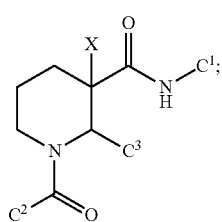

wherein
- $C^1$ is phenyl optionally substituted with from 1 to 3 $R^1$ substituents;
- $C^2$ is phenyl optionally substituted with from 1 to 3 $R^2$ substituents;
- $C^3$ is selected from the group consisting of $C_{3-8}$ cycloalkyl and phenyl, and each $C^3$ is optionally substituted with from 1-3 $R^3$ substituents;
- each $R^1$ is independently selected from the group consisting of
  halogen, —CN, —$R^c$, —$CO_2R^a$, —$CONR^aR^b$, —C(O)$R^a$, —OC(O)$NR^aR^b$, —$NR^bC(O)R^a$, —$NR^bC(O)_2R^c$, —$NR^aC(O)NR^aR^b$, —$NR^aR^b$, —$OR^a$, and —$S(O)_2NR^aR^b$; wherein each $R^a$ and $R^b$ is independently selected from hydrogen, $C_{1-8}$ alkyl, and $C_{1-8}$ haloalkyl, or when attached to the same nitrogen atom can be combined with the nitrogen atom to form a five or six-membered ring having from 0 to 2 additional heteroatoms as ring members selected from N, O or S; each $R^c$ is independently selected from the group consisting of $C_{1-8}$ alkyl, $C_{1-8}$ haloalkyl, $C_{3-6}$ cycloalkyl, heterocycloalkyl, aryl and heteroaryl, and wherein the aliphatic and cyclic portions of $R^a$, $R^b$ and $R^c$ are optionally further substituted with from one to three halogen, hydroxy, methyl, amino, alkylamino and dialkylamino groups; and optionally when two $R^1$ substituents are on adjacent atoms, are combined to form a fused five or six-membered carbocyclic ring;
- each $R^2$ is independently selected from the group consisting of
  halogen, —CN, —$R^f$, —$CO_2R^d$, —$CONR^dR^e$, —C(O)$R^d$, —OC(O)$NR^dR^e$, —$NR^eC(O)R^d$, —$NR^eC(O)_2R^f$, —$NR^dC(O)NR^dR^e$, —$NR^dC(O)NR^dR^e$, —$NR^dR^e$, —$OR^d$, and —$S(O)_2NR^dR^e$; wherein each $R^d$ and $R^e$ is independently selected from hydrogen, $C_{1-8}$ alkyl, and $C_{1-8}$ haloalkyl, or when attached to the same nitrogen atom can be combined with the nitrogen atom to form a five or six-membered ring having from 0 to 2 additional heteroatoms as ring members selected from N, O or S; each $R^f$ is independently selected from the group consisting of $C_{1-8}$ alkyl, $C_{1-8}$ haloalkyl, $C_{3-6}$ cycloalkyl, heterocycloalkyl, aryl and heteroaryl, and wherein the aliphatic and cyclic portions of $R^d$, $R^e$ and $R^f$ are optionally further substituted with from one to three halogen, hydroxy, methyl, amino, alkylamino and dialkylamino groups;
- each $R^3$ is independently selected from the group consisting of
  halogen, —CN, —$R^i$, —$CO_2R^g$, —$CONR^gR^h$, —C(O)$R^g$, —OC(O)$NR^gR^h$, —$NR^hC(O)R^g$, —$NR^hC(O)_2R^i$, —$NR^gC(O)NR^gR^h$, —$NR^gR^h$, —$OR^g$, —$S(O)_2NR^gR^h$, —$X^4$—$R^j$, —$X^4$—$NR^gR^h$, —$X^4$—$CONR^gR^h$, —$X^4$—$NR^hC(O)R^g$, —$NHR^j$ and —$NHCH_2R^j$, wherein $X^4$ is a $C_{1-4}$ alkylene; each $R^g$ and $R^h$ is independently selected from hydrogen, $C_{1-8}$ alkyl, $C_{3-6}$ cycloalkyl and $C_{1-8}$haloalkyl, or when attached to the same nitrogen atom can be combined with the nitrogen atom to form a five or six-membered ring having from 0 to 2 additional heteroatoms as ring members selected from N, O or S and is optionally substituted with one or two oxo; each $R^i$ is independently selected from the group consisting of $C_{1-8}$ alkyl, $C_{1-8}$ haloalkyl, $C_{3-6}$ cycloalkyl, heterocycloalkyl, aryl and heteroaryl; and each is selected from the group consisting of $C_{3-6}$ cycloalkyl, pyrrolinyl, piperidinyl, morpholinyl, tetrahydrofuranyl, and tetrahydropyranyl, and wherein the aliphatic and cyclic portions of $R^g$, $R^h$, $R^i$ and $R^j$ are optionally further substituted with from one to three halogen, methyl, $CF_3$, hydroxy, amino, alkylamino and dialkylamino groups; and X is hydrogen or $CH_3$.

In some embodiments, the compound has the formula (Ie):

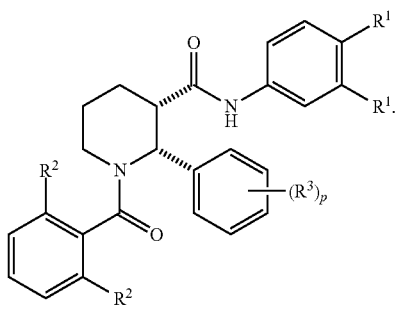

I(e)

In some embodiments, the compound is

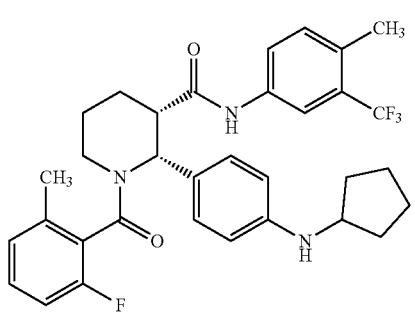 [SMILES: Cc1ccc(NC(=O)[C@H]2CCCN(C(=O)c3c(C)cccc3F)[C@H]2c2ccc(NC3CCCC3)cc2)cc1C(F)(F)F]

or a pharmaceutically acceptable salt thereof.

In some embodiments, the human suffers from complement 3 glomerulonephritis. In some embodiments, the human suffers from progressive complement 3 glomerulonephritis. In some embodiments, the human suffers from recurrent complement 3 glomerulonephritis after a renal transplant. In some embodiments, the human suffers from dense deposit disease. In some embodiments, the human had refractory disease to immunosuppressive drugs.

A method of treating a human suffering from or susceptible to complement 3 glomerulopathy is provided comprising administering to the human an effective amount of a compound having the formula (Ie), or a pharmaceutically acceptable salt thereof,

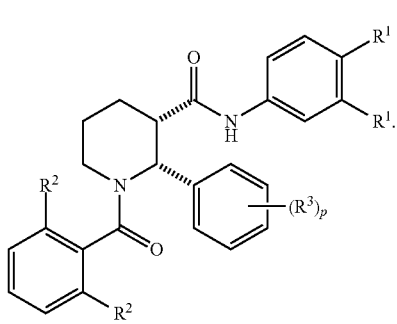

I(e)

wherein
each $R^1$ is independently selected from the group consisting of
halogen, —CN, —$R^c$, —$CO_2R^a$, —$CONR^aR^b$, —C(O)$R^a$, —OC(O)$NR^aR^b$, —$NR^bC(O)R^a$, —$NR^bC(O)_2R^c$, —$NR^aC(O)NR^aR^b$, —$OR^a$, and —$S(O)_2NR^aR^b$; wherein each $R^a$ and $R^b$ is independently selected from hydrogen, $C_{1-8}$ alkyl, and $C_{1-8}$ haloalkyl, or when attached to the same nitrogen atom can be combined with the nitrogen atom to form a five or six-membered ring having from 0 to 2 additional heteroatoms as ring members selected from N, O or S; each $R^c$ is independently selected from the group consisting of $C_{1-8}$ alkyl, $C_{1-8}$ haloalkyl, $C_{3-6}$ cycloalkyl, heterocycloalkyl, aryl and heteroaryl, and wherein the aliphatic and cyclic portions of $R^a$, $R^b$ and $R^c$ are optionally further substituted with from one to three halogen, hydroxy, methyl, amino, alkylamino and dialkylamino groups; and optionally when two $R^1$ substituents are on adjacent atoms, are combined to form a fused five or six-membered carbocyclic ring;

each $R^2$ is independently selected from the group consisting of
halogen, —CN, —$R^f$, —$CO_2R^d$, —$CONR^dR^e$, —C(O)$R^d$, —OC(O)$NR^dR^e$, —$NR^eC(O)R^d$, —$NR^eC(O)_2R^f$, —$NR^dC(O)NR^dR^e$, —$NR^dC(O)NR^dR^e$, —$NR^dR^e$, —$OR^d$, and —$S(O)_2NR^dR^e$; wherein each $R^d$ and $R^e$ is independently selected from hydrogen, $C_{1-8}$ alkyl, and $C_{1-8}$ haloalkyl, or when attached to the same nitrogen atom can be combined with the nitrogen atom to form a five or six-membered ring having from 0 to 2 additional heteroatoms as ring members selected from N, O or S; each $R^f$ is independently selected from the group consisting of $C_{1-8}$ alkyl, $C_{1-8}$ haloalkyl, $C_{3-6}$ cycloalkyl, heterocycloalkyl, aryl and heteroaryl, and wherein the aliphatic and cyclic portions of $R^d$, $R^e$ and $R^f$ are optionally further substituted with from one to three halogen, hydroxy, methyl, amino, alkylamino and dialkylamino groups;

each $R^3$ is independently selected from the group consisting of
halogen, —CN, —$R^i$, —$CO_2R^g$, —$CONR^gR^h$, —C(O)$R^g$, —OC(O)$NR^gR^h$, —$NR^hC(O)R^g$, —$NR^hC(O)_2R^i$, —$NR^gC(O)NR^gR^h$, —$NR^gR^h$, —$OR^g$, —$S(O)_2NR^gR^h$, —$X^4$—$R^j$, —$X^4$—$NR^gR^h$, —$X^4$—$CONR^gR^h$, —$X^4$—$NR^hC(O)R^g$, —$NHR^j$ and —$NHCH_2R^j$, wherein $X^4$ is a $C_{1-4}$ alkylene; each $R^g$ and $R^h$ is independently selected from hydrogen, $C_{1-8}$ alkyl, $C_{3-6}$ cycloalkyl and $C_{1-8}$ haloalkyl, or when attached to the same nitrogen atom can be combined with the nitrogen atom to form a five or six-membered ring having from 0 to 2 additional heteroatoms as ring members selected from N, O or S and is optionally substituted with one or two oxo; each $R^i$ is independently selected from the group consisting of $C_{1-8}$ alkyl, $C_{1-8}$ haloalkyl, $C_{3-6}$ cycloalkyl, heterocycloalkyl, aryl and heteroaryl; and each $R^j$ is selected from the group consisting of $C_{3-6}$ cycloalkyl, pyrrolinyl, piperidinyl, morpholinyl, tetrahydrofuranyl, and tetrahydropyranyl, and wherein the aliphatic and cyclic portions of $R^g$, $R^h$, $R^i$ and $R^j$ are optionally further substituted with from one to three halogen, methyl, $CF_3$, hydroxy, amino, alkylamino and dialkylamino groups; and p is 0, 1 or 2.

In some embodiments,
each $R^1$ is independently selected from the group consisting of halogen, —CN, —$R^c$, —$NR^aR^b$, and —$OR^a$; wherein each $R^a$ and $R^b$ is independently selected from hydrogen, $C_{1-8}$ alkyl, and $C_{1-8}$ haloalkyl, or when attached to the same nitrogen atom can be combined with the nitrogen atom to form a pyrrolidine ring; each R$^c$ is independently selected from the group consisting of C$_{1-8}$ alkyl, C$_{1-8}$ haloalkyl, C$_{3-6}$ cycloalkyl and wherein the aliphatic and cyclic portions of R$^a$, R$^b$ and R$^c$ are optionally further substituted with from one to three hydroxy, methyl, amino, alkylamino and dialkylamino groups; and optionally when two R$^1$ substituents are on adjacent atoms, are combined to form a fused five or six-membered carbocyclic ring;

each R$^2$ is independently selected from the group consisting of halogen, —R$^f$, and —OR$^d$; wherein each R$^d$ is independently selected from hydrogen, C$_{1-8}$ alkyl, and C$_{1-8}$ haloalkyl, each R$^f$ is independently selected from the group consisting of C$_{1-8}$ alkyl, C$_{1-8}$ haloalkyl, C$_{3-6}$ cycloalkyl, heterocycloalkyl and heteroaryl, and wherein the aliphatic and cyclic portions of R$^d$ and R$^f$ are optionally further substituted with from one to three halogen, hydroxy, methyl, amino, alkylamino and dialkylamino groups;

each R$^3$ is independently selected from the group consisting of halogen, —R$^i$, —CO$_2$R$^g$, —CONR$^g$R$^h$, —NR$^h$C(O)R$^g$, —NR$^h$C(O)$_2$R$^i$, —NR$^g$R$^h$, —OR$^g$, —X$^4$—R$^j$, —X$^4$—NR$^g$R$^h$, —X$^4$—CONR$^g$R$^h$, —X$^4$—NR$^h$C(O)R$^g$, —NHR$^j$ and —NHCH$_2$R$^j$, wherein X$^4$ is a C$_{1-4}$ alkylene; each R$^g$ and R$^h$ is independently selected from hydrogen, C$_{1-8}$ alkyl, C$_{3-6}$ cycloalkyl and C$_{1-8}$ haloalkyl, or when attached to the same nitrogen atom can be combined with the nitrogen atom to form a five or six-membered ring having from 0 to 2 additional heteroatoms as ring members selected from N, O or S and is optionally substituted with one or two oxo; each R$^i$ is independently selected from the group consisting of C$_{1-8}$ alkyl, C$_{1-8}$ haloalkyl, C$_{3-6}$ cycloalkyl, heterocycloalkyl, aryl and heteroaryl; and each R$^j$ is selected from the group consisting of C$_{3-6}$ cycloalkyl, pyrrolinyl, piperidinyl, morpholinyl, tetrahydrofuranyl, and tetrahydropyranyl, and wherein the aliphatic and cyclic portions of R$^g$, R$^h$, R$^i$ and R$^j$ are optionally further substituted with from one to three halogen, methyl, CF$_3$, hydroxy, amino, alkylamino and dialkylamino groups; and p is 1.

In Some Embodiments, each R$^1$ is independently selected from the group consisting of C$_{1-8}$ alkyl and C$_{1-8}$ haloalkyl;

each R$^2$ is independently selected from the group consisting of halogen and C$_{1-8}$ alkyl;

each R$^3$ is —NR$^g$R$^h$ wherein each R$^g$ and R$^h$ is independently selected from hydrogen and C$_{3-6}$ cycloalkyl; and p is 1.

In Some Embodiments, each R$^1$ is independently selected from the group consisting of C$_{1-3}$ alkyl and C$_{1-3}$ haloalkyl;

each R$^2$ is independently selected from the group consisting of halogen and C$_{1-3}$ alkyl;

each R$^3$ is —NR$^g$R$^h$ wherein each R$^g$ and R$^h$ is independently selected from hydrogen and C$_{4-6}$ cycloalkyl; and p is 1.

In some embodiments, the compound is selected from the group consisting of

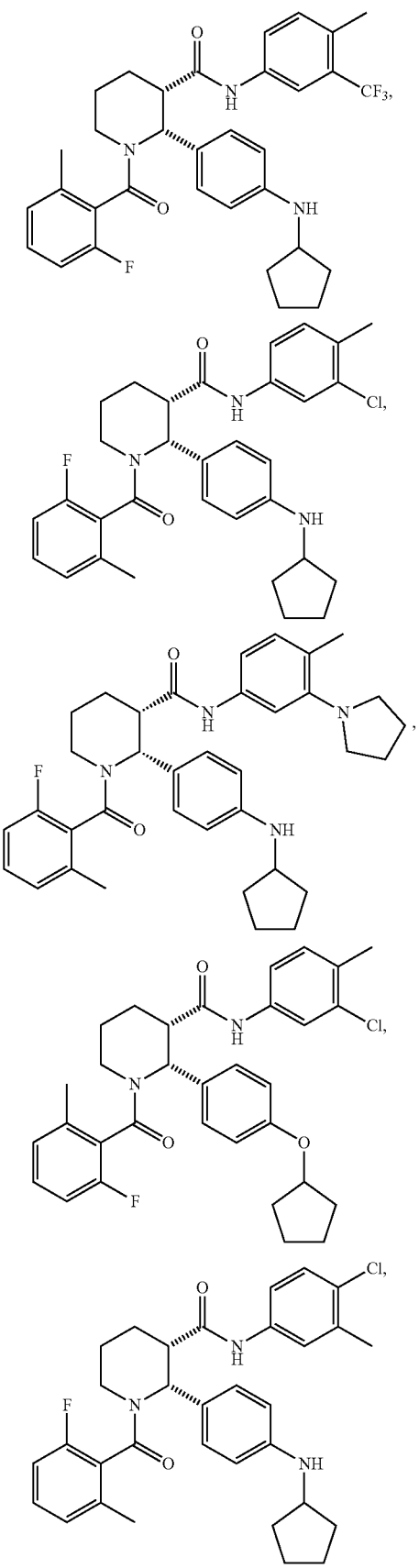

35
-continued
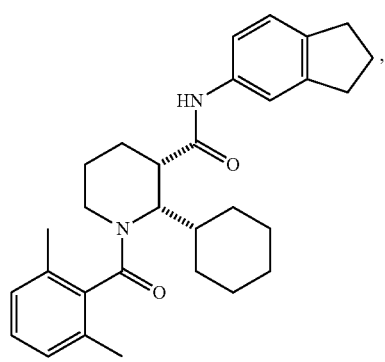
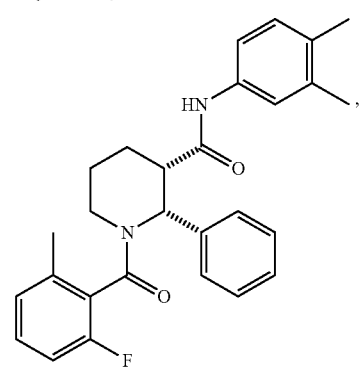
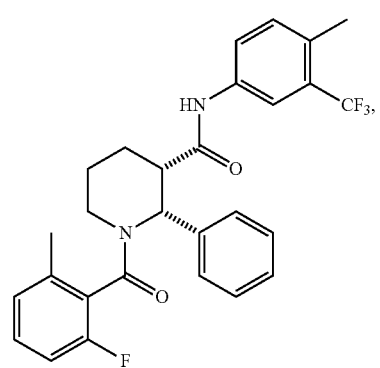
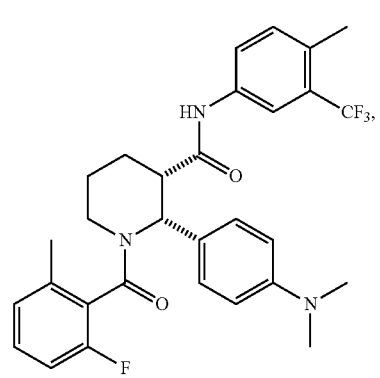
36
-continued
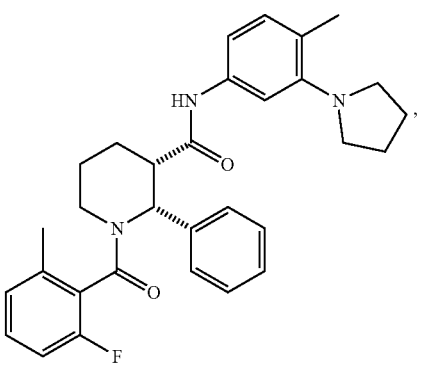
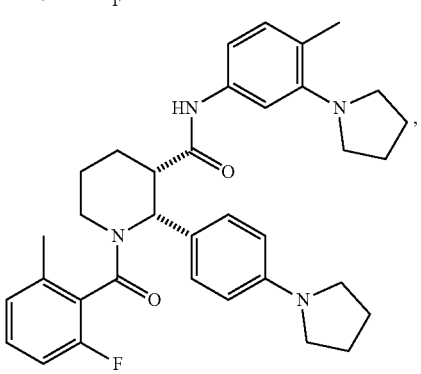
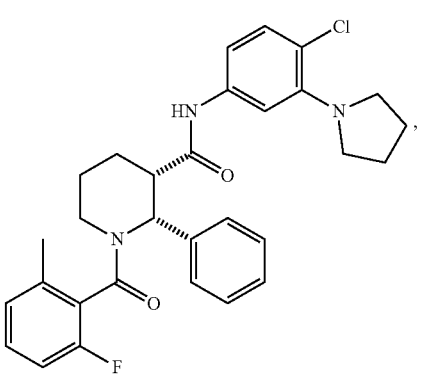
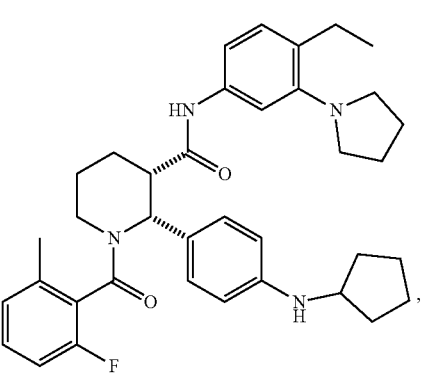

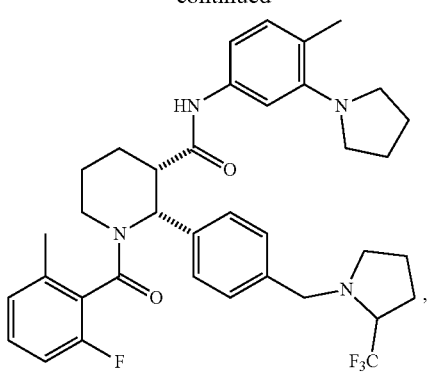
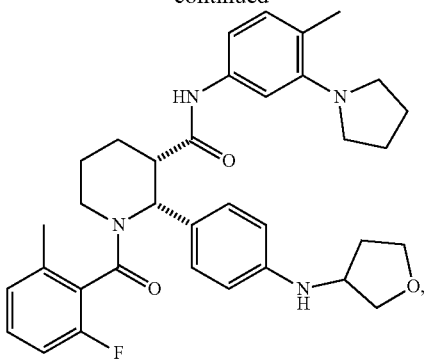
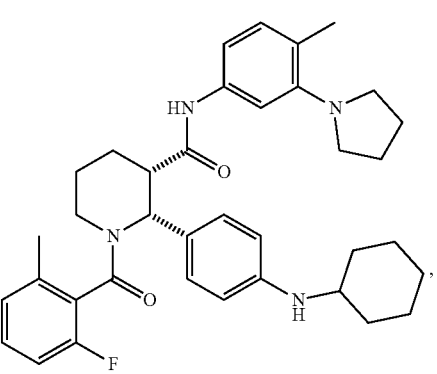
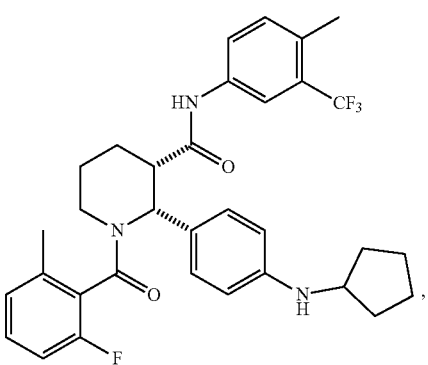
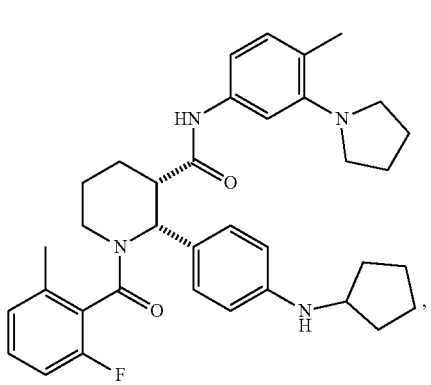
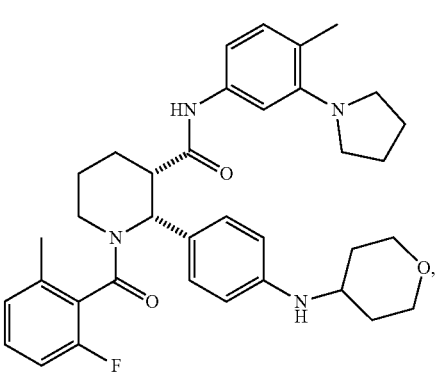

-continued
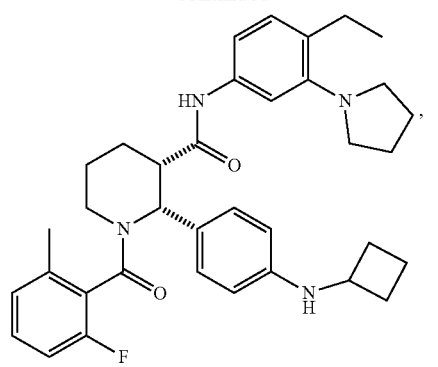
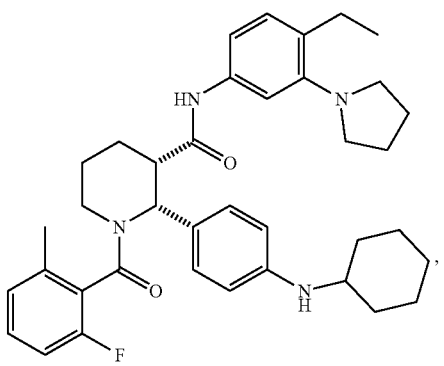
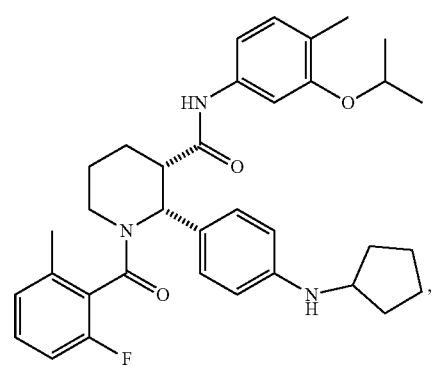
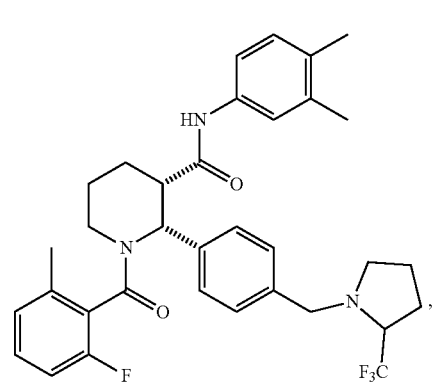
-continued
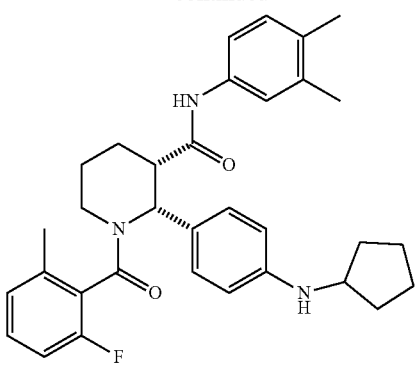
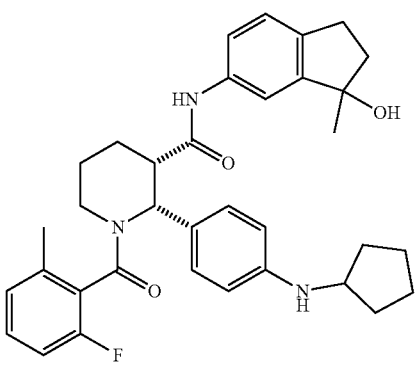
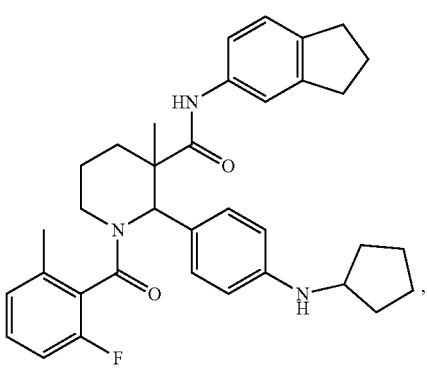
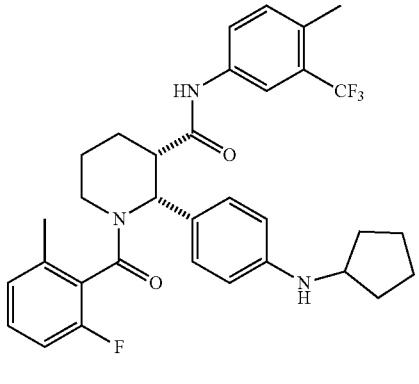 [SMILES: Cc1ccc(NC(=O)[C@H]2CCCN(C(=O)c3c(C)cccc3F)[C@H]2c2ccc(OC3CCCC3)cc2)cc1C(F)(F)F]

-continued

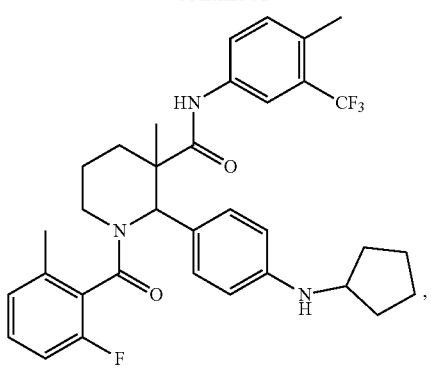

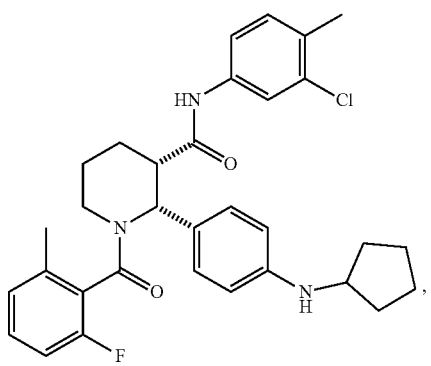

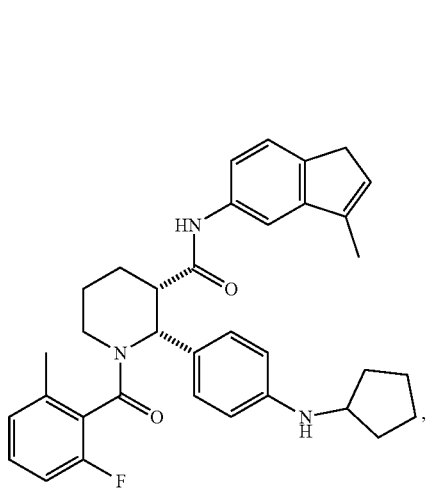

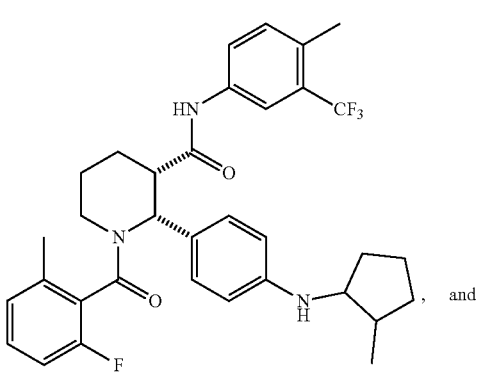, and

-continued

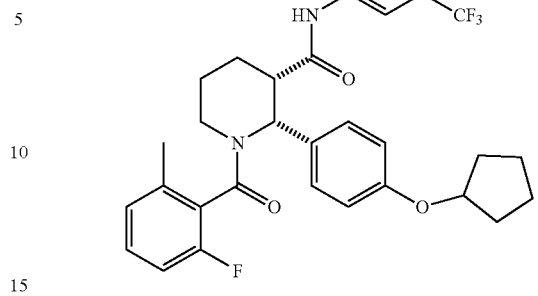

or a pharmaceutically acceptable salt thereof.

In some embodiments, the compound is

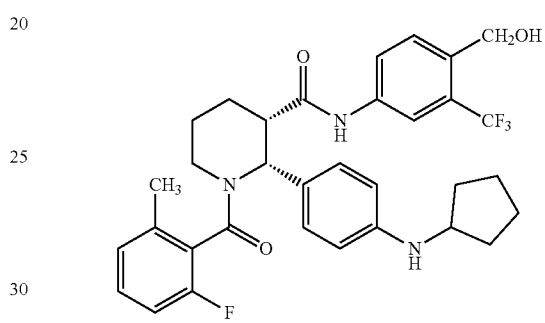

or a pharmaceutically acceptable salt thereof.

In some embodiments, the compound is

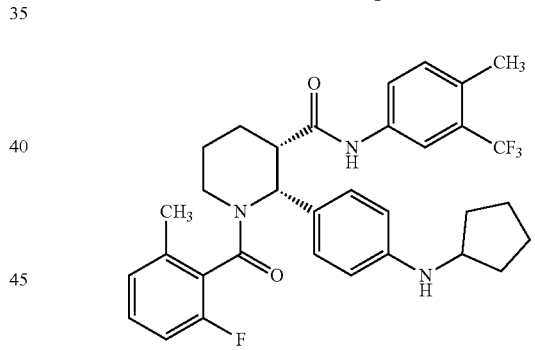

or a pharmaceutically acceptable salt thereof.

In some embodiments, the method comprises one or more of: slowing the rate of decline in Estimated Glomerular Filtration Rate (eGFR) in the human, reducing glomerular inflammation in the human, clearing glomerular endocapillary proliferation in the human, reducing glomerular inflammatory macrophages in the human, reducing proteinuria in the human, slowing down the progression of renal disease in the human, stopping the progression of renal disease in the human, delaying end stage renal disease in the human, improving renal histology in the human, decreasing proteinuria in the human, slowing the increase in proteinuria in the human. In some embodiments, the improvements may be supported by kidney biopsy.

A method of slowing the rate of decline in Estimated Glomerular Filtration Rate (eGFR) in a human suffering from or susceptible to C3 glomerulopathy is provided comprising administering to the human an effective amount of a compound having the following formula:

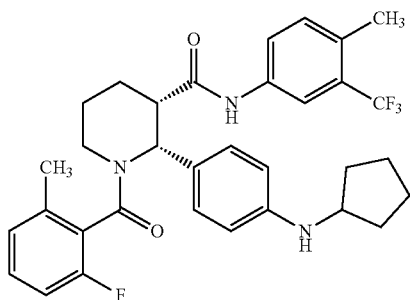 [SMILES: Cc1ccc(NC(=O)[C@H]2CCCN(C(=O)c3c(C)cccc3F)[C@H]2c2ccc(NC3CCCC3)cc2)cc1C(F)(F)F]

or a pharmaceutically acceptable salt thereof.

A method of slowing the rate of decline in Estimated Glomerular Filtration Rate (eGFR) in a human suffering from or susceptible to C3 glomerulopathy is provided comprising administering to the human an effective amount of a compound having the following formula:

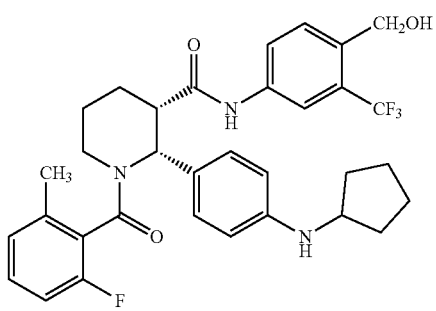 [SMILES: Cc1cccc(F)c1C(=O)N1CCC[C@H](C(=O)Nc2ccc(CO)c(C(F)(F)F)c2)[C@@H]1c1ccc(NC2CCCC2)cc1]

or a pharmaceutically acceptable salt thereof.

A method of reducing glomerular inflammation in a human suffering from or susceptible to C3 glomerulopathy is provided comprising administering to the human an effective amount of a compound having the following formula:

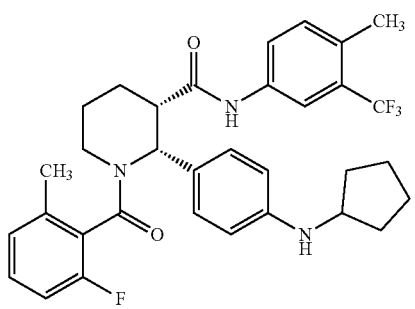 [SMILES: Cc1ccc(NC(=O)[C@H]2CCCN(C(=O)c3c(C)cccc3F)[C@H]2c2ccc(NC3CCCC3)cc2)cc1C(F)(F)F]

or a pharmaceutically acceptable salt thereof.

A method of reducing glomerular inflammation in a human suffering from or susceptible to C3 glomerulopathy is provided comprising administering to the human an effective amount of a compound having the following formula:

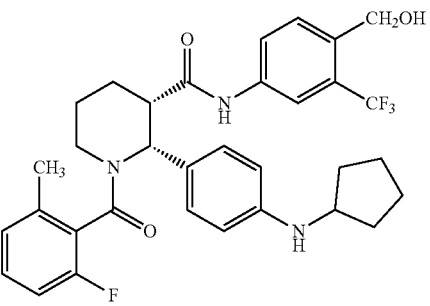 [SMILES: Cc1cccc(F)c1C(=O)N1CCC[C@H](C(=O)Nc2ccc(CO)c(C(F)(F)F)c2)[C@@H]1c1ccc(NC2CCCC2)cc1]

or a pharmaceutically acceptable salt thereof.

A method of reducing C3 deposits and/or C5b-9 deposits in a human suffering from or susceptible to C3 glomerulopathy is provided comprising administering to the human an effective amount of a compound having the following formula:

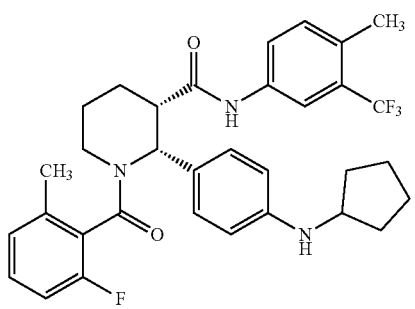 [SMILES: Cc1ccc(NC(=O)[C@H]2CCCN(C(=O)c3c(C)cccc3F)[C@H]2c2ccc(NC3CCCC3)cc2)cc1C(F)(F)F]

or a pharmaceutically acceptable salt thereof.

A method of reducing C3 deposits and/or C5b-9 deposits in a human suffering from or susceptible to C3 glomerulopathy is provided comprising administering to the human an effective amount of a compound having the following formula:

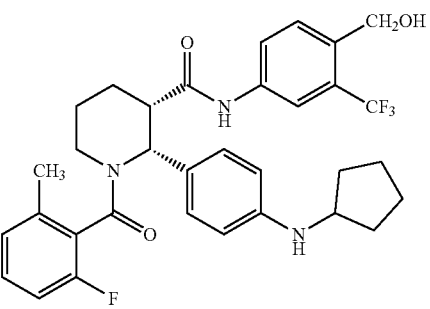 [SMILES: Cc1cccc(F)c1C(=O)N1CCC[C@H](C(=O)Nc2ccc(CO)c(C(F)(F)F)c2)[C@@H]1c1ccc(NC2CCCC2)cc1]

or a pharmaceutically acceptable salt thereof.

A method of clearing glomerular endocapillary proliferation in a human suffering from or susceptible to C3 glomerulopathy is provided comprising administering to the human an effective amount of a compound having the following formula:

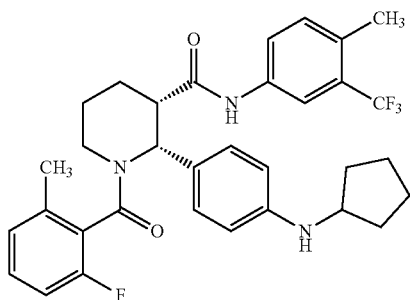 [SMILES: Cc1ccc(NC(=O)[C@H]2CCCN(C(=O)c3c(C)cccc3F)[C@H]2c2ccc(NC3CCCC3)cc2)cc1C(F)(F)F]

or a pharmaceutically acceptable salt thereof.

A method of clearing glomerular endocapillary proliferation in a human suffering from or susceptible to C3 glomerulopathy is provided comprising administering to the human an effective amount of a compound having the following formula:

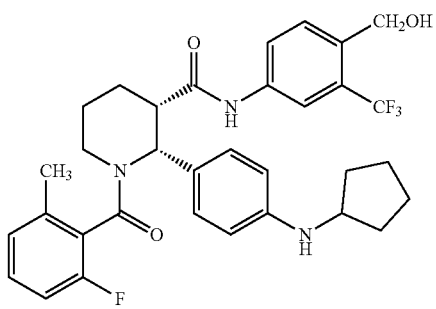 [SMILES: Cc1cccc(F)c1C(=O)N1CCC[C@H](C(=O)Nc2ccc(CO)c(C(F)(F)F)c2)[C@@H]1c1ccc(NC2CCCC2)cc1]

or a pharmaceutically acceptable salt thereof.

A method of reducing glomerular inflammatory macrophages in a human suffering from or susceptible to C3 glomerulopathy is provided comprising administering to the human an effective amount of a compound having the following formula:

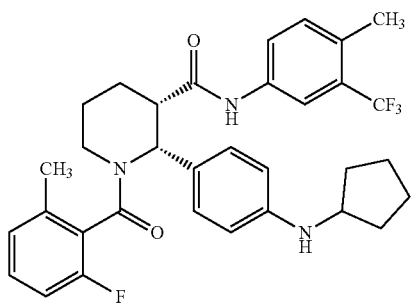 [SMILES: Cc1ccc(NC(=O)[C@H]2CCCN(C(=O)c3c(C)cccc3F)[C@H]2c2ccc(NC3CCCC3)cc2)cc1C(F)(F)F]

or a pharmaceutically acceptable salt thereof.

A method of reducing glomerular inflammatory macrophages in a human suffering from or susceptible to C3 glomerulopathy is provided comprising administering to the human an effective amount of a compound having the following formula:

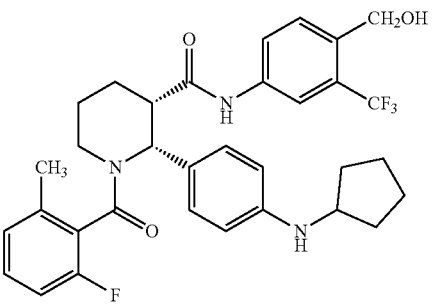 [SMILES: Cc1cccc(F)c1C(=O)N1CCC[C@H](C(=O)Nc2ccc(CO)c(C(F)(F)F)c2)[C@@H]1c1ccc(NC2CCCC2)cc1]

or a pharmaceutically acceptable salt thereof.

A method of reducing proteinuria in a human suffering from or susceptible to C3 glomerulopathy is provided comprising administering to the human an effective amount of a compound having the following formula:

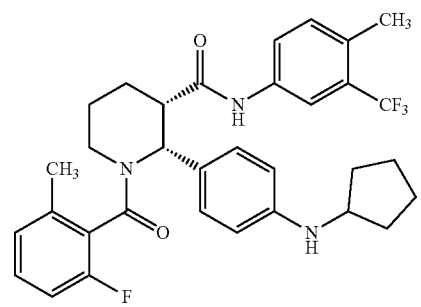 [SMILES: Cc1ccc(NC(=O)[C@H]2CCCN(C(=O)c3c(C)cccc3F)[C@H]2c2ccc(NC3CCCC3)cc2)cc1C(F)(F)F]

or a pharmaceutically acceptable salt thereof.

A method of reducing proteinuria in a human suffering from or susceptible to C3 glomerulopathy is provided comprising administering to the human an effective amount of a compound having the following formula:

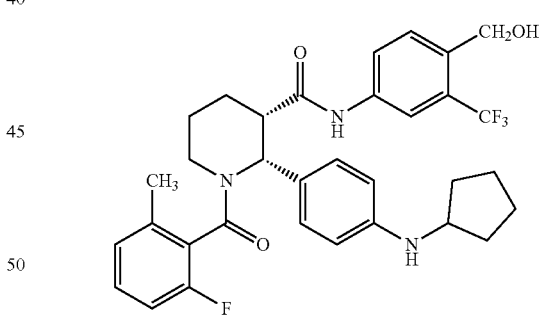

or a pharmaceutically acceptable salt thereof.

In some embodiments, the human suffers from complement 3 glomerulonephritis. In some embodiments, the human suffers from progressive complement 3 glomerulonephritis. In some embodiments, the human suffers from recurrent complement 3 glomerulonephritis after a renal transplant. In some embodiments, the human suffers from dense deposit disease.

In some embodiments, the complement 3 glomerulopathy is refractory to treatment. In some embodiments, the complement 3 glomerulonephritis is refractory to other treatment. In some embodiments, the human has refractory disease to immunosuppressive drugs. In some embodiments, the human has refractory disease to one or more of rituximab, cyclophosphamide, mycophenolate mofetil, tacrolimus, and steroids. In some embodiments, the human has refractory disease to one or more of rituximab, cyclophosphamide, mycophenolate mofetil, tacrolimus, and glucocorticosteroids. In some embodiments, the human shows improved health-related quality of life changes. In some embodiments, the health-related quality-of-life is based on Short Form-36 version 2 (SF-36 v2) or EuroQOL-5D-5L (EQ-5D-5L) assessment. In some embodiments, the health-related quality-of-life is based on Short Form-36 version 2 (SF-36 v2) assessment. In some embodiments, the health-related quality-of-life is based on EuroQOL-5D-5L (EQ-5D-5L) assessment.

In some embodiments, the compound is administered twice daily. In some embodiments, the compound is administered once a day. In some embodiments, the compound is administered every other day. In some embodiments, the compound is administered every 3 days. In some embodiments, the compound is administered 3 times per day. In some embodiments, the compound is administered 4 times per day.

In some embodiments, the human receives 30 mg of the compound daily. In some embodiments, the human receives 20 mg of the compound daily. In some embodiments, the human receives 10 mg of the compound daily. In some embodiments, the human receives 40 mg of the compound daily. In some embodiments, the human receives 60 mg of the compound daily. In some embodiments, the human receives 50 mg, 70 mg, 80 mg, 90 mg, 100 mg, 150 mg or 200 mg of the compound daily.

In some embodiments, the human receives 30 mg of the compound twice daily. In some embodiments, the human receives 20 mg of the compound twice daily. In some embodiments, the human receives 10 mg of the compound twice daily.

In some embodiments, the compound is administered orally.

In some embodiments, the human has a Complement factor H related protein 5 (CFHR5) mutation.

In some embodiments, the human receives treatment for 12 weeks. In some embodiments, the human receives treatment for 26 weeks. In some embodiments, the human receives treatment for 52 weeks. In some embodiments, the human receives chronic treatment. In some embodiments, the human receives continuous treatment.

In some embodiments, the method further comprises administering to the human a therapeutically effective amount of one or more additional therapeutic agents. In some embodiments, the one or more additional therapeutic agents is administered sequentially or concurrently in the same composition or not.

In some embodiments, the one or more additional therapeutic agents is selected from immunosuppressive drugs, angiotensin-converting enzyme (ACE) inhibitors, angiotensin II type-1 receptor blockers (ARBs) and corticosteroids.

In some embodiments, the one or more additional therapeutic agents is selected from the group consisting of cyclophosphamide, mycophenolate mofetil, rituximab, eculizumab, tacrolimus, belimumab, OMS721, ACH-4471, AMY-101, Acthar Gel, SAND-5, corticotropin, CDX-1135, ramipril, perindopril, lisinopril, perindopril arginine, captopril, spirapril, quinapril, enalapril, imidapril, fosinopril, zofenopril, benazepril, trandolapril, verapamil, benazepril, amlodipine, trandolapril, P-003, cilazapril, delapril, moexipril, quinapril, fosinopril, temocapril, losartan, candesartan, irbesartan, telmisartan, olmesartan, valsartan, azilsartan, telmisartan, fimasartan, EMA-401, azilsartan medoxomil potassium, sparsentan, candesartan cilexetil, olmesartan medoxomil, TRV-027, losartan potassium, YH-22189, azilsartan trimethylethanolamine, allisartan isoproxil, and eprosartan. In some embodiments, the one or more additional therapeutic agents is selected from the group consisting of cyclophosphamide, mycophenolate mofetil, rituximab, eculizumab, and tacrolimus.

In some embodiments, the one or more additional therapeutic agents is selected from the group consisting of corticosteroids, steroids, immunosuppressants, Immunoglobulin G agonists, Dipeptidyl peptidase IV inhibitors, Lymphocyte function antigen-3 receptor antagonists, Interleukin-2 ligands, Interleukin-1 beta ligand inhibitors, IL-2 receptor alpha subunit inhibitors, HGF gene stimulators, IL-6 antagonists, IL-5 antagonists, Alpha 1 antitrypsin stimulators, Cannabinoid receptor antagonists, Histone deacetylase inhibitors, AKT protein kinase inhibitors, CD20 inhibitors, Abl tyrosine kinase inhibitors, JAK tyrosine kinase inhibitors, TNF alpha ligand inhibitors, Hemoglobin modulators, TNF antagonists, proteasome inhibitors, CD3 modulators, Hsp 70 family inhibitors, Immunoglobulin agonists, CD30 antagonists, tubulin antagonists, Sphingosine-1-phosphate receptor-1 agonists, connective tissue growth factor ligand inhibitors, caspase inhibitors, adrenocorticotrophic hormone ligands, Btk tyrosine kinase inhibitors, Complement C1s subcomponent inhibitors, Erythropoietin receptor agonists, B-lymphocyte stimulator ligand inhibitors, Cyclin-dependent kinase-2 inhibitors, P-selectin glycoprotein ligand-1 stimulators, mTOR inhibitors, Elongation factor 2 inhibitors, Cell adhesion molecule inhibitors, Factor XIII agonists, Calcineurin inhibitors, Immunoglobulin G1 agonists, Inosine monophosphate dehydrogenase inhibitors, Complement C1s subcomponent inhibitors, Thymidine kinase modulators, Cytotoxic T-lymphocyte protein-4 modulators, Angiotensin II receptor antagonists, Angiotensin II receptor modulators, TNF superfamily receptor 12A antagonists, CD52 antagonists, Adenosine deaminase inhibitors, T-cell differentiation antigen CD6 inhibitors, FGF-7 ligands, dihydroorotate dehydrogenase inhibitors, CCR5 chemokine antagonists, CCR2 chemokine antagonists, Syk tyrosine kinase inhibitors, Interferon type I receptor antagonists, Interferon alpha ligand inhibitors, Macrophage migration inhibitory factor inhibitors, Integrin alpha-V/beta-6 antagonists, Cysteine protease stimulators, p38 MAP kinase inhibitors, TP53 gene inhibitors, Shiga like toxin I inhibitors, Fucosyltransferase 6 stimulators, Interleukin 22 ligands, CXCR1 chemokine antagonists, CXCR4 chemokine antagonists, IRS1 gene inhibitors, Protein kinase C stimulators, Protein kinase C alpha inhibitors, CD74 antagonists, Immunoglobulin gamma Fc receptor IIB antagonists, T-cell antigen CD7 inhibitors, CD95 antagonists, N acetylmannosamine kinase stimulators, Cardiotrophin-1 ligands, Leukocyte elastase inhibitors, CD40 ligand receptor antagonists, CD40 ligand modulators, IL-17 antagonists, TLR-2 antagonists, complement factor D inhibitors, complement factor B inhibitors, complement C5 inhibitors, MASP-2 inhibitors, MASP-3 inhibitors, C3 inhibitors, pegylated APL-1, C1s inhibitors, C6 inhibitors, and T cell receptor antagonists.

In some embodiments, the one or more additional therapeutic agents is selected from the group consisting of obinutuzumab, rituximab, ocrelizumab, cyclophosphamide, prednisone, hydrocortisone, hydrocortisone acetate, cortisone acetate, tixocortol pivalate, prednisolone, methylprednisolone, triamcinolone acetonide, triamcinolone alcohol, mometasone, amcinonide, budesonide, desonide, fluocinonide, fluocinolone acetonide, halcinonide, betamethasone, betamethasone sodium phosphate, dexamethasone, dexamethasone sodium phosphate, fluocortolone, hydrocortisone-17-valerate, halometasone, alclometasone dipropionate, beclomethasone, betamethasone valerate, betamethasone dipropionate, prednicarbate, clobetasone-17-butyrate, clobetasol-17-propionate, fluocortolone caproate, fluocortolone pivalate, fluprednidene acetate, hydrocortisone-17-butyrate, hydrocortisone-17-aceponate, hydrocortisone-17-buteprate, ciclesonide and prednicarbate, GB-0998, immuglo, begelomab, alefacept, aldesleukin, gevokizumab, daclizumab, basiliximab, inolimomab, beperminogene perplasmid, sirukumab, tocilizumab, clazakizumab, mepolizumab, fingolimod, panobinostat, triciribine, nilotinib, imatinib, tofacitinib, momelotinib, peficitinib, itacitinib, infliximab, PEG-bHb-CO, etanercept, ixazomib, bortezomib, muromonab, otelixizumab, gusperimus, brentuximab vedotin, Ponesimod, KRP-203, FG-3019, emricasan, corticotropin, ibrutinib, cinryze, conestat, methoxy polyethylene glycol-epoetin beta, belimumab, blisibimod, atacicept, seliciclib, neihulizumab, everolimus, sirolimus, denileukin diftitox, LMB-2, natalizumab, catridecacog, ciclosporin, tacrolimus, voclosporin, voclosporin, canakinumab, mycophenolate, mizoribine, CE-1145, TK-DLI, abatacept, belatacept, olmesartan medoxomil, sparsentan, TXA-127, BIM-023, alemtuzumab, pentostatin, itolizumab, palifermin, leflunomide, PRO-140, cenicriviroc, fostamatinib, anifrolumab, sifalimumab, BAX-069, BG-00011, losmapimod, QPI-1002, ShigamAbs, TZ-101, F-652, reparixin, ladarixin, PTX-9908, aganirsen, APH-703, sotrastaurin, sotrastaurin, milatuzumab, SM-101, T-Guard, APG-101, DEX-M74, cardiotrophin-1, tiprelestat, ASKP-1240, BMS-986004, HPH-116, KD-025, OPN-305, TOL-101, defibrotide, pomalidomide, Thymoglobulin, laquinimod, remestemcel-L, Equine antithymocyte immunoglobulin, Stempeucel, LIV-Gamma, Octagam 10%, t2c-001, 99mTc-sestamibi, Clairyg, Prosorba, pomalidomide, laquinimod, teplizumab, FCRx, solnatide, foralumab, ATIR-101, BPX-501, ACP-01, ALLO-ASC-DFU, irbesartan+propagermanium, ApoCell, cannabidiol, RGI-2001, saratin, anti-CD3 bivalent antibody-diphtheria toxin conjugate, OMS-721, eculizumab, coversin, ACH-4471, ALN-CCS, AMY-101, IFX-1, IFX-2, IFX-3, LFG316, berinert, CB 2782, ANX005, APL-2, APL-1, PEG-Cp40, ALXN1007, bikaciomab, NOX-D20, NOX-E36, OMS906, mubodina, ALXN1210, ruconest, TNT009, SOBI005, SHP623, cinryze, lampalizumab, regenemab, RA101495, RA101295, zimura, NOX-100, LT-1951, and CD4+CD25+ regulatory T-cells.

Certain compounds of the present disclosure can exist in unsolvated forms as well as solvated forms, including hydrated forms. In general, the solvated forms are equivalent to unsolvated forms and are intended to be encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

Certain compounds of the present disclosure possess asymmetric carbon atoms (optical centers) or double bonds; the racemates, diastereomers, geometric isomers, regioisomers and individual isomers (e.g., separate enantiomers) are all intended to be encompassed within the scope of the present disclosure. The compounds of the present disclosure may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present disclosure, whether radioactive or not, are intended to be encompassed within the scope of the present disclosure.

The compounds disclosed herein are also meant to encompass all pharmaceutically acceptable compounds of Formulas (I), (Ia), (Ib), (Ic), (Id), (Ie) and compound 1 being isotopically-labeled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{36}$Cl, $^{123}$I, and $^{125}$I, respectively. These radiolabeled compounds could be useful to help determine or measure the effectiveness of the compounds, by characterizing, for example, the site or mode of action, or binding affinity to pharmacologically important site of action. Certain isotopically-labeled compounds of Formulas (I), (Ia), (Ib), (Ic), (Id), (Ie) and compound 1 for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability. For example, in vivo half-life may increase or dosage requirements may be reduced. Thus, heavier isotopes may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy. Isotopically-labeled compounds of Formulas (I), (Ia), (Ib), (Ic), (Id), (Ie) and compound 1 can generally be prepared by conventional techniques known to those skilled in the art or by processes analogous to those described in the Examples as set out below using an appropriate isotopically-labeled reagent in place of the non-labeled reagent previously employed.

The methods, compositions, kits and articles of manufacture provided herein use or include compounds (e.g., (I), (Ia), (Ib), (Ic), (Id), (Ie) and compound 1) or pharmaceutically acceptable salts, prodrugs, or solvates thereof, in which from 1 to n hydrogen atoms attached to a carbon atom may be replaced by a deuterium atom or D, in which n is the number of hydrogen atoms in the molecule. As known in the art, the deuterium atom is a non-radioactive isotope of the hydrogen atom. Such compounds may increase resistance to metabolism, and thus may be useful for increasing the half-life of compounds or pharmaceutically acceptable salts, prodrugs, or solvates thereof, when administered to a mammal. See, e.g., Foster, "Deuterium Isotope Effects in Studies of Drug Metabolism", Trends Pharmacol. Sci., 5 (12):524-527 (1984). Such compounds are synthesized by means well known in the art, for example by employing starting materials in which one or more hydrogen atoms have been replaced by deuterium.

Treatment methods provided herein include, in general, administration to a patient an effective amount of the compounds provided herein. Suitable patients include those patients suffering from or susceptible to (i.e., prophylactic treatment) C3 glomerulonephritis.

In general, treatment methods provided herein comprise administering to a patient an effective amount of a compound provided herein. In a preferred embodiment, the compound(s) of the disclosure are preferably administered to a patient (e.g., a human) orally or topically. In another embodiment, the compound(s) of the disclosure are administered to a patient (e.g., a human) systemically (intravenously or subcutaneously). The effective amount may be an amount sufficient to modulate C5a receptor activity and/or an amount sufficient to reduce or alleviate the symptoms presented by the patient. Preferably, the amount administered is sufficient to yield a plasma concentration of the compound (or its active metabolite, if the compound is a pro-drug) high enough to detectably inhibit white blood cell (e.g., neutrophil) chemotaxis in vitro. Treatment regimens may vary depending on the compound used and the particular condition to be treated; for treatment of most disorders, a frequency of administration of 4 times daily or less is preferred. In general, a dosage regimen of 2 times daily is more preferred, with once a day dosing particularly preferred. It will be understood, however, that the specific dose level and treatment regimen for any particular patient will depend upon a variety of factors including the activity of the specific compound employed, the age, body weight, general health, sex, diet, time of administration, route of administration, rate of excretion, drug combination (i.e., other drugs being administered to the patient) and the severity of the particular disease undergoing therapy, as well as the judgment of the prescribing medical practitioner. In general, the use of the minimum dose sufficient to provide effective therapy is preferred. Patients may generally be monitored for therapeutic effectiveness using medical or veterinary criteria suitable for the condition being treated or prevented.

Dosage levels of the order of from about 0.1 mg to about 140 mg per kilogram of body weight per day are useful in the treatment or preventions of conditions involving pathogenic C5a activity (about 0.5 mg to about 7 g per human patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient. For compounds administered orally, transdermally, intravenously, or subcutaneously, it is preferred that sufficient amount of the compound be administered to achieve a serum concentration of 5 ng (nanograms)/mL-10 µg (micrograms)/mL serum, more preferably sufficient compound to achieve a serum concentration of 20 ng-1 µg/ml serum should be administered, most preferably sufficient compound to achieve a serum concentration of 50 ng/ml-200 ng/ml serum should be administered. For direct injection into the synovium (for the treatment of arthritis) sufficient compounds should be administered to achieve a local concentration of approximately 1 micromolar.

Frequency of dosage may also vary depending on the compound used and the particular disease treated. However, for treatment of most disorders, a dosage regimen of 4 times daily, three times daily, or less is preferred, with a dosage regimen of once daily or 2 times daily being particularly preferred. It will be understood, however, that the specific dose level for any particular patient will depend upon a variety of factors including the activity of the specific compound employed, the age, body weight, general health, sex, diet, time of administration, route of administration, and rate of excretion, drug combination (i.e., other drugs being administered to the patient), the severity of the particular disease undergoing therapy, and other factors, including the judgment of the prescribing medical practitioner.

Pharmaceutical Compositions

The compounds provided herein can be administered as compositions which will typically contain a pharmaceutical carrier or diluent.

The term "composition" as used herein is intended to encompass a product comprising the specified ingredients in the specified amounts, as well as any product which results, directly or indirectly, from combination of the specified ingredients in the specified amounts.

In some embodiments, the pharmaceutical composition further comprises one or more additional therapeutic agents.

The pharmaceutical compositions for the administration of the compounds of this disclosure may conveniently be presented in unit dosage form and may be prepared by any of the methods well known in the art of pharmacy and drug delivery. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions and self-emulsifications as described in U.S. Patent Application 2002-0012680, hard or soft capsules, syrups, elixirs, solutions, buccal patch, oral gel, chewing gum, chewable tablets, effervescent powder and effervescent tablets. Compositions intended for oral use may be prepared according to any method known to the art for the manufacture of pharmaceutical compositions and such compositions may contain one or more agents selected from the group consisting of sweetening agents, flavoring agents, coloring agents, antioxidants and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as cellulose, silicon dioxide, aluminum oxide, calcium carbonate, sodium carbonate, glucose, mannitol, sorbitol, lactose, calcium phosphate or sodium phosphate; granulating and disintegrating agents, for example, corn starch, or alginic acid; binding agents, for example PVP, cellulose, PEG, starch, gelatin or acacia, and lubricating agents, for example magnesium stearate, stearic acid or talc. The tablets may be uncoated or they may be coated, enterically or otherwise, by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, polyethylene glycol (PEG) of various average sizes (e.g., PEG400, PEG4000) and certain surfactants such as cremophor or solutol, or as soft gelatin capsules wherein the active ingredient is mixed with water or an oil medium, for example peanut oil, liquid paraffin, or olive oil. Additionally, emulsions can be prepared with a non-water miscible ingredient such as oils and stabilized with surfactants such as mono- or di-glycerides, PEG esters and the like.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxy-ethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the disclosure may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. Oral solutions can be prepared in combination with, for example, cyclodextrin, PEG and surfactants.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present disclosure may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter and polyethylene glycols. Additionally, the compounds can be administered via ocular delivery by means of solutions or ointments. Still further, transdermal delivery of the subject compounds can be accomplished by means of iontophoretic patches and the like. For topical use, creams, ointments, jellies, solutions or suspensions, etc., containing the compounds of the present disclosure are employed. As used herein, topical application is also meant to include the use of mouth washes and gargles.

The compounds of this disclosure may also be coupled a carrier that is a suitable polymers as targetable drug carriers. Such polymers can include polyvinylpyrrolidone, pyran copolymer, polyhydroxy-propyl-methacrylamide-phenol, polyhydroxyethyl-aspartamide-phenol, or polyethyleneoxide-polylysine substituted with palmitoyl residues. Furthermore, the compounds of the disclosure may be coupled to a carrier that is a class of biodegradable polymers useful in achieving controlled release of a drug, for example polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels. Polymers and semipermeable polymer matrices may be formed into shaped articles, such as valves, stents, tubing, prostheses and the like. In one embodiment of the disclosure, the compound of the disclosure is coupled to a polymer or semipermeable polymer matrix that is formed as a stent or stent-graft device.

Kits and Packages

The terms "kit" and "pharmaceutical kit" refer to a commercial kit or package comprising, in one or more suitable containers, one or more pharmaceutical compositions and instructions for their use. In one embodiment, kits comprising a compound of Formula (I), (Ia), (Ib), (Ic), (Id) or (Ie), or compound 1, or a pharmaceutically acceptable salt thereof, and instructions for its administration are provided. In one embodiment, kits comprising a compound of Formula (I), (Ia), (Ib), (Ic), (Id) or (Ie), or compound 1, or a pharmaceutically acceptable salt thereof, in combination with one or more (e.g., one, two, three, one or two, or one to three) additional therapeutic agents and instructions for their administration are provided.

In one embodiment, the compounds of this disclosure are formulated into administration units which are packaged in a single packaging. The single packaging encompasses but is not limited to a bottle, a child-resistant bottle, an ampoule, and a tube. In one embodiment, the compounds of this disclosure and optionally additional therapeutic agents, are formulated into administration units and every single administration unit is individually packaged in a single packaging. Such individually packaged units may contain the pharmaceutical composition in any form including but not limited to liquid form, solid form, powder form, granulate form, an effervescent powder or tablet, hard or soft capsules, emulsions, suspensions, syrup, suppositories, tablet, troches, lozenges, solution, buccal patch, thin film, oral gel, chewable tablet, chewing gum, and single-use syringes. Such individually packaged units may be combined in a package made of one or more of paper, cardboard, paperboard, metal foil and plastic foil, for example a blister pack. One or more administration units may be administered once or several times a day. One or more administration units may be administered three times a day. One or more administration units may be administered twice a day. One or more administration units may be administered on a first day and one or more administration units may be administered on the following days.

Compound 1 has the formula:

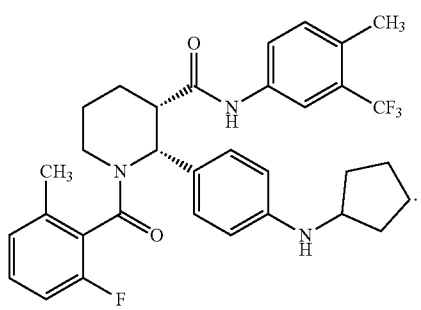 [SMILES: Cc1ccc(NC(=O)[C@H]2CCCN(C(=O)c3c(C)cccc3F)[C@H]2c2ccc(NC3CCCC3)cc2)cc1C(F)(F)F]

EXAMPLES

Example 1

Study of Compound 1 in a Patient with Progressive Complement 3 Glomerulonephritis Under the Special Needs program in the United Kingdom (which is similar to a compassionate use protocol in the US), a C3 glomerulonephritis patient received treatment with the orally administered complement inhibitor compound 1, following the protocol detailed below. The patient had refractory disease despite a kidney transplant and prior treatment with the broadly immunosuppressive drugs rituximab, cyclophosphamide, mycophenolate mofetil, tacrolimus, and steroids. Renal allograft biopsies were taken pre-dose, 2 and 7 months during therapy.

Results

The patient's condition improved in response to compound 1 treatment. The improvement seen with compound 1 treatment in this patient was based on the on-treatment kidney biopsy histologic findings that showed clearance of glomerular endocapillary proliferation and a marked decrease in glomerular inflammatory macrophages compared to the pre-treatment biopsy. Proteinuria dropped approximately 80% with compound 1 treatment.

Estimated glomerular filtration rate (eGFR) was 83 mL/min/1.73 m$^2$ 14 months prior to treatment with compound 1 and deteriorated to 46 mL/min/1.73 m$^2$ when treatment with compound 1 was started. Treatment with compound 1 attenuated or stopped the eGFR decline.

After 1 month of treatment, the eGFR decline was already attenuated (FIG. 1 shows the eGFR prior and after treatment with compound 1). Repeat biopsies showed resolution of glomerular endocapillary hypercellularity and reduction in glomerular macrophages. Compound 1 stabilized eGFR and reduced glomerular inflammation.

TABLE 1

Endocapillary hypercellularity, Immunoflourescence microscopy and CD68-positive cells/glomerulus at different time points.

| | Endocapillary hypercellularity/ total | Immunoflourescence microscopy | CD68-positive cells/glomerulus |
|---|---|---|---|
| Pre-treatment | 3/11 | C3, 2+; IgM, trace | 11 |
| 2 months | 0/36 | C3, 2+; IgM, neg | 2-3 |
| 7 months | 0/14 | C3, 2+; IgM, neg | 1-2 |

FIG. 2 represents the histopathological improvement following treatment with compound 1.
  (A) Haematoxylin and Eosin (H&E) staining before treatment with compound 1 demonstrates fibrinoid necrosis and multiple inflammatory cells.
  (C) Periodic acid-Schiff (PAS) staining after treatment with compound 1 shows a reduction in endocapillary hypercellularity and glomerular inflammation.
  (B) CD68 staining before treatment with compound 1.
  (D) CD68 staining after treatment with compound 1 demonstrates a reduction in glomerular macrophages.

Protocol of the Study

Aim

The aim of this study is to evaluate the efficacy, safety, and tolerability of compound 1 in a patient with progressive complement 3 (C3) glomerulonephritis.

Objectives

The primary safety objective of this study is to evaluate the safety and tolerability of compound 1.

The primary efficacy objective is to evaluate the efficacy of compound 1 based on change from baseline in eGFR (MDRD, Estimated Glomerular Filtration Rate) and proteinuria.

The secondary objectives of this study include assessment of:
  1. Change from baseline in pharmacodynamic markers in plasma and urine, e.g., MCP-1, C3a, C5a, properdin, and sC5b-9;
  2. Change from baseline in glomerular pathology based on renal biopsy;
  3. Evaluation of the plasma concentrations of compound 1 in C3 glomerulonephritis.

Methodology

This is a clinical study to test the safety, tolerability, and efficacy of compound 1 in a patient with recurrent C3GN in a renal transplant.

The patient will have biopsy proven recurrent C3GN prior to start of dosing, and be deemed eligible based on the inclusion and exclusion criteria. Screening procedures will include recording of demographics, medical history, medication history, physical examination and vital signs, serum chemistry, hematology, urinalysis (including UPCR measurement), viral screening (if not performed within prior 12 weeks), and estimated glomerular filtration rate (eGFR) assessment based on serum creatinine. The baseline eGFR needs to be at least 25 mL/min/1.73 m² for study eligibility.

On Day 1, the patient will start compound 1 treatment. Patients will take compound 1 30 mg orally twice daily for an initial period of 84 days. The patient will visit the study center on Days 1, 8, 15, 29, 57, and 85. The compound 1 dose will be taken in the morning optimally within one hour after breakfast and in the evening optimally within one hour after dinner. If the patient's clinical condition stabilizes or improves, and there are no adverse events preventing further treatment, the patient may be treated for another 84-day treatment cycle. The 84-day cycles may be repeated for a total of up to 4 cycles under this protocol. For the 84-day cycles after the first cycle, the patient will visit the study center every 4 weeks. There will be 4-week follow-up period after the patient stops the compound 1 treatment.

At the Day 1 and post-Day 1 study visits, blood and urine samples will be collected for safety, efficacy, and pharmacokinetic measurements. Physical examinations and vital signs assessments will be performed throughout the study. Concomitant medication and adverse event assessments will be made at every study visit. If at all possible, a renal biopsy will be performed after an appropriate follow-up period to assess the changes in kidney histology.

No new treatment for C3 GN may be added during the study period (active treatment period or follow up), unless the subject's condition deteriorates to the extent that the investigator deems it in the best interest of the subject to do so.

Duration of treatment with compound 1: 84 days with up to 3 repeats of the 84-day cycle for a total period of up to 336 days.

Duration of follow up after end of treatment with study medicine: 4 weeks.

The patient's condition will be evaluated by the Investigator at the end of the study and appropriate standard of care medical treatment will be provided as needed.

Main Criteria for Inclusion
1. Biopsy-proven C3 GN based on a renal biopsy within 8 weeks prior to screening;
2. eGFR≥25 mL/min/1.73 m² (by MDRD equation);
3. If having a partner of childbearing potential, must use adequate contraception throughout the study and for at least 3 months after completion of dosing; Adequate contraception is defined as resulting in a failure rate of less than 1% per year (combined estrogen and progestogen [oral, intravaginal, or transdermal], or progestogen-only hormonal contraception (oral, injectable, or implantable), intra-uterine device, intra-uterine hormone releasing system, bilateral tubal occlusion, vasectomized partner, or sexual abstinence);
4. Willing and able to give written Informed Consent and to comply with the requirements of the study protocol; and
5. Judged to be otherwise healthy by the Investigator, based on medical history, physical examination, and clinical laboratory assessments. Clinical laboratory values that are outside of normal limits (other than those specified in the Exclusion Criteria) and/or with other abnormal clinical findings that are judged by the Investigator not to be of clinical significance, may be allowed.

Main Criteria for Exclusion
1. Proteinuria >8 g/day (or >8 g/g creatinine);
2. Use of eculizumab within 26 weeks prior to dosing;
3. History or presence of any form of cancer within the 5 years prior to screening, with the exception of excised basal cell or squamous cell carcinoma of the skin, or carcinoma in situ such as cervical or breast carcinoma in situ that has been excised or resected completely and is without evidence of local recurrence or metastasis;
4. Positive HBV, HCV, or HIV viral screening test;
5. Any infection requiring antibiotic treatment that has not cleared prior to starting compound 1 treatment on Day 1;
6. WBC count less than 4000/μL, or neutrophil count less than 2000/μL, or lymphocyte count less than 1000/μL;
7. Hemoglobin less than 9 g/dL (or 5.56 mmol/L) at screening;
8. Evidence of hepatic disease; AST, ALT, alkaline phosphatase, or bilirubin>3× the upper limit of normal;
9. Participated in any clinical study of an investigational product within 30 days prior to screening or within 5 half-lives after taking the last dose; and
10. History or presence of any medical condition or disease which, in the opinion of the Investigator, may place the subject at unacceptable risk for study participation.

Duration of Treatment and Observation

The patient will be screened within a period not to exceed 21 days prior to Day 1. The compound 1 treatment period is at least 84 days and up to 336 days, and the patient will be followed for 4 weeks (28 days) after dosing is stopped.

To the extent possible, any adverse events that are deemed study drug-related and are ongoing at discharge will be followed-up to resolution or until a determination is made that the unresolved event is stable. The patient's condition will be evaluated by the Investigator at the end of the study and appropriate standard of care medical treatment will be provided as needed.

Safety Assessments

Safety assessments include adverse events, physical examination abnormalities, vital signs, and clinical laboratory tests (including blood chemistry, hematology, and urinalysis).

Efficacy Assessments
Efficacy Assessments Include:
1. First morning urinary PCR;
2. eGFR by Modification of Diet in Renal Disease (MDRD) formula based on serum creatinine;
3. Plasma and urine pharmacodynamic markers, e.g., MCP-1, C3a, C5a, properdin, and sC5b-9;
4. Glomerular inflammation (e.g., crescents, inflammatory cell infiltrate, endocapillary proliferation) and C3 deposition in a follow-up renal biopsy sample;

Pharmacokinetic Assessments

Concentrations of compound 1 and possible metabolites will be determined in plasma from 2-mL blood samples collected in EDTA tubes on Days 8, 15, 29, 57, and 85. The date and time of the last dose of compound 1 prior to sample collection for compound 1 measurement will be recorded. The samples will be kept frozen at −70° C. or lower and shipped on dry ice for assay.

Plasma samples will continue to be collected every 4 weeks during any subsequent 84-day cycles.

Pharmacodynamic Markers

Plasma samples will be collected on Day 1 (pre-dose), and Days 8, 15, 29, 57, and 85 for pharmacodynamic marker measurements, including, for example, complement fragments, and inflammatory cytokine and chemokine levels. Urine samples will also be collected on Day 1 (pre-dose) and Days 8, 15, 29, 57, and 85 for biomarker assessments including, for example, MCP-1, complement fragments, and inflammatory chemokine and cytokine levels.

Plasma and urine samples will continue to be collected every 4 weeks during any subsequent 84-day cycles.

Renal Histology

Renal biopsies will be analyzed by periodic acid—Schiff (PAS) staining, immunofluorescence staining for C3, C5b-9, and potentially other markers. Electron microscopy may also be performed.

Statistical Methods

Demographics and Baseline Characteristics

All patient baseline characteristics and demographic data (age, sex, race, ethnicity, weight, height, body mass index, smoking status, viral test results, C3 GN disease duration (from time of first diagnosis based on renal biopsy), renal transplant history, eGFR, proteinuria (PCR), urinary MCP-1:creatinine ratio, physical examination abnormalities, medical history, previous (within 6 months of screening) and concomitant medications (including other treatments for C3 GN) at study entry will be listed.

Safety Analysis

The primary safety endpoint is the patient incidence of adverse events.

Other Safety Endpoints Include:
1. Change from baseline in all safety laboratory parameters;
2. Change from baseline in vital signs.

All clinical safety and tolerability data will be listed. Treatment-emergent adverse events will be listed by System Organ Class, by relatedness and by maximum severity. Serious adverse events and adverse events leading to withdrawal will be listed. Vital signs and change from baseline in vital signs will be listed by study visit. Laboratory data (actual values and change from baseline) will be listed by study visit. Abnormal laboratory values will be flagged.

Efficacy Analysis

The primary efficacy endpoints are the change from baseline over the treatment period in eGFR and first morning urinary PCR.

Other efficacy endpoints include:
1. The percent change from baseline in plasma and urinary biomarkers, e.g., MCP-1, C3a, C5a, properdin, and sC5b-9;
2. Change from baseline to follow-up biopsy in glomerular inflammation (crescents, inflammatory cell infiltrate, and endocapillary proliferation), C3 deposits, and C5b-9 deposits.

Change and percent change in the efficacy parameters during the 4-week follow-up period will also be assessed to determine the off-treatment effect.

Pharmacokinetic Analysis

Plasma samples will be collected on Days 8, 15, 29, 57, and 85 to determine the plasma concentrations of compound 1 (and metabolites). Plasma concentrations of compound 1 will be listed and plotted by study visit.

Example 2

A Randomized, Double-Blind, Placebo-Controlled Phase 2 Study to Evaluate the Safety and Efficacy of Compound 1 in Patients with C3 Glomerulopathy Protocol of the Study Planned Aim The aim of this study is to evaluate the effect of compound 1 treatment on renal disease activity in patients with complement 3 glomerulopathy (C3G). The intent is to slow down or improve renal disease with compound 1 treatment in these patients.

Objectives

The primary objective is to evaluate the efficacy of compound 1 compared to placebo based on histologic changes in C3G pathology from kidney biopsies taken before and during treatment.

The secondary objectives of this study include assessment of:
1. The safety of compound 1 compared to placebo based on the incidence of adverse events, changes in clinical laboratory measurements, and vital signs;
2. Changes in laboratory parameters of renal disease including estimated glomerular filtration rate (eGFR), proteinuria, and urinary excretion of monocyte chemoattractant protein-1 (MCP-1) with compound 1 compared to placebo;
3. Health-related quality-of-life changes based on Short Form-36 version 2 (SF-36 v2) and EuroQOL-5D-5L (EQ-5D-5L) with compound 1 compared to placebo;
4. Evaluation of the pharmacokinetic profile of compound 1 in patients with C3 glomerulopathy.

Additionally, changes from baseline in markers of alternative complement pathway involvement, e.g., C3, C3d, C3c, C3adesArg, C5, C5a, C5b-9, C5adesArg, and other markers of inflammation, may be assessed in plasma/serum or urine over the course of the treatment period.

Methodology

This is a Phase 2 study to test the efficacy, safety, and tolerability of compound 1 in patients with C3G, including both C3GN and DDD. Eligible patients will be stratified based on two factors:
1. C3GN or DDD, and
2. Having received a kidney transplant or not, prior to randomization.

Patients will then be randomized, 1:1, to receive 30 mg compound 1 twice daily or matching placebo for 26 weeks in a double-blind, placebo-controlled manner. The 26-week double-blind period will be followed by a 26-week period during which all patients will receive compound 1 treatment.

Patients will be screened for enrollment based on biopsy proven C3 glomerulopathy (i.e., ≥2-levels of magnitude greater staining of C3 than any combination of IgG, IgM, IgA, and C1q) and evidence of inflammation based on leukocyte infiltration and/or endocapillary proliferation.

The screening period will be up to 28 days. Screening procedures will include written informed consent, demographics, medical history, medication history, physical examination and vital signs, 12-lead ECG, serum pregnancy test for women of childbearing potential, serum chemistry (including serum creatinine), hematology, urinalysis, urinary protein:creatinine ratio (PCR), viral and TB screening. If a patient did not have a renal biopsy in the past 12 weeks, a renal biopsy needs to be done prior to dosing. Prior to starting study drug treatment, blood samples will be collected for the following measurements to create a baseline profile for all patients:
1. C3, C3 d, C3c, C3adesArg, and C4;
2. C3 nephritic factor;
3. C5, C5a, C5b-9, C5adesArg;
4. Serum complement Factor H and factor B;
5. Serum paraprotein detection;
6. Complement factor H related protein 5 (CFHR5) mutation.

Patients meeting inclusion criteria will start study drug treatment on Day 1. Patients will take compound 1 30 mg or matching placebo orally twice daily. The treatment period is 52 weeks (364 days). The study drug will be taken in the morning preferably with food and in the evening preferably with food, approximately 12 hours after the morning dose. Patients who receive placebo during the first 26 weeks, will receive compound 1 in a blinded cross-over. After the 364-day treatment period, all patients will be followed for 8 weeks (56 days) without study drug treatment.

At post-Day 1 study visits, blood and urine samples will be collected for safety, efficacy, and pharmacokinetic and biomarker measurements. A serum pregnancy test for women of childbearing potential will be done regularly during the 52-week treatment period and at the end of the 8-week follow-up period. Physical examinations and vital signs assessments will be performed throughout the study. Health-related quality of life using the EQ-5D-5L and SF-36 v2 surveys will be assessed periodically over the course of the study. Study drug will be dispensed and drug accountability will be done. Concomitant medication and adverse event assessments will be made at every study visit. A follow-up renal biopsy will be performed at the following time points:
1. After the 26-week placebo-controlled treatment period;
2. If a patient is withdrawn early from the study, and
3. After the 52-week treatment period.

If a patient is on other immunosuppressive treatment at the start of dosing, the dose(s) of concomitant immunosuppressive treatment may not be increased during the study. Treatment with these other drugs may be reduced or stopped during the study, if the patient's condition justifies it. No new treatments may be added during the study period (active treatment period or follow up), unless the patient's condition deteriorates to the extent that the investigator deems it in the best interest of the patient to do so. This will be considered a treatment failure.

Patients who experience deteriorating renal function based on an increase in serum creatinine of at least 50% (confirmed by a repeat measurement after 2 weeks) which is otherwise not explained (e.g., dehydration, new medication), or an increase in proteinuria of >3 g/g creatinine from baseline or to a level >8 g/g (confirmed by a repeat measurement after 2 weeks) during the 52-week treatment period, will exit the treatment phase of the study and be treated at the discretion of their doctor. They will remain in the study for follow up and outcome recording. These will be considered treatment failures.

For study centers where enrollment of adolescents (12 to 17 years old) is approved, compound 1 or placebo dosing will initially be given based on the body weight at screening and the dose will be adjusted based on compound 1 plasma levels as shown in the table below.

Only in 12 to 17 year old patients, blood samples will be taken pre-dosing and at Hours 0.5, 1, 2, 3, 4, and 6 after the first compound 1 dose on Day 1 and plasma samples will be sent to the central laboratory for expeditious measurement of compound 1 and its metabolite in these patients. Dose adjustments will be made based on $AUC_{0-6}$ as shown in the table below. These $AUC_{0.6}$ thresholds are based on the mean compound 1 plasma exposure (525 ng·hr/mL) and one standard deviation (174 ng·hr/mL) above or below the mean in adult patients from Phase 2 study CL002_168 in AAV.

| Body weight | Initial compound 1/placebo dose | compound 1 Plasma $AUC_{0-6}$ (ng · hr/mL) on Day 1 | compound 1 Dose Adjustment |
|---|---|---|---|
| <40 kg (88 lb) | 10 mg twice daily | ≥351 | None |
|  |  | <351 | Increase dose to 20 mg twice daily |
| 40-55 kg (88-121 lb) | 20 mg twice daily | 351 to 699 | None |
|  |  | <351 | Increase dose to 30 mg twice daily |
|  |  | >699 | Decrease dose to 10 mg twice daily |
| >55 kg (121 lb) | 30 mg twice daily | ≤699 | None |
|  |  | >699 | Decrease dose to 20 mg twice daily |

Patients will visit the study center during Screening and on Day 1 (baseline) and Weeks 1, 2, 4, 8, 12, 16, 20, 26, 32, 38, 44, 52, and 60.

Duration of double-blind treatment with compound 1 or placebo: 26 weeks.

Duration of treatment with compound 1 after the double-blind treatment period: 26 weeks.

Duration of follow up after end of treatment with study medicine: 8 weeks.

Patients will be discharged from the study when all the Week 60 visit procedures have been completed. The patient's condition will be evaluated by the Investigator at the end of the clinical trial (Week 60) and appropriate standard of care medical treatment will be provided to all patients as needed.

Number of Patients

Approximately 44 male or female patients with C3 glomerulopathy will be enrolled in this study. Patients who drop out before the Week 26 visit may be replaced.

Main Criteria for Inclusion
1. Biopsy-proven C3 glomerulopathy, either DDD or C3GN, with 2-levels of magnitude greater staining of C3 than any combination of IgG, IgM, IgA, and C1q, and with evidence of inflammation, based on leukocyte infiltration or endocapillary proliferation, observed in a renal biopsy taken within 12 weeks prior to screening or during screening; patients with a kidney transplant are eligible for the study;
2. Plasma C5b-9 above the upper limit of the reference range of the central laboratory;
3. Male or female patients, aged at least 18 years; where approved, adolescents (12-17 year old) may be enrolled; female patients of childbearing potential may participate if adequate contraception is used during, and for at least the three months after study completion; Male patients with partners of childbearing potential may participate in the study if they had a vasectomy at least 6 months prior to randomization or if adequate contraception is used during, and for at least the three months after study completion; Adequate contraception is defined as resulting in a failure rate of less than 1% per year (combined estrogen and progestogen [oral, intravaginal, or transdermal], or progestogen-only hormonal contraception (oral, injectable, or implantable), intra-uterine device, intra-uterine hormone releasing system, bilateral tubal occlusion, vasectomized partner, or sexual abstinence);
4. Willing and able to give written Informed Consent and to comply with the requirements of the study protocol; written Informed Consent should be obtained from the legal guardian in accordance with regional laws or regulations for patients 12 to 17 years of age; and
5. Judged to be otherwise fit for the study by the Investigator, based on medical history, physical examination, and clinical laboratory assessments. Patients with clinical laboratory values that are outside of normal limits (other than those specified in the Exclusion Criteria) and/or with other abnormal clinical findings that are judged by the Investigator not to be of clinical significance, may be entered into the study.

Main Criteria for Exclusion
1. Pregnant or nursing;
2. Proteinuria >8 g/day (or >8 g/g creatinine);
3. More than 50% interstitial fibrosis on renal histology;
4. Use of eculizumab within 26 weeks prior to dosing;
5. Secondary C3 disease, e.g., infection-associated disease, or associated with another systemic or autoimmune disease;
6. Currently on dialysis or likely will require dialysis within 7 days;
7. History or presence of any form of cancer within the 5 years prior to screening, with the exception of excised basal cell or squamous cell carcinoma of the skin, or carcinoma in situ such as cervical or breast carcinoma in situ that has been excised or resected completely and is without evidence of local recurrence or metastasis;
8. Positive HBV, HCV, or HIV viral screening test;
9. Evidence of tuberculosis based on interferon γ release assay (IGRA), tuberculin purified protein derivative (PPD) skin test, or chest radiography done at screening or within 6 weeks prior to screening;
10. WBC count less than 3500/uL, or neutrophil count less than 1500/uL, or lymphocyte count less than 800/uL before start of dosing;
11. Evidence of hepatic disease; AST, ALT, alkaline phosphatase, or bilirubin >3× the upper limit of normal before start of dosing;
12. Known hypersensitivity to compound 1 or inactive ingredients;
13. Participated in any clinical study of an investigational product within 30 days prior to screening or within 5 half-lives after taking the last dose; and
14. History or presence of any medical condition or disease which, in the opinion of the Investigator, may place the patient at unacceptable risk for study participation.

Duration of Treatment and Observation

Patients will be screened within a period not to exceed 28 days prior to Day 1. The treatment period is 52 weeks (364 days) and all patients will be followed for 8 weeks (56 days) after the dosing period.

To the extent possible, any adverse events that are deemed study drug-related and are ongoing at discharge will be followed-up to resolution or until a determination is made that the unresolved event is stable. The patient's condition will be evaluated by the Investigator at the end of the clinical trial and appropriate standard of care medical treatment will be provided to all patients as needed.

Safety Assessments

Safety assessments include adverse events, physical examination abnormalities, vital signs, and clinical laboratory tests (including blood chemistry, hematology, and urinalysis).

Efficacy Assessments

Efficacy Assessments Include:
1. Renal histology to determine the C3G Histologic Index (CHI) for disease activity and chronicity;
2. eGFR calculated by the Modification of Diet in Renal Disease (MDRD) equation from serum creatinine;
3. First morning urinary PCR;
4. First morning urinary MCP-1:creatinine ratio;
5. EQ-5D-5L and SF-36 v2.

Pharmacokinetic Assessments

Concentrations of compound 1 and metabolites will be determined in plasma according to the Time and Events Table.

Pharmacodynamic Markers

Plasma/serum samples will be collected according to the Time and Events Table for pharmacodynamic marker measurements, including, for example, complement fragments, and inflammatory cytokine and chemokine levels. Urine samples will also be collected according to the Time and Events Table for biomarker assessments including, for example, complement fragments, sCD163, and inflammatory chemokine and cytokine levels.

Renal Histology

For eligibility assessment, renal biopsy samples will be assessed by immunofluorescence staining for C3 and immunoglobulins. Patients must have biopsy-proven C3 glomerulopathy, either DDD or C3GN, with ≥2-levels of magnitude greater staining of C3 than any combination of IgG, IgM, IgA, and C1q, and with evidence of inflammation, based on leukocyte infiltration or endocapillary proliferation, observed in a renal biopsy taken within 12 weeks prior to screening or during screening.

All renal biopsies will also be analyzed based on hematoxylin-eosin (H&E) staining, periodic acid-Schiff (PAS) staining, trichrome, and Jones methenamine silver staining. These renal biopsies will be evaluated by a central reader, blinded to treatment assignment from either slides or high-resolution electronic images.

The central reader will determine the degree of disease activity and chronicity.

Statistical Methods

Demographics and Baseline Characteristics

All patient baseline characteristics and demographic data (age, sex, race, ethnicity, weight, height, body mass index, viral test results, C3 glomerulopathy disease duration (from time of first diagnosis based on renal biopsy), eGFR, proteinuria (PCR), complement marker levels, urinary MCP-1:creatinine ratio, physical examination abnormalities, medical history, previous (within 6 months of screening) and concomitant medications (including other treatments for C3 glomerulopathy) at study entry will be listed by study center and patient number, and will also be summarized.

Efficacy Analysis

The primary efficacy endpoint is the percent change from baseline to week 26 in the C3G Histologic Index (CHI) for disease activity. The compound 1 and placebo groups will be compared by ANCOVA with treatment group and randomization strata (C3GN or DDD, and renal transplant or not) as factors, and baseline as covariate. Point estimates and corresponding 95% confidence intervals will be estimated for the difference between the compound 1 and placebo control group.

Since the placebo group will receive compound 1 during the second 26 weeks of the study, the change from Week 26 to Week 52 in the CHI in the placebo control group will be compared to the change from baseline to Week 26 in this group. This analysis will be done by the paired t-test. Point estimates and corresponding 95% confidence intervals will be estimated for the difference between the second 26 weeks (compound 1 treatment) and the first 26 weeks (placebo treatment).

The change from baseline to Week 52 in the CHI will also be compared to the change from baseline with Week 26 in placebo control group using similar methodology as described for the primary efficacy endpoint.

Other Efficacy Endpoints Include:
1. The percent change from baseline in the CHI for disease chronicity over the placebo-controlled 26-week treatment period;
2. The change and percent change from baseline in eGFR over the placebo-controlled 26-week treatment period;
3. The percent change from baseline in urinary PCR over the placebo-controlled 26-week treatment period;
4. The percent change from baseline in urinary MCP-1:creatinine ratio over the placebo-controlled 26-week treatment period;
5. Change from baseline in EQ-5D-5L and SF-36 v2 (domains and component scores) over the placebo-controlled 26-week treatment period.

Continuous variables, including eGFR, urinary PCR, urinary MCP-1:creatinine ratio, EQ-5D-5L, and SF-36 v2 will be analyzed using a mixed effects model for repeated measures (MMRM) with treatment group, visit, treatment-by-visit interaction, and randomization strata (C3GN or DDD, and renal transplant or not) as factors, and baseline as covariate. Patients will be considered as repeated measure units over visits. Point estimates and corresponding 95% confidence intervals will be estimated for the difference between the compound 1 group and the control group across 26 weeks using simple contrast from the model. Similar to the primary endpoint, the second 26 weeks will be compared to the first 26 weeks for the placebo group.

Change and percent change in the efficacy parameters during the 8-week follow-up period will also be assessed to determine the off-treatment effect.

Change from baseline in markers of alternative complement pathway activation will be reported.

Summary statistics will be calculated for each of the efficacy endpoints. For continuous variables, numbers, means, medians, ranges, standard deviations, standard errors, and 95% confidence intervals will be calculated. Geometric means will be calculated for urinary PCR and MCP-1:creatinine, and other measurements that are not normally distributed.

Safety Analysis

Safety Endpoints Include:
1. Patient incidence of treatment-emergent serious adverse events, adverse events, and withdrawals due to adverse events;
2. Change from baseline and shifts from baseline in all safety laboratory parameters;
3. Change from baseline in vital signs.

All patients who are randomized and received at least one dose of study medication will be included in the safety population.

All clinical safety and tolerability data will be listed by treatment group and by patient, and will be summarized by treatment group.

All reported adverse events will be coded using MedDRA and listed by System Organ Class, preferred term, and verbatim term.

Treatment-emergent adverse events will be listed and summarized by treatment group by System Organ Class, by relatedness and by maximum severity.

Treatment-emergent serious adverse events and adverse events leading to withdrawal will be summarized by treatment group.

Individual vital signs and change from baseline in vital signs will be listed by treatment group, patient, and study visit, and summarized by treatment group.

Laboratory data (actual values and change from baseline) will be listed by treatment group, patient, and study visit. Abnormal laboratory values will be flagged. Laboratory data will also be summarized by treatment group and study visit. Shift tables will be generated for shifts in laboratory parameters by study visit.

Pharmacokinetic and Pharmacodynamic Marker Analysis

Plasma samples will be collected over the course of the study to determine the PK profile of compound 1 (and metabolites). Individual plasma concentrations of compound 1 (and metabolites) will be listed, plotted, and summarized descriptively and graphically. PK parameters will be calculated based on plasma compound 1 concentrations at the time of sample collection in relation to time of administration of the most recent dose of study medication. PK parameters of significant metabolites may also be calculated.

Plasma and urinary PD markers will be summarized and may be analyzed using methods analogous to the efficacy parameters. The following parameters will be determined, where possible, in 12-17 year old patients:

Cmax Maximum plasma concentration
tmax Time of maximum plasma concentration
$AUC_{0-6}$ Area under the plasma concentration-time curve from Time 0 to Hour 6 on Day 1
Cmin Trough level plasma concentrations at post-Day 1 visits The relationship between PK parameters and renal function based on eGFR will be evaluated. The data may also be used to evaluate the PK/PD relationship of compound 1 treatment. To this end, the change and/or percent change from baseline in urinary PCR, eGFR, urinary MCP-1:creatinine ratio, and other biomarkers may be used as PD markers.

What is claimed is:
1. A method of treating a human suffering from complement 3 glomerulopathy comprising administering to the human an effective amount of a compound having the formula

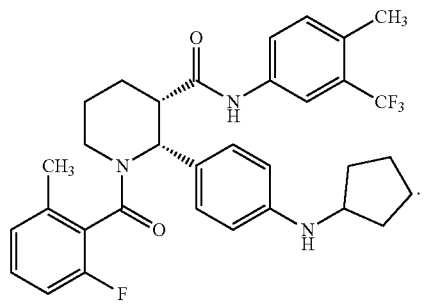 [SMILES: Cc1ccc(NC(=O)[C@H]2CCCN(C(=O)c3c(C)cccc3F)[C@H]2c2ccc(NC3CCCC3)cc2)cc1C(F)(F)F]

2. The method of claim 1 wherein the human suffers from complement 3 glomerulonephritis.

3. The method of claim 1 wherein the human suffers from progressive complement 3 glomerulonephritis.

4. The method of claim 1 wherein the human suffers from recurrent complement 3 glomerulonephritis after a renal transplant.

5. The method of claim 1 wherein the human suffers from dense deposit disease.

6. The method of claim 1 wherein the complement 3 glomerulopathy is refractory to other treatment.

7. The method of claim 1 wherein the complement 3 glomerulopathy is refractory to immunosuppressive drugs.

8. The method of claim 1 wherein the complement 3 glomerulopathy is refractory to one or more of rituximab, cyclophosphamide, mycophenolate mofetil, tacrolimus, and steroids.

9. The method of claim 1 wherein the compound is administered twice daily.

10. The method of claim 1 wherein the compound is administered once a day.

11. The method of claim 1 wherein the compound is administered orally.

12. The method of claim 1 wherein the human receives 30 mg of the compound twice daily.

13. The method of claim 1, wherein the human has a Complement factor H related protein 5 (CFHR5) mutation.

* * * * *